(12) United States Patent
Shim et al.

(10) Patent No.: US 12,109,532 B2
(45) Date of Patent: Oct. 8, 2024

(54) VARIANT OF NITROUS OXIDE REDUCTASE PROTEIN AND METHOD OF REDUCING CONCENTRATION OF NITROUS OXIDE IN SAMPLE

(71) Applicant: Samsung Electronics Co., Ltd., Suwon-si (KR)

(72) Inventors: Woo Yong Shim, Hwaseong-si (KR); Seung Hoon Song, Suwon-si (KR); Jae-Young Kim, Suwon-si (KR); Yu Kyung Jung, Hwaseong-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 82 days.

(21) Appl. No.: 17/751,066

(22) Filed: May 23, 2022

(65) Prior Publication Data
US 2023/0173432 A1 Jun. 8, 2023

(30) Foreign Application Priority Data

Dec. 8, 2021 (KR) .................. 10-2021-0175198

(51) Int. Cl.
*B01D 53/84* (2006.01)
*C12N 15/70* (2006.01)

(52) U.S. Cl.
CPC ............ *B01D 53/84* (2013.01); *C12N 15/70* (2013.01); *B01D 2251/95* (2013.01); *B01D 2255/804* (2013.01)

(58) Field of Classification Search
CPC ........ C12N 15/70; C12N 9/004; C12N 15/52; B01D 2257/404; C12Y 107/02004
See application file for complete search history.

(56) References Cited

U.S. PATENT DOCUMENTS

2022/0177896 A1 6/2022 Shim et al.

FOREIGN PATENT DOCUMENTS

JP 2014230534 A 12/2014

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Lin Zhang et al., "A [3Cu:2S] cluster provides insight into the assembly and function of the CuZ site of nitrous oxide reductase," Chemical Science, Jan. 15, 2021. pp. 3239-3244, vol. 12.
Lin Zhang et al., "Histidine-Gated Proton-Coupled Electron Transfer to the CuA Site of Nitrous Oxide Reductase," Journal of the American Chemical Society, Dec. 30, 2020, pp. 830-838, vol. 143.
Lin Zhanga et al., "Functional assembly of nitrous oxide reductase provides insights into copper site maturation," PNAS, Jun. 25, 2019, pp. 12822-12827, vol. 116, No. 26.

* cited by examiner

*Primary Examiner* — Iqbal H Chowdhury
(74) *Attorney, Agent, or Firm* — CANTOR COLBURN LLP

(57) ABSTRACT

Provided are recombinant microorganisms having a foreign gene encoding a variant of a nitrous oxide reductase protein, a composition comprising the recombinant microorganism or the variant of a nitrous oxide reductase protein for use in removing nitrous oxide in a sample, a variant of a nitrous oxide reductase protein, and a polynucleotide encoding the variant.

19 Claims, 3 Drawing Sheets
Specification includes a Sequence Listing.

VARIANT OF NITROUS OXIDE REDUCTASE PROTEIN AND METHOD OF REDUCING CONCENTRATION OF NITROUS OXIDE IN SAMPLE

CROSS-REFERENCE TO RELATED APPLICATION

This application is based on and claims priority under 35 U.S.C. § 119, and all of the benefits accruing therefrom, to Korean Patent Application No. 10-2021-0175198, filed on Dec. 8, 2021, in the Korean Intellectual Property Office, the content of which is incorporated by reference herein in its entirety.

BACKGROUND

1. Field

The present disclosure relates to recombinant microorganisms including foreign genes that encode variants of nitrous oxide reductase proteins, compositions for reducing a concentration of nitrous oxide in a sample that include the recombinant microorganisms or the variants of nitrous oxide reductase protein, and methods of reducing a concentration of nitrous oxide in a sample by using the recombinant microorganisms or the nitrous oxide reductase proteins.

2. Description of the Related Art

Nitrogen oxide (NOx) is one of the air pollutants mainly discharged during a combustion process of fuels, and examples of various nitrogen oxides (also referred to as NOx) are $N_2O$, $NO$, $N_2O_3$, $NO_2$, $N_2O_4$, $N_2O_5$, and the like. The main air pollutants among these examples are $NO$ and $NO_2$. $N_2O$, along with carbon dioxide ($CO_2$), methane ($CH_4$), and freon gas (e.g., fluorochlorocarbons (CFCs)), are the main cause of the greenhouse effect by which heat is absorbed and stored in the atmosphere, and is one of the six greenhouse gases regulated under the Kyoto Protocol. $N_2O$ has a Global Warming Potential (GWP) value of 310, exhibiting a high warming effect per unit mass compared to $CO_2$ and $CH_4$. In addition, nitrogen oxide is also a leading cause of smog and acid rain. Nitrogen oxide also forms second-generation ultrafine dust through chemical reactions in the air, and adversely affects respiratory health by increasing ground-level ozone concentrations.

Most nitrogen oxide removal processes are chemical reduction methods, such as a selective catalytic reduction (SCR) method and a selective non-catalytic reduction (SNCR) method, techniques using scrubbing and adsorption, and the like. Chemical methods have drawbacks in terms of the cost of energy and catalysts required throughout the whole process, the treatment of secondary waste generated during the process, and the like. In addition, in the case of an SCR or SNCR method, another greenhouse gas, $N_2O$, may be generated as a result of incomplete reduction during reducing $NO$ and $NO_2$. Unlike chemical techniques having such problems, biological processes are environmentally friendly and have advantages such as a relatively simple principle, no use of extreme conditions (including, e.g., high temperature and high pressure), and low generation of secondary waste or wastewater. In such biological processes, a microorganism serving as a biological catalyst may be used instead of a chemical catalyst, to oxidize or reduce NOx or to fix NOx as a part of cells.

However, despite advances, alternative methods of biological denitrification are still required.

SUMMARY

Denitrification microorganisms reduce nitrogen oxide to $N_2$ through a dissimilatory reductive process. In several previous studies, many denitrification microorganisms such as *Pseudomonas putida, Pseudomonas denitrificans, Pseudomonas stutzeri, Paracoccus denitrificans, Klebsiella pneumonia*, and the like have been reported.

Provided in an aspect are recombinant microorganisms including foreign genes encoding variants of nitrous oxide reductase proteins.

Provided in an aspect are compositions for use in reducing a concentration of nitrous oxide in a sample that includes nitrous oxide that include the recombinant microorganisms or the variants of the nitrous oxide reductase proteins.

Provided are methods of reducing a concentration of nitrous oxide in a sample that includes nitrous oxide, the method including contacting the sample with a variant of the nitrous oxide reductase protein or with a recombinant microorganism to reduce a concentration of nitrous oxide in the sample.

Provided in an aspect are variants of nitrous oxide reductase proteins and polynucleotides encoding the variants.

Additional aspects will be set forth in part in the description which follows and, in part, will be apparent from the description, or may be learned by practice of the presented embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
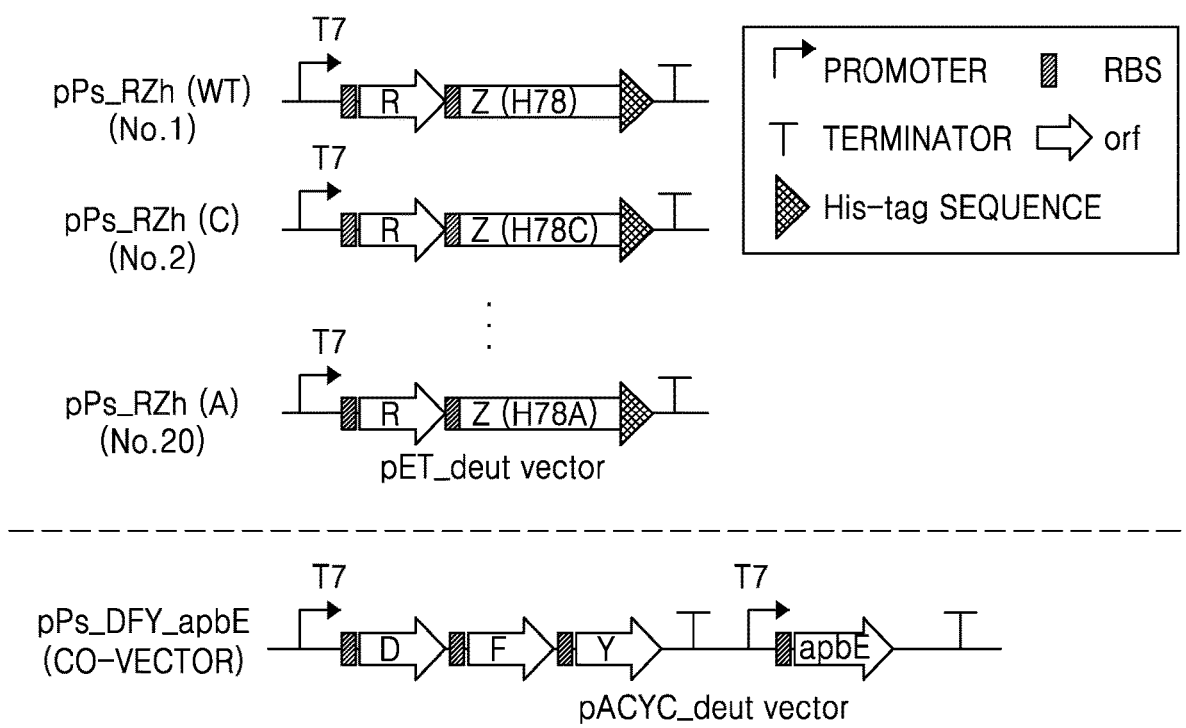
FIG. 1 is a diagram of a vector introduced into *E. coli*.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise. "Or" means "and/or." "At least one" is not to be construed as limiting "a" or "an." As used herein, the term "and/or" includes any and all combinations of one or more of the associated listed items. As used herein, the term "or" and "and/or" includes any and all combinations of one or more of the associated listed items. Expressions such as "at least one of," when preceding a list of elements, modify the entire list of elements and do not modify the individual elements of the list.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±20%, ±10% or ±5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The expression "increase in expression" or "increased expression" as used herein refers to a detectable increase in expression of a given gene. In particular, the expression "increased expression" refers to a level of gene expression of a given gene in a genetically modified cell (for example, a genetically engineered cell) that is greater compared to an expression level in a comparative cell of the same type as a cell without the same genetic modification (for example, a native cell or a "wild-type" cell). For example, the expression level of a gene in the modified cell may be increased by about 5% or more, about 10% or more, about 15% or more, about 20% or more, about 30% or more, about 50% or more, about 60% or more, about 70% or more, or about 100% or more, than the expression level of the same gene in an unengineered cell of the same type, for example, a wild-type cell or a parent cell of the modified cell. Cells with increased expression of proteins or enzymes may be identified using any method known in the art.

The increase in expression of a gene may be achieved by increasing the copy number of the gene. The expression "copy number increase" as it relates to a gene refers to an increase in copy number due to introduction or amplification of a given gene, and may also include a case in which a gene not present in an unengineered cell is obtained by genetic engineering. The gene introduction may be achieved through a vehicle such as a vector. The introduction may include transient introduction in which a gene is not integrated into the genome, or insertion of a gene into the genome. The introduction may be achieved by, for example, introducing a vector into which a polynucleotide encoding a desired polypeptide is inserted into a cell, and then replicating the vector in a cell or integrating the polynucleotide into the genome. The expression "copy number increase" may refer to an increase in the number of copies of a gene encoding one or more polypeptides of a complex when several polypeptides form the complex and exhibit activity of one nitrous oxide reductase.

The introduction of the gene into the cell may be performed by known methods such as transformation, transfection, electroporation, and the like. Here, the gene may be introduced through a vehicle, or may be introduced as it is. The term "vehicle" as used herein refers to a nucleic acid molecule capable of delivering another nucleic acid linked to the vehicle. In terms of a nucleic acid sequence that mediates the introduction of a particular gene, the vehicle as used herein is understood to be used interchangeably with a vector, a nucleic acid structure, and a cassette. A vector may include, for example, a plasmid-derived vector or a virus-derived vector. A plasmid may include a circular double-stranded DNA loop to which additional DNA may be ligated. The vector may include, for example, a plasmid expression vector or a viral expression vector including, for example, replication defective retrovirus, adenovirus, and adeno-associated virus, or a combination thereof.

The gene engineering described herein may be performed by a suitable molecular biological method known in the art.

The term "parent cell" as used herein refers to an original cell, for example, a cell of the same type as the engineered cell, but without the genetic modification. Regarding a particular genetic modification, the "parent cell" refers to a cell that does not have such a particular genetic modification, but may be the same as a genetically engineered cell for other circumstances. Thus, the parent cell may be used as a starting material to produce a genetically engineered microorganism having an increased (or decreased) expression level of a gene encoding a given protein (for example, a protein having at least about 75% of sequence identity with nitrous oxide reductase). The same comparison may be applied to other genetic modifications.

The term "gene" as used herein refers to a nucleic acid fragment encoding the information for expressing a particular protein, and may or may not include a regulatory sequence with a 5'-noncoding sequence and/or a 3'-noncoding sequence, or may be free of a regulatory sequence.

A "polypeptide" is a polymer chain comprised of amino acid residue monomers which are joined together through amide bonds (peptide bonds). In general, a polypeptide may include at least 10, 20, 50, 100, 200, 500, or more amino acid residue monomers.

The term "sequence identity" of a nucleic acid or polypeptide as used herein refers to the degree of identicalness of nucleotide (bases) of polynucleotide sequences or amino acid residues of a polypeptide between sequences, and is obtained after aligning both sequences to be as identical as possible (best match) in a specific comparison region. The sequence identity is a value measured by optimally aligning and comparing two sequences in a specific comparison region, and a portion of the sequences in the comparison region may be added or deleted compared to a reference sequence. A sequence identity percentage may be, for example, calculated by steps of: comparing two optimally aligned sequences throughout the comparison region; determining the number of positions in both sequences where identical amino acids or nucleotides appear to obtain the number of matched positions; dividing the number of the matched positions by the total number of positions within the comparison range (i.e., a range size); and multiplying the result by 100 to obtain a sequence identity percentage. The sequence identity percentage may be determined by using a known sequence comparison program, and examples of the program are BLASTn™ (NCBI), BLASTp™ (NCBI), CLC Main Workbench (CLC bio), MegAlign™ (DNASTAR Inc), and the like.

The term "genetic modification" as used herein refers to an artificial alternation in a composition or a structure of a genetic material in a cell.

The term "corresponding" as used herein refers to an amino acid position of a polypeptide or protein of interest that aligns with a stated position of a standard polypeptide or protein (e.g., position H78 of SEQ ID NO: 1), when the amino acid sequence (e.g., SEQ ID NO: 1) of the polypeptide protein of interest and a standard protein are aligned using an art-acceptable protein alignment program, such as a BLAST™ pairwise alignment program or a well-known Lipman-Pearson protein alignment program, with the following alignment parameters. Databases (DBs) in which standard sequences are stored may be RefSeq non-redundant protein databases of NCBI. The parameters used for the sequence alignment may be as follows: Ktuple=2, Gap Penalty=4, and Gap length penalty=12. Here, a range included in a "corresponding" sequence may be within a range of E-value 0.00001 and H-value 0.001.

A polypeptide or protein having an amino acid residue corresponding to position H78 of the amino acid sequence of SEQ ID NO: 1 obtained according to the alignment conditions above may be also referred to as a "homolog of nitrous oxide reductase". The nitrous oxide reductase may be, for example, derived from the genus *Pseudomonas* or the genus *Paracoccus*. A microorganism of the genus *Pseudomonas* may be *P. stutzeri* or *P. aeruginosa*. A microorganism of the genus *Paracoccus* may be *P. versutus*.

In the present specification, the nitrous oxide reductase protein before the occurrence of the amino acid alteration defined in the claims may be naturally occurring or a variant thereof. The variant thereof may include an amino acid alteration compared to naturally occurring one. The nitrous oxide reductase protein may be a polypeptide having a sequence identity of 75% or greater, for example, 80% or greater, for example, 85% or greater, for example, 90% or greater, for example, 95% or greater, or for example, 98% or greater, with the amino acid sequence of SEQ ID NO: 14, or 7. The nitrous oxide reductase protein gene may be a polynucleotide having a sequence identity of 75% or greater, for example, 80% or greater, for example, 85% or greater, for example, 90% or greater, for example, 95% or greater, or for example, 98% or greater, with the nucleotide sequence of SEQ ID NO: 2, 3, 5, 6, 8, or 9.

An "exogenous gene" as used herein refers to a gene that is not naturally present in a cell and is introduced into the cell from the outside of the cell. The introduced exogenous gene may be homologous or heterologous with respect to the host cell type into which the gene is introduced. The term "heterologous" means "not native" or "foreign."

An aspect of the present disclosure provides a recombinant microorganism including a foreign (i.e., exogenous) gene encoding a variant of a nitrous oxide reductase protein, wherein the variant includes an amino acid alteration of an amino acid residue corresponding to position H78 of the amino acid sequence of SEQ ID NO: 1 and has activity of an enzyme belonging to EC 1.7.2.4.

In the recombinant microorganism, nitrous oxide reductase may be an enzyme that catalyzes conversion of $N_2O$ to $N_2$ using $N_2O$ as a substrate. NosZ is a protein encoded by the nosZ gene, and is an enzyme that catalyzes the conversion of $N_2O$ to $N_2$. That is, NosZ is nitrous oxide reductase. NosZ may be a homodimeric metalloprotein of 130 kDa that contains two copper centers, CuA and CuZ, in each monomer. The nitrous oxide reductase may have an activity of enzymes belonging to EC 1.7.2.4.

The amino acid alteration may be a substitution of the amino acid residue corresponding to the H78 position with A, M, N, E, P, F, I, or C. The amino acid alteration may be an H78A, H78M, H78N, H78E, H78P, H78F, H78I or H78C substitution or a combination thereof.

The microorganism may further include a genetic modification that increases expression of a nosR gene encoding NosR, a nosD gene encoding NosD, a nosF gene encoding NosF, a nosY gene encoding NosY, and an apbE gene encoding ApbE, or a combination thereof.

NosR may be encoded by the nosR gene, and may be a polytopic membrane protein serving as an electron donor for the $N_2O$ reduction. NosD may be a protein encoded by the nosD gene, and may be essential for the formation of [4Cu:2S] copper center CuZ site in the NosD protein. In particular, NosD may supply sulfur (S) to NosZ. NosF and NosY are proteins and may be encoded by the nosF gene and the nosY gene, respectively, and may together form a complex, such as a tetramer, to serve as an ABC transporter. ApbE is a protein and may be encoded by the apbE gene, and may be a flavinyltransferase that transfers flavin to NosR.

The nitrous oxide may be in the form of Fe(II)(L)-NO. The Fe(II)(L)-NO may refer to a complex formed by chelating L, which is a chelating agent, $Fe^{2+}$, and NO. L in the complex may be, for example, ethylenediamine, diethylenetriamine, triethylenetetramine, hexamethylenetetramine, N-(2-hydroxyethyl)ethylenediamine-triacetic acid (HEDTA), ethylenediamine-tetraacetic acid (EDTA), iminodiacetic acid, nitrilo-triacetic acid (NTA), or diethylenetriaminepentaacetic acid (DTPA). Accordingly, the Fe(II)(L)-NO may be in a form such that a nitric oxide, such as $N_2O$, NO, $N_2O_3$, $NO_2$, $N_2O_4$, and $N_2O_5$, are modified to become soluble in an aqueous solution. The Fe(II)(L)-NO may be formed by contacting nitric oxide with a Fe(II)(L)-containing aqueous solution. The contacting may include mixing an aqueous medium with a liquid sample including the solubilized nitric oxide or contacting an aqueous medium with a sample including gaseous nitric oxide. However, in the reduction of the concentration of nitrous oxide in the sample using the recombinant microorganism, it is not necessarily limited to this or any particular mechanism.

The genetic modification may include a genetic modification for increasing the copy number of the nosZ gene, the copy number of nosR gene, the copy number of the nosD gene, the copy number of the nosF gene, the copy number of the nosY gene, the copy number of the apbE gene, or a combination thereof. The genetic modification may include introduction of the genes, for example, introduction of the genes through a vehicle such as a vector. The genes may be present intrachromosomally or extrachromosomally. The introduced genes may be present in a plurality of the copies of the genes. For example, the number of the introduced genes may each independently be 2 or more, 5 or more, 10 or more, 10 or more, 50 or more, 100 or more, or 1000 or more.

NosZ may be a polypeptide having at least 75% sequence identity with the amino acid sequence of SEQ ID NO: 1, 4, or 7. The nosZ gene may be a polynucleotide having at least 75% sequence identity with the nucleotide sequence of SEQ ID NO: 2, 3, 5, 6, 8, or 9.

NosR may be a polypeptide having at least 75% sequence identity to the amino acid sequence of SEQ ID NO: 10, 13, or 16. The nosR gene may be a polynucleotide having at least 75% sequence identity with the nucleotide sequence of SEQ ID NO: 11, 12, 14, 15, 17, or 18.

The NosD may be a polypeptide having at least 75% sequence identity to the amino acid sequence of SEQ ID NO: 19, 22, or 25. The nosD gene may be a polynucleotide having at least 75% sequence identity with the nucleotide sequence of SEQ ID NO: 20, 21, 23, 24, 26, or 27.

The NosF may be a polypeptide having at least 75% sequence identity to the amino acid sequence of SEQ ID NO: 28, 31, or 34. The nosF gene may be a polynucleotide having at least 75% sequence identity with the nucleotide sequence of SEQ ID NO: 29, 30, 32, 33, 35, or 36.

The NosY may be a polypeptide having at least 75% sequence identity to the amino acid sequence of SEQ ID NO: 37, 40, or 43. The nosY gene may be a polynucleotide having at least 75% sequence identity with the nucleotide sequence of SEQ ID NO: 38, 39, 41, 42, 44, or 45.

The ApbE may be a polypeptide having at least 75% sequence identity with the amino acid sequence of SEQ ID NO: 46, 49, or 52. The apbE gene may be a polynucleotide having at least 75% sequence identity with the nucleotide sequence of SEQ ID NO: 47, 48, 50, 51, 53, or 54.

In the recombinant microorganism, six genes, i.e., each of the nosZ gene, the nosR gene, the nosD gene, the nosF gene, the nosY gene, and the apbE gene, may be introduced into the recombinant microorganism through a vector. The vector may exist outside a chromosome of the recombinant microorganism (e.g., not incorporated/integrated in a chromosome of the recombinant microorganism).

In the recombinant microorganism, the nosZ gene and the nosR gene may be included in a first vector, and the nosD gene, the nosF gene, the nosY gene, and the apbE gene may be included in a second vector, which may be different from the first vector in which the nosZ gene and the nosR gene are included.

In the recombinant microorganism, the nosZ gene and the nosR gene may be included in a first operon; the nosD gene and the nosF gene may be included in a second operon; the nosY gene and the apbE gene may be included in a third operon; and the nosD gene, the nosF gene, and the nosY gene may be included in a fourth of operon. Here, the operon in which the nosZ gene and the nosR gene are included, the operon in which the nosD gene and the nosF gene are included, the operon in which the nosY gene and the apbE gene are included, and the operon in which the nosD gene, the nosF gene, and the nosY gene are included may be included in vectors that may be different from each other.

The recombinant microorganism may belong to the genus *Pseudomonas*, the genus *Paracoccus*, or the genus *Escherichia*, or a combination thereof. The microorganism of the genus *Pseudomonas* may be *P. stutzeri* or *P. aeruginosa*, or a combination thereof. The microorganism of the genus *Paracoccus* may be *P. versutus*. The microorganism of the genus *Escherichia* may be *E. coli*.

The recombinant microorganism may reduce a concentration of nitrous oxide in a sample containing nitrous oxide. The reduction may include conversion of $N_2O$ to $N_2$ or Fe(II)(L)-NO to $N_2$ by the nitrous oxide reductase. The sample may be in a liquid state or a gaseous state. The sample may be industrial wastewater or waste gas, or from another source. The sample may include a nitrogen oxide such as nitrous oxide. The nitrogen oxide may include $N_2O$, NO, $N_2O_3$, $NO_2$, $N_2O_4$, $N_2O_5$, or a combination thereof.

Another aspect of the present disclosure provides a composition for reducing a concentration of nitrous oxide in a sample, the composition including a recombinant microorganism including a foreign gene encoding a variant of a nitrous oxide reductase protein, wherein the variant includes an amino acid alteration of an amino acid residue corresponding to position H78 of the amino acid sequence of SEQ ID NO: 1 and has activity of an enzyme belonging to EC 1.7.2.4. Unless otherwise stated, the recombinant microorganism including a foreign gene encoding a variant of a nitrous oxide reductase protein or the variant of a nitrous oxide reductase protein is the same as described above.

The term "reduction" as used with respect to the composition refers to a reduction of a concentration of nitrous oxide present in a sample, and may include complete removal of nitrous oxide from the sample. The sample may be gas or liquid. The sample may not naturally include the recombinant microorganism. The composition may further include a substance that increases the solubility of nitrous oxide in a medium or a culture. The nitrous oxide may be in the form of Fe(II)(L)-NO.

The composition may be for use in reducing a concentration of nitrous oxide in a sample by contacting it with the sample. The contacting may be performed in a liquid phase. The contacting may be achieved by, for example, contacting the sample with a culture of a microorganism cultured in a culture medium. The culturing may be achieved under conditions for proliferating microorganisms. The contacting may be performed in a closed (i.e., sealed) container. The contacting may be performed under anaerobic conditions. The contacting may include culturing or incubating the recombinant microorganism while contacting it with the sample including nitrous oxide. The contacting may include culturing the recombinant microorganism under conditions for proliferating the recombinant microorganism in a closed container. The culture medium may be a chemically defined medium. The expression "chemically defined medium" as used herein refers to a culture medium supplemented with a known chemical composition. Such a chemically defined culture medium may not contain a complex component such as serum or hydrolysate. A liquid medium may include, for example, an LB medium, an M9 medium, a phosphate buffer, a Tris buffer, and the like. The medium may contain $Mg^{2+}$ ions in a concentration range of about 0.1 millimolar (mM) to about 7.5 mM, about 0.5 mM to about 7.5 mM, about 0.5 mM to about 5.0 mM, about 0.5 mM to about 2.5 mM, about 0.5 mM to about 1.5 mM, or about 1.0 mM to about 2.5 mM.

In the composition, the sample may be in a liquid state or a gaseous state. The sample may be industrial wastewater or waste gas.

Another aspect of the present disclosure provides a method of reducing a concentration of nitrous oxide in a sample that includes nitrous oxide, the method including contacting the sample with a recombinant microorganism, wherein the recombination microorganism includes a foreign gene encoding a variant of a nitrous oxide reductase protein; or with a variant of a nitrous oxide reductase protein to reduce a concentration of nitrous in the sample, wherein the variant includes an amino acid alteration of an amino acid residue corresponding to position H78 of the amino acid sequence of SEQ ID NO: 1 and has activity of an enzyme belonging to EC 1.7.2.4. Unless otherwise stated, the recombinant microorganism including a foreign gene encoding a variant of a nitrous oxide reductase protein or the variant of the nitrous oxide reductase protein is the same as described above.

In the method, the contacting may be performed in a liquid phase. The contacting may be achieved by, for example, contacting the sample with a culture of the recombinant microorganism cultured in a medium. The culture may be achieved under conditions for proliferating microorganisms. The contacting may be performed in a closed container. The medium may be a chemically defined medium. Such a chemically defined medium may not contain a composite component such as serum or hydrolysate. A liquid medium may include, for example, an LB medium, an M9 medium, a phosphate buffer, a Tris buffer, and the like. The medium may contain $Mg^{2+}$ ions in a concentration range of about 0.1 mM to about 7.5 mM, about 0.5 mM to about 7.5 mM, about 0.5 mM to about 5.0 mM, about 0.5 mM to about 2.5 mM, about 0.5 mM to about 1.5 mM, or about 1.0 mM to about 2.5 mM.

The contacting may be performed when the growth of the microorganism is at an exponential phase or a stationary phase. The culturing may be performed under anaerobic conditions. The contacting may be performed under conditions in which the recombinant microorganism is viable, for example in a closed container. The conditions in which the recombinant microorganism is viable may refer to conditions that allow the recombinant microorganism to proliferate or to remain in a proliferative state.

In the method, the sample may be in a liquid state or a gaseous state. The sample may be industrial wastewater or waste gas. The sample may include active contact as well as passive contact of the recombinant microorganism with the culture. The sample may be, for example, provided by sparging in a culture solution of the recombinant microorganism. That is, the sample may be blown through a medium or a culture solution. The sparging may be blowing from the bottom of a medium or a culture solution to the top. The sparging may be injecting droplets of the sample.

In the method, the contacting may be performed in a batch or in continuous manner. The contacting may include, for example, contacting the reduced i.e., contacted sample obtained in the reducing step with a fresh recombinant microorganism. Such contacting with the fresh recombinant microorganism may be performed at least twice, for example, twice, 3 times, 5 times, or 10 times, or more. The contacting with the fresh recombinant microorganism may be continued or repeated for a period of time until the desired reduced concentration of nitrous oxide in the sample is achieved.

Another aspect of the present disclosure provides a variant of a nitrous oxide reductase protein and a polynucleotide encoding the variant, wherein the variant includes an amino acid alteration of an amino acid residue corresponding to position H78 of the amino acid sequence of SEQ ID NO: 1 and has activity of an enzyme belonging to EC 1.7.2.4.

The amino acid alteration may be a substitution of the amino acid residue corresponding to the H78 position with A, M, N, E, P, F, I, or C. The amino acid alteration may be an H78A, H78M, H78N, H78E, H78P, H78F, H78I or H78C substitution.

The polynucleotide encoding the variant may be included in a vector. For use as the vector, any suitable material that is available to introduce a polynucleotide into a microorganism may be used. The vector may be a plasmid vector or a viral vector.

Another aspect of the present disclosure provides a method of preparing a recombinant microorganism, the method including introducing a polynucleotide encoding a variant of a nitrous oxide reductase protein, wherein the variant includes an amino acid alteration of an amino acid residue corresponding to position H78 of the amino acid sequence of SEQ ID NO: 1 and has activity of an enzyme belonging to EC 1.7.2.4. The introducing of the polynucleotide may include introducing a vehicle including the polynucleotide into a microorganism.

The recombinant microorganism may belong to the genus *Pseudomonas*, the genus *Paracoccus*, or the genus *Escherichia*. The microorganism of the genus *Pseudomonas* may be *P. stutzeri* or *P. aeruginosa*, or a combination thereof. The microorganism of the genus *Paracoccus* may be *P. versutus*. The microorganism of the genus *Escherichia* may be *E. coli*.

The recombinant microorganisms according to an aspect may be used to remove nitrous oxide from a sample including nitrous oxide. The composition according to another aspect may be used to reduce the concentration of nitrous oxide in the sample.

The method of reducing the concentration of nitrous oxide in a sample including nitrous oxide according to another aspect may be utilized to effectively reduce the concentration of nitrous oxide in the sample.

The variant of the nitrous oxide reductase protein and the polynucleotide encoding the variant according to another aspect may be used to remove nitrous oxide from the sample or may be used in the method of preparing a microorganism that expresses the variant of the nitrous oxide reductase protein.

Hereinafter, the present disclosure will be described in detail with reference to Examples below. However, these Examples are provided for illustrative purposes only, and the scope of the present disclosure is not limited thereto.

EXAMPLE 1

Recombinant *E. Coli* Expressing Nitrous Oxide Reductase and Variant Gene Thereof and Removal of Nitrous Oxide from a Sample Using the Recombinant *E. Coli*

In the present Example, recombinant *E. coli* expressing nitrous oxide reductase and a variant gene thereof was prepared, and an effect of removing nitrous oxide, i.e., $N_2O$ or Fe(EDTA)-NO, from a sample was confirmed using the recombinant *E. coli*.

(1) Preparation of Recombinant *E. Coli* Expressing Nitrous Oxide Reductase and Variant Gene Thereof From *Pseudomonas stutzeri* (ZoBell), which is a natural denitrification strain, a nosZ gene encoding nitrous oxide reductase (NosZ) that is a key enzyme, and auxiliary genes which are essential for the NosZ to have activity, such as nosR, nosD, nosF, nosY, and apbE genes, were extracted from a nos operon or gene cluster in the genome. The extracted genes were subjected to codon-optimization for *E. coli*, and then introduced thereto. Accordingly, by converting $N_2O$ to $N_2$, a recombinant microorganism of the genus Escherichia having $N_2$ producibility, that is, a recombinant *E. coli* was prepared. To determine whether the recombinant *E. coli* had $N_2$ producibility, the recombinant *E. coli* was cultured on a substrate labeled with a radioactive isotope $^{15}N$, that is, in the presence of $^{15}N_2O$ and FeEDTA-BNO. Then, the amount of $^{15}N_2$ in the culture or the upper air layer of the culture medium was measured.

In addition, in the amino acid sequence of nitrous oxide reductase of SEQ ID NO: 1, the wild-type nosZ gene was substituted with a gene encoding a variant of nitrous oxide reductase in which an amino acid residue at position H78 was substituted with one of 19 other natural amino acids. Then, it was tested in the same manner to determine whether *E. coli* including the variant gene had the $N_2$ producibility.

The function of each gene product (i.e., protein) of the genes was considered as follows. NosZ is a product of the nosZ gene, and is an enzyme that catalyzes the conversion of $N_2O$ to $N_2$. That is, NosZ is nitrous oxide reductase. NosZ may be a homodimeric metalloprotein of 130 kDa that contains two copper centers, CuA and CuZ, in each monomer. NosR may be encoded by the nosR gene, and may be a polytopic membrane protein serving as an electron donor for $N_2O$ reduction. NosD may be encoded by the nosD gene, and may be essential for the formation of [4Cu:2S] CuZ site. NosD may supply sulfur (S) to NosZ. NosF and NosY may be encoded by the nosF gene and the nosY gene, respectively, and may together form a complex, such as a tetramer, to serve as an ABC transporter. ApbE is a protein that may be encoded by the apbE gene, and may be a flavinyltransferase that transfers flavin to NosR.

2. Preparation of Vector and Preparation of Recombinant *E. Coli* Transformed with Prepared Vector (1) Preparation of Vector As expression vectors, pETDuet™-1 and pACYC-Duet™-1 vectors were used. The pETDuet™-1 vector was designed to operably link a lac operator to a T7 promoter, and contained an ampicillin resistance gene, $Amp^R$, as a selective marker. The pACYCDuet™-1 vector was designed to operably link a lac operator to a T7 promoter, and contained a chloramphenicol resistance gene, $Cm^R$, as a selective marker.

NosZ may be a polypeptide having at least 75% sequence identity with an amino acid sequence of SEQ ID NO: 1, 4, or 7. The nosZ gene may be a polynucleotide having at least 75% sequence identity with the nucleotide sequence of SEQ ID NO: 2, 3, 5, 6, 8, or 9.

NosR may be a polypeptide having at least 75% sequence identity to the amino acid sequence of SEQ ID NO: 10, 13, or 16. The nosZ gene may be a polynucleotide having at least 75% sequence identity with the nucleotide sequence of SEQ ID NO: 11, 12, 14, 15, 17, or 18.

NosD may be a polypeptide having at least 75% sequence identity to the amino acid sequence of SEQ ID NO: 19, 22, or 25. The nosD gene may be a polynucleotide having at least 75% sequence identity with the nucleotide sequence of SEQ ID NO: 20, 21, 23, 24, 26, or 27.

NosF may be a polypeptide having at least 75% sequence identity to the amino acid sequence of SEQ ID NO: 28, 31, or 34. The nosF gene may be a polynucleotide having at least 75% sequence identity with the nucleotide sequence of SEQ ID NO: 29, 30, 32, 33, 35, or 36.

NosY may be a polypeptide having at least 75% sequence identity to the amino acid sequence of SEQ ID NO: 37, 40, or 43. The nosY gene may be a polynucleotide having at least 75% sequence identity with the nucleotide sequence of SEQ ID NO: 38, 39, 41, 42, 44, or 45.

ApbE may be a polypeptide having at least 75% sequence identity with the amino acid sequence of SEQ ID NO: 46, 49, or 52. The apbE gene may be a polynucleotide having at least 75% sequence identity with the nucleotide sequence of SEQ ID NO: 47, 48, 50, 51, 53, or 54.

The origin and characteristics of the above-described proteins and the nucleotides encoding the same are set forth in the Sequence Listing. Among the genes used in the expression vector in *E. coli* in the present Example, nucleotide sequences of the native gene were optimized in consideration of the codon frequency used in *E. coli*, and information thereof is described in the sequence list.

FIG. 1 is a diagram of a vector introduced into *E. coli*. In FIG. 1, No. 1 and Nos. 2 to 20 each represent a pET-deut vector including the nosR gene and the nosZ gene or a variant of the nosZ gene. Nos. 2 to 20 each represent a vector including a variant gene substituted with 19 amino acids instead of the natural amino acid H at H78. Then, one of these vectors and a pPs_DFY_apbE vector including the nosD gene, the nosF gene, the nosF gene, and apbE gene were co-introduced into *E. coli*. The pPs_DFY_apbE vector is a vector prepared based on the pACYC-deut vector.

In each of the vectors numbered 1 to 20, the nosR gene and the nosZ gene or the variant of the nosZ gene were commonly operably linked to the T7 promoter in the pET-deut vector, and a ribosome binding site (RBS) included an *E. coli* RBS sequence, AAGGAG. Here, the nosZ gene included a sequence encoding a his-tag. In the pPs_DFY_apbE vector, the nosD gene, the nosF gene, and the nosY gene derived from *P. stutzeri* were operably linked to the T7 promoter in a pACYC-duet vector, and the apbE gene was operably linked to a different T7 promoter. Here, an RBS of each gene included an *E. coli* RBS sequence, AAGGAG.

(2) Preparation of Recombinant *E. Coli* Having $N_2$ Producibility and Confirmation of Activity Thereof Two vectors, i.e., one of the vectors numbered to 1 to 20 prepared in Section (1) and the pPs_DFY_apbE vector were introduced into *E. coli* C43 (DE3) by transformation to prepare recombinant *E. coli*. The transformation was performed by an electroporation method.

(2.1) NosZ Maturation Step Culture

The recombinant *E. coli* was cultured in 2×YT medium containing 50 micrograms per milliliter (ug/mL) of riboflavin and 0.25 mM of $CuCl_2$ in an Erlenmeyer flask until OD600 reached 0.6 while stirring at 230 revolutions per minute (rpm) at 37° C. Then, 1 mM of IPTG was added thereto and cultured overnight to induce gene expression while stirring at 140 rpm at 30° C. Next, cells were harvested and used for the subsequent $N_2$ production reaction.

(2.2) $N_2$ Production Culture from $^{15}N_2O$

The recombinant *E. coli* cells were added to M9 medium (pH 7.0) in a serum bottle containing 5 gram per liter (g/L) of glucose and 1.25 mM of $^{15}N_2(g)$, at a concentration of OD600 of 1 to prepare 30 mL of a culture mixture. The culture mixture was added to a 60 ml serum bottle, and then cultured while stirring at 30° C. at 140 rpm. The concentration of $^{15}N_2O$ (g) represents the concentration with respect to the volume of the space above the culture medium. A stopper was used to seal the bottle under anaerobic conditions. A control group was prepared in the same manner, except that *E. coli* including an empty vector was used. Next, the amount of $^{15}N_2$ produced was analyzed with GC-MS by sampling the gas in the headspace of the reaction serum bottle.

Figure 2:
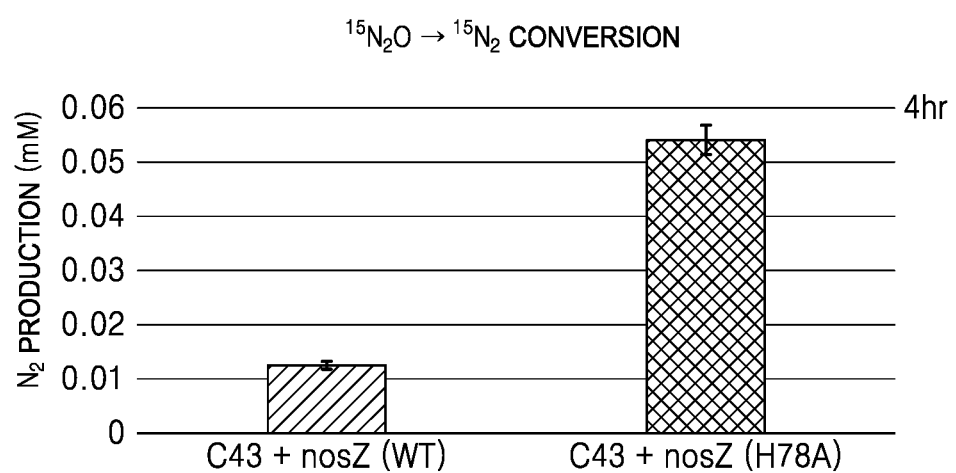
FIG. 2 is a diagram showing results of converting $N_2O$ to $N_2$ using recombinant *E. coli* including a wild-type nosZ gene and a variant of the nosZ gene.

The results are shown in FIG. 2. FIG. 2 is a bar graph showing the results of converting $N_2O$ to $N_2$ using the recombinant *E. coli* including the wild-type nosZ gene (left) and the variant of the nosZ gene (right).

As shown in FIG. 2, when recombinant *E. coli* including a variant gene, i.e., H78A, was used, the $N_2$ production was significantly increased after 4 hours, compared to *E. coli* BL31 (C43) including the vector including the wild-type nosZ gene. The *E. coli* BL31(C43) including the vector including the wild-type nosZ gene and the recombinant *E. coli* including the H78A variant gene produced 0.01262 mN of $N_2$ and 0.05415 mM of N2, respectively.

(2.3) $N_2$ Production Culture from Fe(II)EDTA-$^{15}$NO

The recombinant *E. coli* cells obtained in Section (2.1) were added to M9 medium (pH 7.0) containing 5 g/L of glucose and 1.25 mM Fe(II)EDTA-15NO until the OD600 of the culture reached 1, thereby obtaining a reaction mixture.

Next, 30 mL of the reaction mixture was added to a 60 mL serum bottle, and cultured while stirring at 30° C. at 140 rpm. The serum bottle was kept in an anaerobic chamber to be maintained under anaerobic conditions. A control group was prepared in the same manner, except that *E. coli* including the vector including the wild-type nosZ gene was used.

Next, the amount of $^{15}N_2$ produced was analyzed with GC-MS by sampling the gas in the headspace of the reaction serum bottle.

Figure 3:
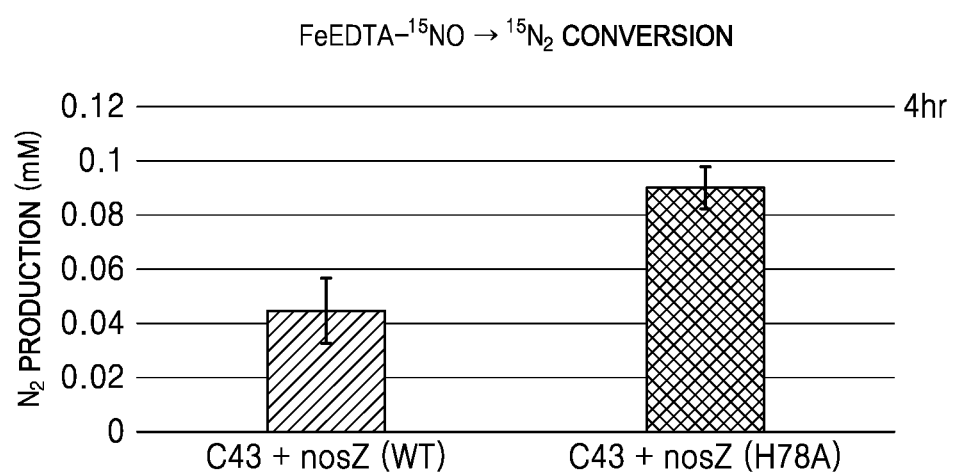
FIG. 3 is a diagram showing results of converting NO in the form of Fe(II)EDTA-$^{15}$NO to $N_2$ using recombinant *E. coli* including a wild-type nosZ gene and a variant of the nosZ gene.

The results are shown in FIG. 3. FIG. 3 is a bar graph showing results of converting NO in the form of Fe(II) EDTA-$^{15}$NO to $N_2$ using the recombinant *E. coli* including the wild-type nosZ gene (left) and the variant of the nosZ gene (right).

As shown in FIG. 3, when recombinant *E. coli* including a variant gene, i.e., H78A, was used, the $N_2$ production was significantly increased after 4 hours, compared to *E. coli* BL31 (C43) including the vector including the wild-type nosZ gene. The *E. coli* BL31(C43) including the vector including the wild-type nosZ gene and the recombinant *E. coli* including the H78A variant gene produced 0.04632 mN of $N_2$ and 0.09068 mM of N2, respectively.

EXAMPLE 2

Evaluation of In Vitro Activity of Recombinant Nitrous Reductase (NosZ) Variant

Recombinant *E. coli* C43 (DE3) including two vectors, i.e., one of the vectors numbered 1 to 20 and the pPs_DFY-_apbE vector, prepared in Example 1 was cultured, and a cell lysate was obtained from the culture and purified. Then, the activity of purified nitrous reductase (NosZ) was evaluated in vitro.

(1) NosZ Maturation Step Culture

The recombinant *E. coli* was cultured in 2×YT medium containing 50 ug/mL of riboflavin and 0.25 mM of $CuCl_2$ in an Erlenmeyer flask until a value of OD600 reached 0.6 while stirring at 230 rpm at 37° C. Then, 1 mM of IPTG was added thereto and cultured overnight to induce gene expression while stirred at 140 rpm at 30° C. Next, the recombinant *E. coli* was disrupted by sonication in a lysis buffer (containing 50 mM $NaH_2PO_4$, 300 mM of NaCl, and 10 mM of imidazole at pH 8.0). As a result, a cell lysate was obtained, and an Ni-NTA affinity column was used to purify the NosZ from the cell lysate by a general method using the following two buffers: Ni-NTA washing buffer (containing 50 mM of $NaH_2PO_4$, 300 mM of NaCl, and 20 mM of imidazole at pH 8.0); and Ni-NTA elution buffer (containing 50 mM of $NaH_2PO_4$ 300 mM of NaCl, and 250 mM of imidazole at pH 8.0). Afterwards, the purified NosZ was brought into contact with $N_2O$ for use in the $N_2$ production reaction.

(2) $N_2$ Production from $^{15}N_2O$ by Purified NosZ

An aqueous reaction solution was prepared by adding 0.2 mg/ml of the purified NosZ obtained in Section (1), 2.0 mM of benzyl viologen, 1.0 mM of sodium dithionite, and 1.25 mM of $^{15}N_2O$ (g) to water (pH 7.0). 30 mL of the aqueous reaction solution was added to a 60 mL serum bottle and cultured while stirring at 30° C. at 140 rpm. A stopper was used to seal the bottle under anaerobic conditions. A control group was prepared in the same manner, except that an aqueous solution containing bovine serum albumin (BSA) was used.

Next, the amount of $^{15}N_2$ produced was analyzed with GC-MS by sampling the gas in the headspace of the reaction serum bottle. The results are shown in Table 1, where umole/mg min is micromole per milligram per minute.

TABLE 1

| Name of NosZ variant | Activity of converting $N_2O$ to $N_2$ (umole/mg min) | Multiplication Δ (%) |
|---|---|---|
| His (wild-type) | 0.101121 | — |
| Ala | 0.586436 | 480.1 |
| Met | 0.3541 | 250.2 |
| Asn | 0.955317 | 844.9 |
| Lys | 0 | −100.0 |
| Asp | 0.084697 | −16.2 |
| Leu | 0.015912 | −84.3 |
| Glu | 0.110087 | 8.9 |
| Pro | 0.253231 | 150.5 |
| Phe | 0.285684 | 182.6 |
| Thr | 0.092062 | −8.9 |
| Tyr | 0 | −100.0 |
| Ile | 0.285777 | 182.7 |
| Cys | 0.814814 | 705.9 |

As shown in Table 1, compared to the wild-type H78, the variant H78A, H78M, H78N, H78E, H78P, H78F, H78I, or H78C had excellent activity of converting $N_2O$ to N2 in vitro.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A recombinant microorganism comprising a foreign gene encoding a nitrous oxide reductase enzyme, wherein the enzyme is nitrous oxide reductase NosZ having at least 85% amino acid sequence identity to SEQ ID NO: 1, and wherein the enzyme comprises an amino acid alteration of an amino acid residue corresponding to position H78 of the amino acid sequence of SEQ ID NO: 1, wherein the microorganism belongs to the genus *Escherichia*.

2. The microorganism of claim 1, wherein the amino acid alteration is a substitution of the amino acid residue corresponding to position H78 with A, M, N, E, P, F, I, or C.

3. The microorganism of claim 1, wherein the amino acid alteration is an H78A, H78M, H78N, H78E, H78P, H78F, H78I or H78C substitution.

4. The microorganism of claim 1, further comprising a genetic modification that increases expression of an auxiliary gene product required for NosZ enzyme activity as compared to the expression of the auxiliary gene product in the microorganism without the modification, wherein the auxiliary gene product—is a NosR encoded by a nitrous oxide reductase R (nosR) gene, NosD encoded by a nitrous oxide reductase D (nosD) gene, a encoded by a nitrous oxide reductase F (nosF) gene, a NosY encoded by a nitrous oxide reductase Y (nosY) gene, and a flavinyltransferase ApbE encoded by an apbE gene, or a combination thereof.

5. The microorganism of claim 1, wherein the microorganism is *Escherichia coli*.

6. A composition comprising a recombinant microorganism for reducing a concentration of nitrous oxide in a sample as compared to a sample without the recombinant microorganism, the recombinant microorganism comprising a foreign gene encoding a nitrous oxide reductase enzyme, wherein the enzyme is nitrous oxide reductase NosZ having at least a 85% amino acid sequence identity to SEQ ID NO: 1, and wherein the enzyme has an amino acid alteration of an amino acid residue corresponding to position H78 of the amino acid sequence of SEQ ID NO: 1, wherein the microorganism belongs to the genus *Escherichia*.

7. The composition of claim 6, wherein the amino acid alteration is a substitution of the amino acid residue corresponding to position H78 with A, M, N, E, P, F, I, or C.

8. The composition of claim 6, wherein the amino acid alteration is an H78A, H78M, H78N, H78E, H78P, H78F, H78I or H78C substitution.

9. The composition of claim 6, the microorganism further comprising a genetic modification that increases expression of an auxiliary gene product required for NosZ enzyme activity as compared to the expression of the auxiliary gene product without the genetic modification, wherein the auxiliary gene product is a NosR encoded by a nitrous oxide reductase R (nosR) gene, a NosD encoded by a nitrous oxide reductase D (nosD) gene, a NosF encoded by a nitrous oxide reductase F (nosF) gene, a NosY encoded by a nitrous oxide reductase Y (nosY) gene, and a flavinyltransferase ApbE encoded by an apbE gene.

10. The composition of claim 6, wherein the microorganism is *Escherichia coli*.

11. A polynucleotide encoding a nitrous oxide reductase enzyme, wherein the enzyme is nitrous oxide reductase NosZ having at least 85% amino acid sequence identity to SEQ ID NO: 1, and wherein the enzyme comprises an amino acid alteration of the amino acid residue corresponding to position H78 of the amino acid sequence of SEQ ID NO: 1 and the amino acid alteration is a substitution of the amino acid residue corresponding to position H78 with A, M, N, E, P, F, I, or C.

12. A method of reducing a concentration of nitrous oxide in a sample comprising nitrous oxide, the method comprising contacting a sample comprising nitrous oxide with a recombinant microorganism comprising a foreign gene encoding a nitrous oxide reductase protein, wherein the protein is nitrous oxide reductase NosZ having at least 85% amino acid sequence identity to SEQ ID NO:1, and—
wherein the enzyme comprises an amino acid alteration of an amino acid residue corresponding to position H78 of the amino acid sequence of SEQ ID NO: 1 wherein the microorganism belongs to the genus *Escherichia*.

13. The method of claim 12, wherein the amino acid alteration is a substitution of the amino acid residue corresponding to position H78 with A, M, N, E, P, F, I, or C.

14. The method of claim 12, wherein the amino acid alteration is an H78A, H78M, H78N, H78E, H78P, H78F, H78I or H78C substitution.

15. The method of claim 12, wherein the microorganism further comprises a genetic modification that increases expression of an auxiliary gene product required for NosZ activity as compared to the expression of the auxiliary gene product in the microorganism without the modification, wherein the auxiliary gene product is a NosR encoded by a nitrous oxide reductase R (nosR) gene, a NosD encoded by a nitrous oxide reductase D (nosD) gene, a NosF encoded by a nitrous oxide reductase F (nosF) gene, a NosY encoded by a nitrous oxide reductase Y (nosY) gene, a flavinyltransferase ApbE encoded by an apbE gene, or a combination thereof.

16. The method of claim 12, wherein the microorganism is *Escherichia coli*.

17. The method of claim 12, wherein the contacting is performed in a closed container.

18. The method of claim 12, wherein the contacting comprises culturing or incubating the recombinant microorganism while contacting the recombinant microorganism with the sample comprising nitrous oxide.

19. The method of claim 12, wherein the sample is industrial wastewater or waste gas.

* * * * *

SEQUENCE LISTING

<160> NUMBER OF SEQ ID NOS: 54

<210> SEQ ID NO 1
<211> LENGTH: 638
<212> TYPE: PRT
<213> ORGANISM: Pseudomonas stutzeri

<400> SEQUENCE: 1

Met Ser Asp Lys Asp Ser Lys Asn Thr Pro Gln Val Pro Glu Lys Leu
1               5                   10                  15

Gly Leu Ser Arg Arg Gly Phe Leu Gly Ala Ser Ala Val Thr Gly Ala
            20                  25                  30

```
Ala Val Ala Ala Thr Ala Leu Gly Gly Ala Val Met Thr Arg Glu Ser
         35                  40                  45

Trp Ala Gln Ala Val Lys Glu Ser Lys Gln Lys Ile His Val Gly Pro
 50                  55                  60

Gly Glu Leu Asp Asp Tyr Tyr Gly Phe Trp Ser Gly His Gln Gly
 65                  70                  75                  80

Glu Val Arg Val Leu Gly Val Pro Ser Met Arg Glu Leu Met Arg Ile
                 85                  90                  95

Pro Val Phe Asn Val Asp Ser Ala Thr Gly Trp Gly Leu Thr Asn Glu
                100                 105                 110

Ser Arg His Ile Met Gly Asp Ser Ala Lys Phe Leu Asn Gly Asp Cys
            115                 120                 125

His His Pro His Ile Ser Met Thr Asp Gly Lys Tyr Asp Gly Lys Tyr
            130                 135                 140

Leu Phe Ile Asn Asp Lys Ala Asn Ser Arg Val Ala Arg Ile Arg Leu
145                 150                 155                 160

Asp Ile Met Lys Cys Asp Lys Met Ile Thr Val Pro Asn Val Gln Ala
                165                 170                 175

Ile His Gly Leu Arg Leu Gln Lys Val Pro His Thr Lys Tyr Val Phe
            180                 185                 190

Ala Asn Ala Glu Phe Ile Ile Pro His Pro Asn Asp Gly Lys Val Phe
            195                 200                 205

Asp Leu Gln Asp Glu Asn Ser Tyr Thr Met Tyr Asn Ala Ile Asp Ala
            210                 215                 220

Glu Thr Met Glu Met Ala Phe Gln Val Ile Val Asp Gly Asn Leu Asp
225                 230                 235                 240

Asn Thr Asp Ala Asp Tyr Thr Gly Arg Phe Ala Ala Ala Thr Cys Tyr
                245                 250                 255

Asn Ser Glu Lys Ala Phe Asp Leu Gly Gly Met Met Arg Asn Glu Arg
            260                 265                 270

Asp Trp Val Val Phe Asp Ile His Ala Val Glu Ala Ala Val Lys
            275                 280                 285

Ala Gly Asp Phe Ile Thr Leu Gly Asp Ser Lys Thr Pro Val Leu Asp
            290                 295                 300

Gly Arg Lys Lys Asp Gly Lys Asp Ser Lys Phe Thr Arg Tyr Val Pro
305                 310                 315                 320

Val Pro Lys Asn Pro His Gly Cys Asn Thr Ser Ser Asp Gly Lys Tyr
                325                 330                 335

Phe Ile Ala Ala Gly Lys Leu Ser Pro Thr Cys Ser Met Ile Ala Ile
            340                 345                 350

Asp Lys Leu Pro Asp Leu Phe Ala Gly Lys Leu Ala Asp Pro Arg Asp
            355                 360                 365

Val Ile Val Gly Glu Pro Glu Leu Gly Leu Gly Pro Leu His Thr Thr
            370                 375                 380

Phe Asp Gly Arg Gly Asn Ala Tyr Thr Thr Leu Phe Ile Asp Ser Gln
385                 390                 395                 400

Val Val Lys Trp Asn Met Glu Glu Ala Val Arg Ala Tyr Lys Gly Glu
                405                 410                 415

Lys Val Asn Tyr Ile Lys Gln Lys Leu Asp Val His Tyr Gln Pro Gly
            420                 425                 430

His Leu His Ala Ser Leu Cys Glu Thr Asn Glu Ala Asp Gly Lys Trp
            435                 440                 445
```

```
Leu Val Ala Leu Ser Lys Phe Ser Lys Asp Arg Phe Leu Pro Val Gly
            450                 455                 460
Pro Leu His Pro Glu Asn Asp Gln Leu Ile Asp Ile Ser Gly Asp Glu
465                 470                 475                 480
Met Lys Leu Val His Asp Gly Pro Thr Phe Ala Glu Pro His Asp Cys
                485                 490                 495
Ile Met Ala Arg Arg Asp Gln Ile Lys Thr Lys Ile Trp Asp Arg
            500                 505                 510
Asn Asp Pro Phe Phe Ala Pro Thr Val Glu Met Ala Lys Lys Asp Gly
            515                 520                 525
Ile Asn Leu Asp Thr Asp Asn Lys Val Ile Arg Asp Gly Asn Lys Val
530                 535                 540
Arg Val Tyr Met Thr Ser Met Ala Pro Ala Phe Gly Val Gln Glu Phe
545                 550                 555                 560
Thr Val Lys Gln Gly Asp Glu Val Thr Val Thr Ile Thr Asn Ile Asp
                565                 570                 575
Gln Ile Glu Asp Val Ser His Gly Phe Val Val Asn His Gly Val
            580                 585                 590
Ser Met Glu Ile Ser Pro Gln Gln Thr Ser Ser Ile Thr Phe Val Ala
            595                 600                 605
Asp Lys Pro Gly Leu His Trp Tyr Tyr Cys Ser Trp Phe Cys His Ala
610                 615                 620
Leu His Met Glu Met Val Gly Arg Met Met Val Glu Pro Ala
625                 630                 635
```

<210> SEQ ID NO 2
<211> LENGTH: 1917
<212> TYPE: DNA
<213> ORGANISM: Pseudomonas stutzeri

<400> SEQUENCE: 2

```
atgagcgaca aagattccaa gaacactccg caagtgcccg agaaactcgg cctgagccgc      60
cgcggcttcc tcggcgccag cgcagtcacc ggtgccgccg ttgctgccac ggctctcggc     120
ggcgcggtga tgacccgcga atcctgggcg caggccgtca aggagtccaa gcagaagatc     180
cacgtcggcc ccggcgagct ggatgactac tacggcttct ggtccggcgg tcaccagggt     240
gaagtccgcg tgctgggcgt gccgtcgatg cgcgagctga tgcgtatccc ggtgttcaac     300
gtcgactcgg ccaccggctg ggggctgacc aacgaaagcc gccacatcat gggcgacagc     360
gccaagttcc tcaacggtga ctgccaccac ccgcacatct ccatgaccga cggcaagtac     420
gatggcaagt acctgttcat caacgacaag gccaacagcc gcgttgcgcg tatccgtctg     480
gacatcatga gtgcgacaa gatgatcacc gtgccgaacg tgcaggcgat ccacggtctg     540
cgtctgcaga aggtgccgca caccaagtac gtattcgcca acgccgagtt catcatcccg     600
cacccgaacg atggcaaggt cttcgatctg caggacgaga acagctacac catgtacaac     660
gccatcgatg cggaaaccat ggaaatggcc ttccaggtca tcgttgacgg caacctcgac     720
aacaccgacg ccgactacac tggccgtttc gctgctgcta cctgctacaa ctcggagaag     780
gccttcgatc tgggcggcat gatgcgtaac gagcgcgact gggtggtggt gttcgatatc     840
cacgccgtcg aagcagcggt caaagctggc gatttcatca ccctgggcga ctccaagacg     900
cctgtgctcg atggtcgcaa gaaggatggc aaggacagca gttcacccg ttacgtgcca     960
gtgccgaaaa acccgcacgg ctgcaacacc tcctccgatg caaatactt catcgccgcc    1020
ggcaagctct cgccaaccctg ctcgatgatc gccatcgaca agctgcccga cctgttcgcc    1080
```

```
ggcaagctgg ccgatccgcg tgatgtgatc gtgggtgagc ctgagctggg tctcggcccg    1140
ctgcacacca ccttcgacgg ccgcggtaac gcctacacca cgctgttcat cgacagccag    1200
gtggtcaagt ggaacatgga agaagctgtt cgtgcctaca agggcgagaa ggtcaactac    1260
atcaagcaga agcttgatgt gcactaccag ccgggtcacc tgcacgcgtc gctgtgtgaa    1320
accaatgaag ccgatggcaa gtggctggta gcactgtcca agttctccaa ggaccgcttc    1380
ctgccggttg cccgctgca tcccgagaac gaccaactga tcgacatctc cggcgacgag    1440
atgaagctgg tacatgacgg cccgaccttt gccgaaccgc atgactgcat catggctcgc    1500
cgtgatcaga tcaagaccaa gaagatctgg gaccgcaacg atccgttctt cgccccgacc    1560
gtggaaatgg cgaagaagga cggcatcaac ctcgataccg acaacaaggt cattcgcgac    1620
ggcaacaagg tgcgcgtgta catgacctcg atggcgccgg cgttcggcgt gcaggagttc    1680
accgtcaagc agggcgatga agtcaccgtg accatcacca acatcgacca gatcgaagac    1740
gtctcccacg gcttcgtggt ggtcaaccat ggcgtgagca tggagatcag cccgcagcag    1800
acttcttcca tcacctttgt cgctgacaag ccaggcctgc actggtacta ctgcagctgg    1860
ttctgccatg cgctgcacat ggaaatggtc ggccgcatga tggtcgagcc ggcctaa       1917

<210> SEQ ID NO 3
<211> LENGTH: 1917
<212> TYPE: DNA
<213> ORGANISM: Artificial
<220> FEATURE:
<223> OTHER INFORMATION: Codon optimized NosZ gene

<400> SEQUENCE: 3
atgtccgaca aagacagcaa aaatacgcca caggtccctg agaagcttgg gttgtcgcgg     60
cgcggctttt taggggcgag cgcagttaca ggtgctgctg tagcagcgac agctctcggc    120
ggtgctgtca tgacccgcga gtcgtgggct caggccgtga agagtctaa gcagaaaatc     180 catgttgggc caggggaact cgatgattac tacggcttct ggtcgggtgg gcatcagggg    240
gaagtccgtg ttctgggcgt ccctagtatg cgtgaactca tgcggattcc tgtattcaac    300
gtcgactcag ccacaggttg gggcctcaca aatgaaagcc gtcacattat gggtgattcc    360
gcaaagttcc tcaatggcga ttgtcatcat ccacacatct cgatgactga cggcaaatat    420
gatggtaaat acttatttat taatgacaag gccaatagtc gggttgcacg gattcgcctc    480
gatattatga agtgcgataa aatgattaca gtcccaaacg tacaggctat ccatggcctc    540
cggcttcaaa aggtaccgca tacaaagtac gtcttcgcga acgcggaatt catcattcct    600
catccaaatg acggcaaggt cttcgattta caagacgaga attcctatac gatgtacaat    660
gcgattgaca cagaaacaat ggaaatggcc tttcaggtga ttgtcgatgg gaacttagac    720
aacacagacg ccgactatac tggtcggttc gcagcagcta catgttacaa ctctgagaaa    780
gcctttgacc ttggtggtat gatgcggaat gagcgtgact gggtcgttgt attcgacatt    840
catgctgtag aagctgcagt taaagccggc gactttatta cgttaggcga ttctaaaacg    900
ccagtgttgg acggccgcaa gaaggatggt aaggactcca gttcacgcg ctacgtgcct    960 gtgccaaaaa acccacatgg ttgcaatact tcgagtgacg gtaagtattt catcgcagct   1020
gggaaactca gcccgacatg ctctatgatt gcgattgata aacttccgga cctgttcgct   1080
gggaaactcg cggatccacg tgatgtgatt gttggtgagc cagaacttgg gctgggtcct   1140
ctgcacacta cgtttgacgg gcgcgggaat gcctacacaa cactgtttat cgactcccaa   1200
```

-continued

```
gttgtgaagt ggaacatgga agaagcggtt cgtgcttaca aaggggagaa ggttaattat   1260
attaaacaga agcttgacgt ccattatcaa ccggggcatc tccatgcttc gttgtgtgag   1320
acgaacgaag cagatggtaa atggctggtg gctttatcta aattttcgaa ggaccgtttc   1380
ctgccagttg gtcctctcca cccggagaac gaccagttaa tcgacatcag cggggacgaa   1440
atgaagctgg tgcacgacgg ccctacgttt gcggaacctc acgactgtat tatggcacgt   1500
cgggaccaaa ttaaaacgaa gaaaatctgg gatcgcaatg acccgttttt tgcacctacg   1560
gtcgagatgg caaaaaagga tggtatcaac ttggataccg ataacaaggt gatccgggat   1620
gggaataaag ttcgcgtgta catgactagt atggcacctg cctttgggt tcaggaattc    1680
accgtgaaac aaggtgacga agttaccgtt acgattacaa atatcgatca aattgaggac   1740
gtcagtcacg gttttgtcgt agtcaatcac ggtgtatcaa tggaaatctc accacaacag   1800
acatcttcca ttacgtttgt cgccgacaaa ccggggttac attggtacta ttgtagctgg   1860
ttctgccatg cccttcatat ggagatggta ggtcgcatga tggtagaacc agcatga      1917
```

<210> SEQ ID NO 4
<211> LENGTH: 636
<212> TYPE: PRT
<213> ORGANISM: Pseudomonas aeruginosa

<400> SEQUENCE: 4

```
Met Ser Asp Asp Thr Lys Ser Pro His Glu Glu Thr His Gly Leu Asn
1               5                   10                  15

Arg Arg Gly Phe Leu Gly Ala Ser Ala Leu Thr Gly Ala Ala Ala Leu
            20                  25                  30

Val Gly Ala Ser Ala Leu Gly Ser Ala Val Val Gly Arg Glu Ala Arg
        35                  40                  45

Ala Ala Gly Lys Gly Glu Arg Ser Lys Ala Glu Val Ala Pro Gly Glu
    50                  55                  60

Leu Asp Glu Tyr Tyr Gly Phe Trp Ser Gly His Ser Gly Glu Val
65              70                  75                  80

Arg Val Leu Gly Val Pro Ser Met Arg Glu Leu Met Arg Ile Pro Val
            85                  90                  95

Phe Asn Val Asp Ser Ala Thr Gly Trp Gly Leu Thr Asn Glu Ser Lys
        100                 105                 110

Arg Val Leu Gly Asp Ser Ala Arg Phe Leu Asn Gly Asp Cys His His
    115                 120                 125

Pro His Ile Ser Met Thr Asp Gly Lys Tyr Asp Gly Lys Tyr Leu Phe
130                 135                 140

Ile Asn Asp Lys Ala Asn Ser Arg Val Ala Arg Ile Arg Leu Asp Val
145             150                 155                 160

Met Lys Cys Asp Arg Ile Val Thr Ile Pro Asn Val Gln Ala Ile His
            165                 170                 175

Gly Leu Arg Leu Gln Lys Val Pro His Thr Arg Tyr Val Phe Cys Asn
        180                 185                 190

Ala Glu Phe Ile Ile Pro His Pro Asn Asp Gly Ser Thr Phe Asp Leu
    195                 200                 205

Ser Gly Asp Asn Ala Phe Thr Leu Tyr Asn Ala Ile Asp Ala Glu Thr
    210                 215                 220

Met Glu Val Ala Trp Gln Val Ile Val Asp Gly Asn Leu Asp Asn Thr
225             230                 235                 240

Asp Met Asp Tyr Ser Gly Arg Phe Ala Ala Ser Thr Cys Tyr Asn Ser
            245                 250                 255
```

Glu Lys Ala Val Asp Leu Gly Gly Met Met Arg Asn Glu Arg Asp Trp
            260                 265                 270

Val Val Val Phe Asp Ile Pro Arg Ile Glu Ala Glu Ile Lys Ala Lys
        275                 280                 285

Arg Phe Val Thr Leu Gly Asp Ser Lys Val Pro Val Val Asp Gly Arg
    290                 295                 300

Arg Lys Asp Gly Lys Asp Ser Pro Val Thr Arg Tyr Ile Pro Val Pro
305                 310                 315                 320

Lys Asn Pro His Gly Leu Asn Thr Ser Pro Asp Gly Lys Tyr Phe Ile
                325                 330                 335

Ala Asn Gly Lys Leu Ser Pro Thr Cys Thr Met Ile Ala Ile Glu Arg
            340                 345                 350

Leu Gly Asp Leu Phe Ala Gly Lys Leu Ala Asp Pro Arg Asp Val Val
        355                 360                 365

Val Gly Glu Pro Glu Leu Gly Leu Gly Pro Leu His Thr Thr Phe Asp
    370                 375                 380

Gly Arg Gly Asn Ala Tyr Thr Thr Leu Phe Ile Asp Ser Gln Leu Val
385                 390                 395                 400

Lys Trp Asn Leu Ala Asp Ala Val Arg Ala Tyr Lys Gly Glu Lys Val
                405                 410                 415

Asp Tyr Ile Arg Gln Lys Leu Asp Val Gln Tyr Gln Pro Gly His Asn
            420                 425                 430

His Ala Thr Leu Cys Glu Thr Ser Glu Ala Asp Gly Lys Trp Ile Val
        435                 440                 445

Val Leu Ser Lys Phe Ser Lys Asp Arg Phe Leu Pro Thr Gly Pro Leu
    450                 455                 460

His Pro Glu Asn Asp Gln Leu Ile Asp Ile Ser Gly Glu Glu Met Lys
465                 470                 475                 480

Leu Val His Asp Gly Pro Thr Phe Ala Glu Pro His Asp Cys Ile Leu
                485                 490                 495

Ala Arg Arg Asp Gln Ile Lys Thr Arg Lys Ile Trp Asp Arg Lys Asp
            500                 505                 510

Pro Phe Phe Ala Glu Thr Val Lys Arg Ala Lys Asp Gly Ile Asp
        515                 520                 525

Leu Met Lys Asp Asn Lys Val Ile Arg Glu Gly Asn Lys Val Arg Val
    530                 535                 540

Tyr Met Val Ser Met Ala Pro Ser Phe Gly Leu Thr Glu Phe Lys Val
545                 550                 555                 560

Lys Gln Gly Asp Glu Val Thr Val Thr Ile Thr Asn Leu Asp Glu Ile
                565                 570                 575

Glu Asp Val Thr His Gly Phe Val Met Val Asn His Gly Val Cys Met
            580                 585                 590

Glu Ile Ser Pro Gln Gln Thr Ser Ser Ile Thr Phe Val Ala Asp Lys
        595                 600                 605

Pro Gly Val His Trp Tyr Tyr Cys Ser Trp Phe Cys His Ala Leu His
    610                 615                 620

Met Glu Met Cys Gly Arg Met Leu Val Glu Lys Ala
625                 630                 635

<210> SEQ ID NO 5
<211> LENGTH: 1911
<212> TYPE: DNA
<213> ORGANISM: Pseudomonas aeruginosa

<400> SEQUENCE: 5

```
atgagcgacg acacgaaaag cccccacgaa gaaacccacg gcctgaaccg ccgcggcttc      60
ctcggcgcct cggcgctgac cggagccgcc gccctggttg gcgccagcgc cctgggcagc     120
gcggtggtcg gccgcgaggc ccgggccgcg ggcaagggcg agcgcagcaa ggccgaggtc     180
gcccccggcg aactggatga gtactacggg ttctggagcg gcggacattc cggcgaagta     240
cgcgtgctcg gcgtgccgtc gatgcgcgag ctgatgcgca taccggtgtt caacgtcgac     300
tcggccaccg gctggggcct gaccaacgag agcaagcggg tcctcggcga cagcgcgcgc     360
ttcctcaacg gcgactgcca ccatccgcac atctcgatga ccgacggcaa gtacgacggc     420
aagtacctgt tcatcaacga caaggccaac agccgggtcg cgcgcatccg cctggacgtc     480
atgaaatgcg accgcatcgt caccattccc aacgtccagg cgatccacgg cctgcgcctg     540
caaaaggtgc gcatacccg ctacgtgttc tgcaacgccg agttcatcat cccccatccc     600
aacgacggct cgaccttcga cctgtccggc gacaacgcct tcaccctgta caacgccatc     660
gacgccgaga ccatggaagt ggcctggcag gtgatcgtcg acggcaacct cgacaacacc     720
gacatggact acagcggcag gttcgccgcc tccacctgct acaactcgga aaaggccgtc     780
gacctcggcg catgatgcg caacgagcgc gactgggtgg tggtgttcga catcccgcgc     840
atcgaggccg agatcaaggc gaagcgcttc gtcaccctcg gcgactcgaa ggtgccggtg     900
gtcgacggcc ggcgcaagga cggcaaggac agcccggtga cccgctacat cccggtaccg     960
aagaaccccc acgggctgaa cacctcgccg gacggcaagt acttcatcgc caacggcaag    1020
ctctcgccga cctgcaccat gatcgccatc gagcgcctcg gcgacctgtt cgccggcaag    1080
ctggccgacc cgcgcgacgt ggtggtgggc gagccggaac tgggcctcgg cccgctgcac    1140
accactttcg atggccgagg caacgccat accacgctgt catcgacag ccagttggtg    1200
aagtggaacc tcgccgacgc ggtgcgcgcc tacaagggcg agaaggtcga ctacatccgc    1260
cagaagctcg acgtgcagta ccagccgggg cacaaccacg ccactctgtg cgagaccagc    1320
gaagccgacg gcaagtggat cgtggtgctc agcaagttct ccaaggaccg cttcctgccc    1380
accggtccgc tgcaccccga gaacgaccag ttgatcgaca tttccggcga ggaaatgaag    1440
ctggtccacg acggcccgac cttcgccgaa ccgcacgatt gcatcctcgc ccgccgcgac    1500
cagatcaaga cccgcaagat ctgggaccgc aaggacccgt tcttcgccga acggtcaag    1560
cgcgcggaaa aggacggcat cgacctgatg aaggacaaca aggtcatccg cgagggcaac    1620
aaggtccgcg tctacatggt ctcgatggcc ccctccttcg gcctcaccga gttcaaggtg    1680
aagcagggcg acgaagtcac cgtgaccatc accaacctcg acgagatcga ggacgtgacc    1740
cacggcttcg tcatggtcaa ccacggcgtc tgcatggaga tcagcccgca acagaccctcg   1800
tcgatcacct tcgtcgccga taagcccggg gtgcactggt actactgcag ctggttctgc    1860
cacgccctgc acatggaaat gtgcgggcgg atgctggtgg aaaaggcttg a             1911
```

<210> SEQ ID NO 6
<211> LENGTH: 1911
<212> TYPE: DNA
<213> ORGANISM: Artificial
<220> FEATURE:
<223> OTHER INFORMATION: Codon optimized NosZ gene

<400> SEQUENCE: 6

```
atgtccgatg ataccaaatc cccgcacgag gagactcatg ggctcaatcg ccggggtttt      60
ctcggtgctt ctgctctcac cggcgcggca gctcttgtag gggcatctgc cttgggttca     120
```

-continued

```
gctgtcgttg gcgggaagc tcgggctgct gggaagggcg aacgttctaa ggctgaagtc    180
gcgccagggg aacttgacga gtattatggc ttctggtcgg gtggtcattc gggcgaggta    240
cgggttttgg gcgtaccatc catgcgtgaa ctcatgcgga ttcctgtgtt caatgtggat    300
agtgcaacag gttgggggtt gactaatgaa tcgaagcgcg tccttgggga ttcagcccgt    360
ttcttaaacg gggattgcca tcatcctcat atcagcatga ccgatggcaa atacgatggc    420
aaatatttgt ttatcaatga taaagcgaac tcacgggtag cacgtatccg tctggatgtt    480
atgaagtgtg accgtattgt cacaattcca aacgtccaag ccattcacgg cctccggttg    540
cagaaggtgc cgcatacacg ctacgtattt tgtaatgccg agtttattat tccacaccca    600
aacgatggct ctacctttga tttaagcggg acaacgcgt tcaccctgta caacgcaatc     660
gatgctgaaa ctatggaagt tgcttggcag gttatcgtgg atgggaactt agataacacc    720
gacatggatt actctgggcg cttcgccgcg tcgacttgtt acaattctga aaaggcagtg    780
gacctgggtg gatgatgcg gaacgagcgc gactgggtag tcgtcttcga cattccgcgt    840
attgaggccg agatcaaggc gaaacggttt gtaacactcg gggattcaaa agttccagtt    900
gtagatggtc gccgtaagga cggcaaagac agccctgtta cgcgctatat cccagtacct    960
aaaaacccgc acggtctcaa caccagtcct gatggcaagt actttatcgc gaatggtaaa   1020 ctgtcacccta catgcaccat gattgcaatc gaacgtttag gtgatttgtt tgctgggaag   1080
cttgccgacc cacgtgatgt ggtagtaggc gaaccagagc tcgggctggg gccgctccat   1140
accacgtttg atggtcgggg taatgcgtat actaccttat tcatcgactc gcagttagtg   1200
aagtggaact agctgacgc agtacgggcc tacaagggcg aaaaagttga ctatattcgt    1260
caaaagttag acgtacagta ccagccgggc cacaatcacg caacgttatg tgaaacttct   1320
gaagcagatg ggaagtggat cgtagttctg tccaaatttt caaagatcg ctttctccct    1380 acaggtccat tacatccaga aaatgatcaa cttatcgaca tttcggggga agagatgaaa   1440
ctggtacacg atggtcctac attcgcggaa ccacacgatt gtatcctcgc gcggcgtgat   1500
cagattaaga ctcgcaagat ttgggaccgg aaggatccgt ttttcgctga gactgtgaag   1560
cgtgccgaaa aggatggcat cgaccttatg aaggacaata aggtaatccg cgaggggaac   1620
aaagtacgcg tctacatggt ttcaatggca ccttctttcg ggctcaccga atttaaagta   1680
aaacaaggcg atgaggtgac ggttactatt acaaatttag acgaaatcga agacgtgacg   1740
cacggttttg tgatggtgaa ccatggggta tgcatggaga tttcgccaca caaaacttct   1800
tctatcacgt ttgtcgctga taaaccaggc gtacattggt actattgtag ttggttctgt   1860
catgctttac acatggagat gtgcggtcgg atgctggtgg agaaggcttg a            1911
```

<210> SEQ ID NO 7
<211> LENGTH: 653
<212> TYPE: PRT
<213> ORGANISM: Pseudomonas versutus

<400> SEQUENCE: 7

```
Met Glu Thr Lys Gln Gln Asn Gly Leu Ser Arg Arg Ala Leu Leu Gly
1               5                   10                  15

Ala Thr Ala Gly Gly Ala Ala Met Ala Gly Ala Phe Gly Gly Arg Leu
            20                  25                  30

Ala Leu Gly Pro Ala Val Ile Gly Ala Gly Ala Ala Gly Val Ala Thr
        35                  40                  45
```

-continued

```
Ala Ala Gly Ser Gly Ala Ala Leu Ala Ala Ser Gly Asp Gly Ala Val
     50                  55                  60
Ala Pro Gly Gln Leu Asp Asp Tyr Tyr Gly Phe Trp Ser Ser Gly Gln
 65                  70                  75                  80
Thr Gly Glu Leu Arg Ile Leu Gly Val Pro Ser Met Arg Glu Leu Met
                     85                  90                  95
Arg Val Pro Val Phe Asn Arg Cys Ser Ala Thr Gly Trp Gly Ile Thr
                100                 105                 110
Asn Glu Ser Ile Leu Ile His Glu Arg Thr Met Ser Glu Arg Thr Arg
            115                 120                 125
Lys His Leu Ala Ala Asn Gly Lys Arg Ile His Asp Asn Gly Asp Leu
        130                 135                 140
His His Val His Met Ser Phe Thr Glu Gly Lys Tyr Asp Gly Arg Phe
145                 150                 155                 160
Leu Phe Met Asn Asp Lys Ala Asn Thr Arg Val Ala Arg Val Arg Cys
                165                 170                 175
Asp Val Met Lys Cys Asp Ala Ile Leu Glu Val Pro Asn Ala Lys Ala
                180                 185                 190
Ile His Gly Leu Arg Pro Gln Lys Trp Pro Arg Ser Asn Tyr Val Phe
            195                 200                 205
Cys Asn Gly Glu Asp Glu Ala Pro Leu Ile Asn Asp Gly Thr Thr Met
        210                 215                 220
Asp Asp Ile Ser Thr Tyr Val Asn Val Phe Thr Ala Val Asp Ala Asp
225                 230                 235                 240
Lys Trp Glu Val Ala Trp Gln Val Leu Val Ser Gly Asn Leu Asp Asn
                245                 250                 255
Cys Asp Ala Asp Tyr Glu Gly Lys Trp Ala Phe Ser Thr Ser Tyr Asn
                260                 265                 270
Ser Glu Met Gly Met Thr Leu Pro Glu Met Thr Glu Ala Glu Met Asp
            275                 280                 285
His Val Val Phe Asn Ile Ala Glu Ile Glu Lys Ala Ile Glu Ala
        290                 295                 300
Gly Asn Phe Glu Glu Ile Asn Gly Cys Lys Val Leu Asp Gly Arg Lys
305                 310                 315                 320
Glu Ala Asn Ser Gln Phe Thr Arg Tyr Ile Pro Ile Ala Asn Asn Pro
                325                 330                 335
His Gly Cys Asn Met Ala Pro Asp Lys Lys His Leu Val Val Ala Gly
            340                 345                 350
Lys Leu Ser Pro Thr Val Thr Val Leu Asp Val Thr Arg Phe Asp Ala
        355                 360                 365
Val Phe Asn Glu Asn Ala Asp Pro Arg Ser Ala Val Val Ala Glu Pro
    370                 375                 380
Glu Leu Gly Leu Gly Pro Leu His Thr Ala Phe Asp Gly Arg Gly Asn
385                 390                 395                 400
Ala Tyr Thr Ser Leu Phe Leu Asp Ser Gln Val Val Lys Trp Asn Ile
                405                 410                 415
Glu Glu Ala Ile Arg Ala Tyr Ala Gly Glu Gln Val Asp Pro Ile Lys
            420                 425                 430
Asp Lys Ile Asp Val His Tyr Gln Pro Gly His Leu Lys Thr Val Met
        435                 440                 445
Gly Glu Thr Leu Asp Ala Ser Asn Asp Trp Met Val Cys Leu Ser Lys
450                 455                 460
```

```
Phe Ser Lys Asp Arg Phe Leu Asn Val Gly Pro Leu Lys Pro Glu Asn
465                 470                 475                 480

Asp Gln Leu Ile Asp Ile Ser Gly Asp Lys Met Val Leu Val His Asp
                485                 490                 495

Gly Pro Thr Phe Ala Glu Pro His Asp Ala Ile Ala Val His Pro Ser
            500                 505                 510

Ile Met Ser Ser Val Ile Lys Ser Val Trp Asp Arg Asn Asp Pro Met
            515                 520                 525

Trp Ala Glu Thr Arg Lys Gln Ala Glu Ala Asp Gly Val Asn Ile Asp
            530                 535                 540

Glu Trp Thr Asp Gln Ile Ile Arg Asp Gly Asn Lys Val Arg Val Tyr
545                 550                 555                 560

Met Ser Ser Val Ala Pro Ser Phe Ser Val Glu Ser Phe Thr Val Thr
                565                 570                 575

Glu Gly Asp Glu Val Thr Val Ile Val Thr Asn Leu Asp Glu Ile Asp
            580                 585                 590

Asp Leu Thr His Gly Phe Thr Met Gly Asn His Gly Val Ala Met Glu
            595                 600                 605

Ile Ser Pro Gln Gln Thr Ser Ser Val Thr Phe Val Ala Ala Asn Pro
610                 615                 620

Gly Val Tyr Trp Tyr Tyr Cys Gln Trp Phe Cys His Ala Leu His Met
625                 630                 635                 640

Glu Met Arg Gly Arg Met Met Val Glu Pro Lys Ala Ala
                645                 650

<210> SEQ ID NO 8
<211> LENGTH: 1962
<212> TYPE: DNA
<213> ORGANISM: Pseudomonas versutus

<400> SEQUENCE: 8
atggaaacca acagcaaaa cggcctgagc cgccgcgcgc ttctgggcgc gaccgccggc      60
ggtgcggcca tggccggcgc gttcgggggg cgcctggcgc tgggaccggc cgtgatcggt     120 gcggcgccg cgggcgtcgc caccgccgcc ggcagcggcg cggcgctggc cgccagcggc     180
gacggcgcgg tcgcgccggg ccagctggac gactattacg gcttctggtc ctcgggccag     240
accggcgagc tgcgcatcct gggcgttccc tcgatgcgcg agctgatgcg ggtgccggtc     300
ttcaaccgct gctcggccac cggctggggc atcaccaacg agtcgatcct catccacgaa     360
cgcaccatga gcgagcggac gaggaagcac cttgccgcca acggcaagcg catccacgac     420
aacggcgacc tgcaccacgt ccacatgtcc tttaccgagg caagtatga cggccgcttc     480 ctgttcatga cgacaaggc caatacccgc gtggcgcggg tgcgctgcga cgtgatgaaa     540
tgcgacgcca tcctggaggt gccgaacgcc aaggccatcc acggcctgcg cccgcagaaa     600
tggccgcgca gcaactatgt gttctgcaac ggcgaggacg aggcgccgct gatcaacgac     660
ggcaccacga tggacgacat ctcgacctat gtgaacgtct tcaccgccgt cgatgccgac     720
aagtgggaag tcgcctggca ggtgctggtc tcgggcaacc tcgacaactg cgatgccgat     780
tacgagggca atgggccctt ctcgacctcg tataactcgg agatgggcat gaccctgccc     840
gagatgaccg aagccgagat ggaccatgtc gtggtcttca acatcgccga gatcgaaaag     900
gccatcgagg ccggcaattt tgaagagatc aacggctgca aggtgctgga cggccggaaa     960
gaggcgaaca gccagttcac ccgctacatc ccgatcgcca caacccgca tggctgcaac    1020 atggccccgg acaagaagca cctggtcgtc gcgggcaagc tgtcgcccac ggtgacggtg    1080
```

```
ctggacgtga ccaggttcga cgcggtgttc aacgagaatg ccgatccgcg cagcgccgtg    1140
gtggccgagc cggaactggg cctgggcccg ctgcacaccg ccttcgacgg gcgcggcaac    1200
gcctatacct cgctgtttct cgacagccag gtggtcaagt ggaacatcga ggaggcgatc    1260
cgcgcctatg ccggcgagca ggtcgatccg atcaaggaca agatcgacgt gcattaccag    1320
cccggccacc tcaagacggt gatgggcgag acgctggacg ccagcaacga ctggatggtc    1380
tgcctgtcca gttctcgaa  ggaccgcttc ctgaacgtcg gccgctgaa  gccggaaaac    1440 gaccagctga tcgacatctc gggcgacaag atggtgctgg tccatgacgg cccgaccttt    1500
gccgagccga tgacgccat  cgccgtgcat ccctcgatca tgtcgagcgt catcaagtcg    1560
gtctgggacc gcaacgatcc catgtgggcc gaaacccgca agcaggccga ggccgacggc    1620
gtcaacatcg acgaatggac cgaccagatc atccgcgacg caacaaggt  gcgggtctac    1680 atgtccagcg tcgcgcccag cttctcggtc gaaagcttca ccgtgaccga gggcgacgag    1740
gtcacggtca tcgtcaccaa ccttgacgag atcgacgacc tgacccacgg tttcaccatg    1800
ggcaaccacg gtgtcgccat ggagatctcg ccccagcaga cctcgtcggt gactttcgtc    1860
gccgccaatc cggggtgta  ctggtattat tgccagtggt tctgccatgc gctgcacatg    1920
gaaatgcgcg gccgcatgat ggtcgagccg aaggcggcct ga                       1962

<210> SEQ ID NO 9
<211> LENGTH: 1962
<212> TYPE: DNA
<213> ORGANISM: Artificial
<220> FEATURE:
<223> OTHER INFORMATION: Codon optimized NosZ gene

<400> SEQUENCE: 9
atggaaacaa aacagcagaa cggtttatca cgtcgtgcac tgctcggtgc cacggcaggg      60
ggtgcggcca tggcgggtgc gttcggcggc cgcttggcat taggtccggc agtaattggt     120
gcaggtgctg caggcgttgc gaccgcggca ggctctgggg cagcgctcgc ggcgagcggt     180
gacggcgcgg ttgctccagg gcagttagat gactactatg ctttttggtc gtccggtcaa     240 actgcgagc tccgcatttt aggcgttcct tcgatgcggg agttaatgcg tgtcccagta      300
tttaatcgtt gttccgcaac gggttggggc attacgaacg aatcaatctt aatccatgaa     360
cggactatgt ccgaacgcac tcgtaagcac ctcgcagcga acgtaagcg  tatccacgat     420 aatggggacc tgcaccacgt acacatgtct ttcactgaag gcaagtacga tgggcgtttc     480
cttttcatga atgacaaggc caatactcgt gttgcacggg tacgttgcga cgttatgaaa     540
tgcgatgcta ttctggaggt tcctaacgca aaagcaattc atggtttacg gccacaaaag     600
tggcctcgga gtaattatgt attctgtaac ggcgaggacg aagcccctct catcaatgac     660
ggcacgacga tggatgacat ttctacgtac gtgaatgtat ttacggccgt ggacgcggac     720
aaatgggaag tagcctggca agtactggtc tctggtaatc tggacaattg tgacgcggat     780
tacgaaggca agtgggcttt tctacctca  tacaatagtg aaatgggtat gactctcccg     840
gagatgacgg aggccgagat ggaccatgtg gtagtgttta acattgcaga gattgaaaaa     900
gcgattgagg cggggaattt cgaggaaatt aacgggtgca agtcttgga  cggtcgtaag     960 gaggccaatt cccagttcac acggtatatc cctattgcaa ataacccaca cggttgtaac    1020
atggccccgg ataaaaagca tctggtagta gcaggcaagt tgtctcctac cgtaacagtt    1080
ttagatgtta cgcgcttcga tgcggtgttt aatgaaaatg cagatcctcg ctcagcagtt    1140
```

-continued

```
gtcgctgagc cagaacttgg tttgggtccg ctgcacactg catttgacgg gcggggggaat    1200 gcatacacat ctttgtttct cgactcgcaa gtcgttaaat ggaacatcga agaggcgatt    1260
cgcgcttatg ctggcgagca agtcgatccg atcaaagaca aaatcgacgt acattatcag    1320
ccgggtcatc ttaagacagt tatgggcgag actttggacg cctcgaacga ctggatggtc    1380
tgcctttcca agttttcgaa agatcggttt ctcaacgttg ccccactcaa gccagaaaat    1440
gatcaactca ttgacatttc tggtgacaag atggtacttg tccacgatgg gccgacatttt    1500 gccgagcctc acgatgcaat tgcagtgcac ccttcaatca tgagtagtgt tattaaatcc    1560
gtctgggacc gcaatgaccc gatgtgggcg gagactcgga agcaggccga ggctgatggc    1620
gttaatattg atgagtggac cgaccagatt atccgtgacg caacaaagt tcgggtatat    1680 atgagttcgg tagctccgag cttttcagtg gaaagtttta ccgttactga gggtgatgag    1740
gtaacggtca ttgttacgaa cctcgacgag atcgatgatc tgactcacgg gttcacgatg    1800
ggcaatcacg gggtagccat ggagatcagt ccacaacaaa catcgtcggt aacctttgtt    1860
gcagccaatc cgggcgttta ttggtattat tgtcagtggt tctgtcacgc attacatatg    1920
gaaatgcgcg gtcgcatgat ggtggaacca aaagctgcgt ga    1962
```

<210> SEQ ID NO 10
<211> LENGTH: 726
<212> TYPE: PRT
<213> ORGANISM: Pseudomonas stutzeri

<400> SEQUENCE: 10

```
Met Lys Pro Leu Gly Phe Ala Val Val Gly Thr Ser Arg Arg Trp Val
1               5                   10                  15

Ala Gly Phe Ala Ile Leu Leu Ala Leu Met Phe Cys Val Ser Val Ala
            20                  25                  30

Gln Ala Lys Glu Tyr Glu Ala Glu Gln Gln Arg Ile Glu Leu Leu Phe
        35                  40                  45

Pro Lys Val Thr Glu Ile Ser Glu Pro Glu Gly Glu Tyr Gln Val Arg
    50                  55                  60

Thr Leu Ala Asp Gly Val Gly Thr Ile Tyr Gly Tyr Ala Phe Gln Ser
65                  70                  75                  80

Ile Asn Val Thr Asp Met Pro Ala Tyr Ser Gly Lys Pro Ile Asn Met
                85                  90                  95

Gln Ile Leu Leu Asp Pro Lys Gly Val Ile Val Asp Ala Tyr Met Leu
            100                 105                 110

Glu His His Glu Pro Ile Val Leu Ile Gly Ile Pro Glu Gln Lys Val
        115                 120                 125

His Asp Phe Asn Ala Asn Tyr Ser Gly Ile His Val Asp Gln Arg Val
    130                 135                 140

Val Val Gly Arg Ser Ser Asp Lys Ser Ala Val Thr Val Asp Ala Val
145                 150                 155                 160

Thr Gly Ala Thr Val Thr Val Met Val Ile Asn Glu Ile Val Met Arg
                165                 170                 175

Ala Ala His Thr Val Ala Val Asp Leu Gly Leu Val Glu Ala Gly Ala
            180                 185                 190

Thr Ala Arg Pro Lys Pro Ala Leu Val Arg Glu Asp Val Phe Gln Pro
        195                 200                 205

Thr Ser Trp Thr Glu Leu Val Gly Asn Gly Ala Ile Arg Arg Met His
    210                 215                 220
```

```
Leu Thr Arg Gly Gln Val Asp Asp Ala Phe Lys Gly Thr Glu Ala Glu
225                 230                 235                 240

Gly Val Asp Val Ala Ala Glu Gln Arg Asp Glu Thr Phe Ile Asp
            245                 250                 255

Leu Tyr Ala Thr His Leu Asn Pro Pro Thr Ile Gly Arg Asn Leu Leu
            260                 265                 270

Gly Glu Arg Gln Tyr Ala Asp Leu Met Ala Asn Leu Lys Pro Gly Glu
        275                 280                 285

His Ala Phe Ala Val Leu Ala Asn Gly Glu Tyr Ser Phe Lys Gly Ser
    290                 295                 300

Gly Tyr Val Arg Gly Gly Ile Phe Asp Arg Val Gln Leu Arg Gln Phe
305                 310                 315                 320

Gly Asp Thr Ile Ser Phe Arg Asp Leu Asp Phe Ile Arg Leu Ser Asp
                325                 330                 335

Val Tyr Ala Glu Gly Met Pro Glu Phe Phe Glu Met Ala Ile Phe Thr
            340                 345                 350

Ala Arg Glu Gln Tyr Arg Phe Asp Pro Gly Ser Pro Trp Asn Leu Glu
        355                 360                 365

Leu Leu Val Arg Arg Gln Val Gly Pro Val Ser Ile Phe Thr Ser
370                 375                 380

Phe Glu Met Pro Tyr Val Met Pro Glu Glu Tyr Ile Glu Arg Val Pro
385                 390                 395                 400

Leu Thr Ala Glu Glu Leu Ala Ala Ile Glu Glu Ala Asn Arg Pro Leu
                405                 410                 415

Trp Val Asn Ile Trp Tyr Gln Lys Ser Phe Gln Val Gly Val Ile Leu
            420                 425                 430

Val Ala Leu Ala Leu Leu Thr Val Ile Leu Phe Leu Gln Asp Lys Phe
        435                 440                 445

Thr Gln His Pro Asn Phe Leu Lys Arg Leu Arg His Gly Tyr Leu Val
    450                 455                 460

Phe Thr Val Val Phe Ile Gly Trp Tyr Ala Leu Gly Gln Leu Ser Val
465                 470                 475                 480

Val Asn Val Leu Thr Phe Val His Ala Leu Val Gln Asp Phe Arg Trp
                485                 490                 495

Glu Leu Phe Leu Thr Asp Pro Val Ile Phe Ile Leu Trp Val Phe Thr
            500                 505                 510

Ala Ala Ser Ile Leu Leu Trp Gly Arg Gly Val Phe Cys Gly Trp Leu
        515                 520                 525

Cys Pro Phe Gly Ala Leu Gln Glu Leu Ile Asn Glu Ala Ala Arg Lys
    530                 535                 540

Leu Lys Ile Pro Gln Tyr Asp Leu Pro Phe Gly Val His Glu Arg Leu
545                 550                 555                 560

Trp Ala Ile Lys Tyr Ile Val Leu Val Leu Phe Gly Ile Ser Leu
                565                 570                 575

Glu Ser Met Met Met Ala Glu Lys Ala Glu Ile Glu Pro Phe Lys
            580                 585                 590

Thr Ala Ile Thr Leu Lys Phe Asp Arg Gln Trp Trp Phe Val Ala Tyr
        595                 600                 605

Ala Val Phe Leu Leu Val Ile Asn Ile Phe Thr Arg Lys Val Tyr Cys
    610                 615                 620

Arg Tyr Val Cys Pro Leu Gly Ala Gly Leu Ala Ile Thr Gly Arg Phe
625                 630                 635                 640
```

```
Arg Leu Phe Asp Trp Leu Lys Arg Arg Lys Glu Cys Gly Asn Pro Cys
                645                 650                 655

Gln Ile Cys Ala Asn Glu Cys Glu Val Gln Ala Ile His Pro Asp Gly
            660                 665                 670

His Ile Asn His Asn Glu Cys His Tyr Cys Leu Asp Cys Gln Met Thr
        675                 680                 685

Tyr His Asn Glu Asn Lys Cys Pro Pro Leu Ile Gln Lys Asn Lys Arg
    690                 695                 700

Lys Lys Arg Asp Lys Lys Ala Pro Val Gly Ala Glu Leu Ile Pro Val
705                 710                 715                 720

Val Gln Val Val Glu Pro
            725

<210> SEQ ID NO 11
<211> LENGTH: 2181
<212> TYPE: DNA
<213> ORGANISM: Pseudomonas stutzeri

<400> SEQUENCE: 11
```

| | | | | | |
|---|---|---|---|---|---|
| atgaaacccc | taggttttgc | agtcgtcggc | acctcgcgcc | gctgggtagc | tggctttgcg     60 |
| atcctcctgg | ctttgatgtt | ctgtgtatcc | gtggcacagg | caaaagagta | cgaagcagag    120 |
| cagcaacgca | tcgagttgct | ttttcccgaaa | gtcaccgaaa | tttccgagcc | cgagggcgag    180 |
| taccaggtgc | gcacccttgc | ggacggggtg | ggcacgatct | acgggtacgc | cttccagagc    240 |
| atcaacgtca | cggacatgcc | ggcctactcc | ggcaagccga | tcaacatgca | gatcctgctc    300 |
| gaccccaagg | gcgtcatcgt | cgatgcttac | atgctcgagc | accacgaacc | catcgtgctc    360 |
| atcggtattc | ccgagcagaa | ggttcacgac | ttcaacgcca | actacagcgg | catccacgtc    420 |
| gaccagcgcg | tggtagtcgg | tcgttccagc | gacaagagcg | cggtcacggt | cgacgccgtt    480 |
| accggcgcca | ccgtgaccgt | gatggtgatc | aacgagatcg | tcatgcgtgc | ggcccacacc    540 |
| gtggcggtga | tctggggct | ggtcgaggcg | ggggccaccg | cgcgacccaa | gccggcgctg    600 |
| gtgcgcgagg | acgtcttcca | gccgaccagc | tggaccgagc | tggtgggcaa | tggcgccatc    660 |
| cgccgcatgc | acctgacccg | tggccaggtc | gacgatgcct | tcaagggcac | cgaggccgag    720 |
| ggtgtcgacg | ttgccgcggc | ggaacagcgc | gacgaaacct | tcatcgatct | ctacgccacg    780 |
| cacctgaacc | cgccgaccat | cggccgcaac | ctgctgggcg | agcgccagta | cgccgatctg    840 |
| atggcgaacc | tcaagccggg | cgagcatgcc | ttcgcggtgc | tggccaacgg | cgaatactca    900 |
| ttcaagggct | cgggttacgt | gcgtggcggc | atcttcgatc | gggtgcagct | cgccagttc     960 |
| ggcgacacca | tcagcttccg | cgacctggac | ttcatccgtc | tatccgacgt | gtatgccgaa   1020 |
| ggcatgccgg | aattcttcga | gatggcgatc | ttcactgccc | gcgagcagta | tcgcttcgat   1080 |
| ccgggctcgc | cctggaacct | cgagcttctg | gtgcgtcgcc | aggtcggccc | ggtggagagc   1140 |
| atcttcacca | gcttcgagat | gcctacgtg | atgcccgagg | agtacatcga | gcgggtgccg   1200 |
| ctgaccgccg | aagagctggc | cgccatcgag | gaagccaacc | ggccgctgtg | gtcaacatc   1260 |
| tggtaccaga | gagcttcca | ggtgggggtg | atcctggtcg | cgctggcgct | gctgacggtc   1320 |
| atcctcttcc | tgcaggacaa | gttcacccag | catcccaact | tcctcaagcg | gctgcgccat   1380 |
| ggctacctgg | tcttcaccgt | ggtgttcatc | ggctggtatg | ccctggggca | actgtcggtg   1440 |
| gtcaacgtgc | tgaccttcgt | ccatgcgctg | gtgcaggact | ccgctgggga | gctgttcctg   1500 |
| accgatccgg | tgatcttcat | tctctgggta | ttcaccgccg | ctagcattct | gctgtggggg   1560 |
| cgtggcgtgt | tctgcggctg | gctgtgcccc | ttcggcgccc | tgcaggagct | gatcaacgag   1620 |

| | |
|---|---|
| gccgcgcgca agctgaagat tccccagtac gacctgccct tcggcgttca cgagcggctc | 1680 |
| tgggccatca agtacatcgt gctgctggtg ctttcggca tctcgctgga atccatgatg | 1740 |
| atggccgaga aggccgccga gatcgaaccc ttcaagaccg ccatcacgct gaagttcgac | 1800 |
| cgccagtggt ggttcgtcgc ctacgcgtg ttcctgctgg taatcaacat cttcactcgc | 1860 |
| aaggtctatt gccgctacgt ctgcccgctg ggcgcgggc tggcgatcac cggtcgcttc | 1920 |
| cggctgttcg actggctcaa gcggcgcaag gaatgcggca ccctgtca gatctgtgcc | 1980 |
| aacgaatgcg aagtgcaggc gattcatccg gacgggcata tcaaccacaa cgaatgccat | 2040 |
| tactgcctgg actgccagat gacctaccac aacgaaaaca gtgcccgcc gcttattcag | 2100 |
| aagaacaagc gcaagaagcg cgacaagaaa cgccggtcg gggccgagct gatccctgta | 2160 |
| gtgcaagtgg tggaaccctg a | 2181 |

<210> SEQ ID NO 12
<211> LENGTH: 2181
<212> TYPE: DNA
<213> ORGANISM: Artificial
<220> FEATURE:
<223> OTHER INFORMATION: Codon optimized NosR gene

<400> SEQUENCE: 12

| | |
|---|---|
| atgaagccgt taggtttcgc cgtcgtaggc acatcccgcc gctgggttgc tggtttcgca | 60 |
| atcctgctcg ccctgatgtt ttgtgttagt gtagcgcagg ctaaagagta cgaagcagag | 120 |
| caacagcgca ttgaattact ctttcctaaa gtgactgaga tctcagaacc ggagggcgaa | 180 |
| taccaagtgc gtacgcttgc agatggtgtg ggtacgatct atgggtatgc cttccagtcc | 240 |
| atcaatgtaa ccgatatgcc ggcgtatagt ggtaaaccga tcaatatgca gattctcctg | 300 |
| gacccaaagg gggtaatcgt cgacgcttac atgctcgagc accatgaacc tattgtgctg | 360 |
| atcggtattc cggaacagaa agttcacgac ttcaacgcta attacagtgg gatccatgtt | 420 |
| gaccagcgcg ttgtcgtagg tcgtagttcc gataaatcgg cagttaccgt ggatgccgtc | 480 |
| actggcgcta ccgtcacagt aatggtcatc aacgagatcg tcatgcgcgc ggctcacacg | 540 |
| gtcgcagtag atttgggtct cgttgaggct ggtgccactg cccgcccgaa gccggcatta | 600 |
| gtgcgcgaag acgttttcca gccaacatcg tggaccgagc ttgtgggcaa tgggcatt | 660 |
| cgccgtatgc acttaacccg cggtcaagtt gacgatgcct ttaaaggtac tgaagctgag | 720 |
| ggcgtggatg ttgctgccgc tgagcagcgc gacgaaacct ttattgactt atatgcgacc | 780 |
| catcttaacc cacctacaat cggtcgtaac ttacttgggg aacgccagta tgcggatctg | 840 |
| atggcaaatc tgaaaccagg cgagcacgct ttcgccgttt tagcgaatgg cgagtacagc | 900 |
| ttcaaagggt ccggctatgt gcgcggcggg atttttgatc gcgtgcaact ccgtcagttt | 960 |
| ggggacacta tctcttttcg tgatttggat tttattcgtc tttctgacgt atatgcggaa | 1020 |
| ggtatgccag agtttttcga atggcaatt tttactgcac gcgaacaata ccgctttgac | 1080 |
| ccagggtctc cgtggaatct cgaattattg gtacgccgtc aagtcggtcc agtcgagtca | 1140 |
| atctttactt cattcgaaat gccttacgtg atgcctgaag aatacatcga gcgcgtgccg | 1200 |
| cttaccgctg aagaacttgc cgcaatcgag gaagcgaacc gccctctttg ggtcaatatc | 1260 |
| tggtatcaga aatcgtttca agttggggtg atcctggtcg cccttgctct cttaacggta | 1320 |
| attttgttcc ttcaagacaa atttacccag catcctaact tccttaagcg cttgcgccat | 1380 |
| ggctacctcg tattcaccgt cgttttatt ggctggtatg cattaggcca gttatctgtc | 1440 |

-continued

```
gtgaacgtgc ttacattcgt tcacgcactt gtgcaggact ttcgctggga gctgtttctc    1500
accgaccctg tgatcttcat cctgtgggtc ttcaccgctg ccagcattct tctctggggg    1560
cgcggggtct tttgtgggtg gctgtgtcca tttggcgccc tccaggaact tatcaatgaa    1620
gccgcgcgca agctgaagat cccgcagtat gatcttccgt ttggcgttca tgagcgcctt    1680
tgggccatta agtatatcgt actgctggtc ttatttggta tctctttaga gtcaatgatg    1740
atggcggaaa aggccgcaga aattgagcct tttaaaactg cgatcacact gaaattcgac    1800
cgccaatggt ggttcgtggc ctatgccgtt ttcttgttgg ttatcaatat tttcacccgc    1860
aaggtttatt gccgttatgt ttgtcctctc ggtgccggcc tcgctatcac cggtcgtttt    1920
cgcttatttg attggcttaa acgtcgtaaa gagtgtggca acccgtgtca gatctgtgct    1980
aacgagtgcg aggtacaggc gatccatcct gatgggcaca tcaaccacaa tgagtgtcac    2040
tattgcttgg actgccaaat gacgtaccat aatgaaaaca gtgtccacc gttgattcaa     2100 aagaataagc gtaaaaagcg cgacaaaaaa gccccggtag gcgcagagtt aatcccagtg    2160
gtccaagtgg ttgagccttg a                                              2181
```

<210> SEQ ID NO 13
<211> LENGTH: 715
<212> TYPE: PRT
<213> ORGANISM: Pseudomonas aeruginosa

<400> SEQUENCE: 13

```
Met Arg Ala Leu Arg Phe Ser Ala Gly Ser Trp Arg Cys Val Phe Ala
1               5                   10                  15

Trp Met Leu Leu Val Gly Leu Ala Ala Gln Gly Ala Glu Leu Ser
            20                  25                  30

Glu Leu Glu Arg Leu Arg Ile Ala Gln Val Phe Pro Ala Val Glu Arg
        35                  40                  45

Ile Gly Asp Pro Glu Gly Asp Tyr Gly Val Arg Arg Leu Ser Lys Gly
    50                  55                  60

Glu Glu Thr Leu Gly Tyr Ala Phe Gln Thr Leu Ser Val Thr Asp Ile
65                  70                  75                  80

Pro Ala Tyr Ser Gly Lys Pro Ile Asn Leu Gln Val Ile Leu Asp Pro
                85                  90                  95

Gln Ala Val Ile Arg Asp Ala Tyr Val Leu Glu His His Glu Pro Ile
            100                 105                 110

Leu Leu Ile Gly Ile Pro Glu Glu Lys Leu His Ala Phe Ser Ala Arg
        115                 120                 125

Tyr Asp Gly Val Arg Ala Asp Gln Arg Val Val Gly Arg Ser Ser
    130                 135                 140

Asp Pro Gln Ala Val Thr Val Asp Ala Val Ser Gly Ala Thr Val Thr
145                 150                 155                 160

Val Met Val Val Asn Glu Ile Val Met Arg Ala Ala His Thr Val Ala
                165                 170                 175

Val Ser Leu Gly Leu Ile Glu Asp Arg Gly Asn Val Arg Pro Lys Pro
            180                 185                 190

Ala Gln Val Arg Gln Gln Pro Ala Ala Thr Ala Asn Trp Ser Glu Leu
        195                 200                 205

Leu Gly Asn Gly Ala Ile Arg Arg Leu Gln Leu Ser Arg Gly Gln Ile
    210                 215                 220

Asp Asp Ala Phe Lys Gly Ser Glu Ala Glu Gly Ile Gly Glu Ala Asp
225                 230                 235                 240
```

-continued

```
Ala Ala His Arg Asp Glu Pro Phe Ile Asp Leu Tyr Ser Ala Leu Leu
            245                 250                 255

Asn Pro Pro Ala Val Gly Arg Ser Leu Leu Gly Asp Asn Gln Tyr Arg
            260                 265                 270

Glu Leu Met Ala Ser Leu Lys Pro Gly Glu Tyr Ala Phe Val Val Leu
            275                 280                 285

Gly Asp Gly Glu Tyr Ser Phe Lys Gly Ser Gly Tyr Val Arg Gly Gly
            290                 295                 300

Ile Phe Asp Arg Val Gln Leu Arg Gln Phe Gly Asp Ile Ile Ser Phe
305                 310                 315                 320

Arg Asp Leu Asp Tyr Gln Arg Leu Ser Asp Val Tyr Ala Glu Gly Met
            325                 330                 335

Pro Glu Phe Arg Glu Met Ala Ile Phe Val Ala Arg Ala Ser Gln Arg
            340                 345                 350

Phe Asp Pro Gly Ser Pro Trp Thr Leu Glu Leu Leu Val Arg Arg Gln
            355                 360                 365

Thr Gly Pro Val Ala Gly Val Phe Thr Ser Phe Glu Leu Ala Cys Gln
            370                 375                 380

Thr Pro Glu Glu Tyr Leu Glu Arg Pro Gln Pro Thr Ala Glu Glu Leu
385                 390                 395                 400

Ala Ala Leu Glu Glu Ala Ala Arg Pro Leu Trp Leu Arg Val Trp Tyr
            405                 410                 415

Gln Lys Ser Phe Gln Val Gly Val Leu Cys Thr Ala Leu Val Leu Leu
            420                 425                 430

Leu Ala Ile Leu Phe Leu Gln Asp Arg Leu Val Arg Arg Pro Arg Leu
            435                 440                 445

Met Gln Arg Leu Arg Thr Gly Tyr Leu Ala Phe Thr Leu Val Tyr Leu
            450                 455                 460

Gly Trp Tyr Ser Leu Gly Gln Leu Ser Val Val Asn Val Leu Thr Phe
465                 470                 475                 480

Val His Ala Leu Phe Glu Gly Phe Arg Trp Glu Leu Phe Leu Ser Asp
            485                 490                 495

Pro Leu Leu Phe Ile Leu Trp Thr Phe Thr Ala Ala Ser Leu Leu Leu
            500                 505                 510

Trp Gly Arg Gly Val Phe Cys Gly Trp Leu Cys Pro Phe Gly Ala Leu
            515                 520                 525

Gln Glu Leu Leu Asn Glu Leu Ala Arg Lys Leu Arg Val Pro Gln Phe
            530                 535                 540

Gln Val Pro Phe Ala Val His Glu Arg Leu Trp Ala Ile Lys Tyr Ile
545                 550                 555                 560

Ile Leu Leu Val Leu Phe Gly Leu Ser Leu Glu Ser Leu Ala Leu Ala
            565                 570                 575

Glu Gln Ala Ala Glu Val Glu Pro Phe Lys Thr Ala Ile Thr Leu Gly
            580                 585                 590

Phe Asp Arg Gln Trp Trp Phe Val Ala Tyr Ala Val Ala Leu Leu Val
            595                 600                 605

Val Asn Leu Phe Thr Arg Lys Val Tyr Cys Arg Tyr Leu Cys Pro Leu
            610                 615                 620

Gly Ala Ala Leu Ala Ile Pro Ala Lys Ala Arg Leu Phe Asp Trp Leu
625                 630                 635                 640

Lys Arg Arg Ala Glu Cys Gly Arg Pro Cys Gln Leu Cys Ala Arg Glu
            645                 650                 655
```

Cys Glu Ile Gln Ala Ile His Pro Asp Gly Arg Ile Glu Thr Asn Glu
               660                 665                 670

Cys His Tyr Cys Leu Asp Cys Gln Met Thr Tyr His Asp Gln Asp Lys
           675                 680                 685

Cys Pro Pro Leu Val Asn Lys Arg Lys Arg Ala Lys Ser Ala Pro
       690                 695                 700

Ala Asp Asn Ala Arg Ile Pro Ala Glu Asn Leu
705                 710                 715

<210> SEQ ID NO 14
<211> LENGTH: 2148
<212> TYPE: DNA
<213> ORGANISM: Pseudomonas aeruginosa

<400> SEQUENCE: 14

| | |
|---|---:|
| atgcgcgccc ttcgttttc cgccggatcg tggcggtgtg tcttcgcctg gatgctcctg | 60 |
| ctggtcggcc tcgccgccca gggtgccgaa ctcagcgagt ggagcgcct gcgcatcgcc | 120 |
| caggtattcc ccgcggtcga gcggatcggc gaccccgaag cgactacgg cgtacgccgc | 180 |
| ctgagcaagg gcgaggaaac cctcggctac gccttccaga ccctcagcgt caccgacatc | 240 |
| ccggcttact ccggcaagcc gatcaacctg caggtgatcc tcgatccgca ggcggttatc | 300 |
| cgcgacgcct acgtcctcga acaccacgaa ccgatcctgc tgatcggtat cccggaagag | 360 |
| aagctgcacg ccttcagcgc caggtacgac ggcgtgcgcg ccgaccagcg ggtggtggtc | 420 |
| ggccgctcca gcgacccgca gcggttacc gtcgacgcgg tgagcggcgc cacggtgacg | 480 |
| gtgatggtgg tcaacgagat cgtcatgcgc ccgcacata cggtggcggt ttccctcggc | 540 |
| ctgatcgagg accgcggcaa tgtgcggccc aaaccggcgc aggtgcgcca gcaaccggca | 600 |
| gcgaccgcaa actggagcga actgctcggc aacgcgcga tccgccgcct gcagttgagt | 660 |
| cgcgggcaga tcgacgacgc cttcaagggc agcgaggccg aaggcatcgg cgaagccgac | 720 |
| gcggcgcacc gcgacgagcc gttcatcgat ctctacagcg ccctgctcaa ccctcccgcg | 780 |
| gtgggccgca gctgctcgg cgacaaccag taccgcgaac tgatggcgtc gctgaagcca | 840 |
| ggcgaatacg ccttcgtcgt gctcggcgac ggcgagtatt ccttcaaggg ttccggctac | 900 |
| gtgcgcggtg catcttcga tcgggtccaa ctgcgccagt tcggcgacat catcagcttc | 960 |
| cgcgacctcg actaccagcg cctgtcggac gtctatgccg aaggcatgcc ggagttccgc | 1020 |
| gagatggcga tcttcgtcgc ccgcgccagc cagcgtttcg atccgggctc gccctggacc | 1080 |
| ctggagttgc tcgtgcggcg ccagaccggc ccggtggcgg gggtattcac cagcttcgag | 1140 |
| ctggcctgcc agacgcccga ggaatacctg gagcggccgc agccaacggc cgaggaactg | 1200 |
| gccgccctga agaggctgc ccggccgctg tggctgcggg tctggtacca aagagtttc | 1260 |
| caggtcgggg tcctctgtac cgccctcgtc ctgctcctgg cgatcctctt cctccaggac | 1320 |
| cgcctggtgc gacggccgcg cctgatgcag cgactgcgca ccggctacct ggcgttcacc | 1380 |
| ctggtctacc tgggctggta cagcctcggc cagctatcgg tggtcaacgt gctgaccttc | 1440 |
| gtccacgcgc tgttcgaagg cttccgctgg gagctgttcc tcagcgaccc gctgctgttc | 1500 |
| atcctctgga ccttcaccgc agccagcctg ctgtctctggg gccgcggcgt gttctgcggc | 1560 |
| tggctgtgcc cgttcggtgc gctacaggaa ctgctcaacg aactcgcgcg caagctccgc | 1620 |
| gtgccgcagt ccaggtgcc gttcgccgtg cacgagcggc tctgggcgat caagtacatc | 1680 |
| atcctgctgg tgctcttcgg tctctcctg gaatccctgg cgctggccga gcaggccgcg | 1740 |

```
gaggtggagc cgttcaagac cgccatcacc ctcggcttcg accgccagtg gtggttcgtc    1800
gcctacgccg tcgcgctgct ggtggtcaac ctgttcaccc gcaaggtcta ttgccgctac    1860
ctctgcccgc tgggcgcggc cctggcgatc ccggccaagg cgcgcctgtt cgactggctc    1920
aagcgccgtg cggaatgcgg caggccctgc cagctctgtg cccgcgaatg cgagatccag    1980
gcgatccatc ccgacggccg catcgagacc aacgaatgcc actactgcct cgactgccag    2040
atgacctacc acgaccagga caagtgcccg ccgctggtga acaagcgcaa gaagcgcgcg    2100
aagagcgcgc cggcggacaa cgcgcggata cccgcggaga acctctga                2148
```

<210> SEQ ID NO 15
<211> LENGTH: 2148
<212> TYPE: DNA
<213> ORGANISM: Artificial
<220> FEATURE:
<223> OTHER INFORMATION: Codon optimized NosR gene

<400> SEQUENCE: 15

```
atgcgcgcac ttcgtttctc ggcgggctcc tggcgctgcg tctttgcatg gatgttactg      60
cttgttgggt tagctgctca gggtgcagaa ctctccgaac ttgagcgctt acgtatcgca     120
caagtattcc ctgctgttga gcgtatcggg gatcctgaag gtgattatgg ggtgcgccgt     180
ctctccaaag gggaagaaac attggggtac gcgttccaaa cactcagcgt aaccgatatt     240
ccggcctact ccgggaagcc aatcaacctc caggttattt tggatcctca ggctgtcatc     300
cgtgatgcat acgtactcga acatcacgaa ccgatcctct taattggcat ccctgaggaa     360
aagctgcacg ccttctctgc ccgttacgac ggggtacgcg cagaccaacg cgtagtagtg     420
gggcgctcaa gtgatccaca agctgtaaca gtagacgctg tctcgggtgc aacggtgacg     480
gttatggtcg taaatgaaat cgtaatgcgt gcagctcaca cagtggccgt gagtcttggc     540
ctcattgagg accgcggcaa tgtccgtcca aaaccggctc aggtacgtca gcagcctgcg     600
gctacagcca attggtcaga gctgttaggg aatggcgcaa tccgccgcct gcaacttagt     660
cgcgggcaga ttgatgatgc gttcaagggg agcgaagccg agggtatcgg cgaagcagat     720
gccgcgcatc gcgatgaacc tttcatcgac ttgtacagcg ccctgcttaa tccgccagcg     780
gtaggccgct ccctcctggg ggacaaccaa taccgcgagc ttatggcgtc tctcaaacct     840
ggtgaatacg cttttgtggt gcttggtgat ggtgagtact cttttaaagg gtctggctac     900
gttcgcggcg ggattttttga ccgcgttcag ttgcgccaat cggtgatat tatttcgttt     960 cgcgacttgg attatcaacg cttgtccgac gtgtatgccg aaggtatgcc ggaattccgc    1020
gaaatggcaa tctttgtcgc gcgcgcgtca aacgttttg accctggttc tccgtggacc    1080
ctggagttat tagtacgccg tcaaaccggg ccggtggccg cgtgtttac ctccttttgag   1140 cttgcgtgcc aaacaccaga ggagtatctt gaacgccctc aacctacagc agaagagctt    1200
gcggccctgg aagaggctgc gcgcccactt tggcttcgcg tttggtacca gaagagtttt    1260
caggtcggcg tgctctgcac ggcattggtg ttactgcttg cgatcttatt tcttcaggat    1320
cgtcttgtgc gtcgtccgcg cttgatgcaa cgtcttcgca cggggtacct ggctttcacg    1380
ttagtttact taggttggta cagcctcggt caattgagtg ttgtcaatgt tcttactttt    1440
gttcatgctt tgttcgaggg ttttcgctgg gaattgtttc tttctgatcc gctcctgttt    1500
attctttgga cgtttacggc cgcctcattg ttgctgtggg ccgcggcgt cttttgtggg    1560 tggttatgtc cttttggtgc tttacaagag ttgctcaacg agctggcacg taagctgcgc   1620
gtgccgcaat tccaagttcc gtttgcggtt catgagcgct tgtgggctat taagtatatc    1680
```

-continued

```
attctgttag ttctgttcgg cttaagctta gagagcttgg cattagctga gcaagctgca    1740
gaagtcgaac catttaagac agcaattacc ttagggtttg atcgccagtg gtggttcgtg    1800
gcgtacgccg tcgcattatt ggtggtcaat ctgtttacac gtaaggtcta ctgccgctat    1860
ctttgtccgc tcggggctgc actggcaatt ccagccaaag ctcgtttgtt tgactggctc    1920
aaacgtcgcg ctgaatgcgg cgcccatgc cagttgtgcg cccgcgagtg tgaaatccaa     1980
gcaattcacc cggacggtcg cattgagacg aatgagtgtc actattgcct cgattgtcaa    2040
atgacatacc atgatcagga taagtgtccg cctcttgtga acaagcgcaa aaagcgcgcc    2100
aaatcagctc cggcggataa cgcacgtatc cctgcggaga acctctga               2148
```

<210> SEQ ID NO 16
<211> LENGTH: 729
<212> TYPE: PRT
<213> ORGANISM: Pseudomonas versutus

<400> SEQUENCE: 16

```
Met Lys Ile Leu Arg Leu Val Leu Thr Ile Ala Ser Leu Leu Leu Pro
1               5                   10                  15

Ala Leu Pro Ala Ala Glu Ser Val Leu Ala Gln Leu Leu Pro Glu
            20                  25                  30

Gln Asn Ala Gly Glu Leu Val Pro Gly Ala Asp Gly Phe Gly Pro Ile
        35                  40                  45

Arg Ala Asp Leu Ala Val Ala Pro Val Leu Lys Gly Gly Glu Thr Val
    50                  55                  60

Ala His Ala Phe Val Thr Ser Asp Phe Val Gly Thr Thr Gly Tyr Ser
65                  70                  75                  80

Gly Lys Pro Ile His Thr Leu Val Ala Leu Asp Lys Asp Ala Lys Val
                85                  90                  95

Ala Gly Val Arg Leu Val Lys His Ser Glu Pro Ile Val Leu Ile Gly
            100                 105                 110

Ile Pro Glu Ala Lys Val Lys Ala Leu Val Glu Gly Tyr Arg Gly Leu
        115                 120                 125

Asp Leu Val Ala Glu Ala Gln Ser Gly Gly Thr Ala His Glu Val Glu
    130                 135                 140

Ile Ile Ser Gly Ala Thr Val Thr Val Met Val Ile Asp Asp Ser Ile
145                 150                 155                 160

Val Arg Ser Gly Leu Lys Val Ala Arg Ala Leu Gly Leu Gly Gly Leu
                165                 170                 175

Ala Ala Glu Thr Val Ala Ala Gly Pro Lys Phe Glu Ile Asp Pro Asp
            180                 185                 190

Ala Ala Pro Ser Ala Asp Trp His Glu Met Glu Gly Asp Gly Thr Leu
        195                 200                 205

Arg Arg Leu Ser Leu Asp Val Gly Gln Val Asn Ala Ala Phe Ala Ala
    210                 215                 220

Asn Pro Asp Arg Arg Ala Ala Glu Arg Ala Leu Ser Glu Ala Pro Asp
225                 230                 235                 240

Thr Thr Phe Ile Glu Met Gln Ala Gly Leu Val Ser Val Pro Ala Ile
                245                 250                 255

Gly Lys Ala Leu Leu Gly Asp Ala Gln Ala Ala Asn Leu Gln Ala Trp
            260                 265                 270

Leu Ala Pro Gly Asp Gln Ala Ile Ala Val Met Gly Arg Gly Leu Tyr
        275                 280                 285
```

```
Ser Phe Lys Gly Ser Gly Tyr Val Arg Gly Gly Ile Phe Asp Arg Ile
    290                 295                 300

Val Leu Ile Gln Asp Asp Val Ser Val Arg Phe Arg Asp Arg Asp His
305                 310                 315                 320

Arg Arg Leu Asn Ala Val Ala Ala Asp Gly Ala Pro Asp Phe Thr Glu
                325                 330                 335

Met Asp Leu Phe Lys Ile Pro Ala Ala Ser Gly Phe Asp Pro Thr Lys
                340                 345                 350

Pro Phe Arg Ile Gln Leu Leu Val His Arg Glu Val Gly Pro Ile Glu
            355                 360                 365

Lys Val Phe His Thr Phe Asp Leu Gly Tyr Gln Leu Pro Gln Lys Tyr
        370                 375                 380

Leu Arg Ser Val Ala Ala Pro Ala Pro Ala Pro Glu Ala Ala Ala Pro
385                 390                 395                 400

Val Ala Gln Ser Asp Glu Ser Gln Ala Gln Ala Gln Leu Trp Lys Arg
                405                 410                 415

Ile Trp Leu Asp Ser Lys Pro Lys Ile Ala Gly Leu Ala Ala Met Leu
                420                 425                 430

Leu Val Leu Thr Gly Ala Phe Phe Gln Ser Phe Ala Thr Arg Asn
            435                 440                 445

Glu Arg Ala Phe Tyr Ile Phe Arg Met Gly Phe Leu Thr Val Thr Leu
    450                 455                 460

Ile Phe Leu Gly Trp Tyr Ala Asn Ala Gln Leu Ser Val Asn Leu
465                 470                 475                 480

Met Ala Leu Phe Gly Ser Leu Val Asn Gly Phe Ser Trp Gln Ala Phe
                485                 490                 495

Leu Leu Asp Pro Leu Thr Phe Ile Leu Trp Phe Ala Val Ala Ala
            500                 505                 510

Leu Leu Phe Trp Gly Arg Gly Ala Tyr Cys Gly Trp Leu Cys Pro Phe
            515                 520                 525

Gly Ala Leu Gln Glu Leu Thr Asn Gln Ile Ala Arg Lys Leu Arg Ile
            530                 535                 540

Pro Gln Trp Thr Leu Pro Trp Gly Leu His Glu Arg Leu Trp Pro Val
545                 550                 555                 560

Lys Tyr Met Ile Phe Leu Gly Leu Phe Gly Val Ser Leu Met Ser Val
                565                 570                 575

Glu Gln Ala Glu His Leu Ala Glu Val Glu Pro Phe Lys Thr Ala Ile
            580                 585                 590

Ile Leu Lys Phe Ile Arg Ala Trp Pro Phe Val Ala Tyr Ala Ala Ala
            595                 600                 605

Leu Leu Ile Ala Gly Leu Phe Val Glu Arg Phe Tyr Cys Arg Tyr Leu
    610                 615                 620

Cys Pro Leu Gly Ala Ala Leu Ala Ile Pro Ala Arg Met Arg Met Phe
625                 630                 635                 640

Asp Trp Leu Lys Arg Tyr His Glu Cys Gly Asn Pro Cys Gln Ile Cys
                645                 650                 655

Ala Gln Gln Cys Pro Val Gln Ser Ile His Pro Thr Gly Glu Ile Asn
                660                 665                 670

Pro Asn Glu Cys Ile Asn Cys Met His Cys Gln Val Leu Tyr Gln Ser
            675                 680                 685

Lys Thr Thr Cys Pro Val Val Ile Arg Lys Leu Lys Arg Glu Ala
690                 695                 700
```

Val Ala Ala Gly Ser Thr Pro Lys Leu Gly Gln Pro Pro Ala Gly His
705                 710                 715                 720

Pro Asn Ala Thr Arg Lys Ile Glu Ala
                725

<210> SEQ ID NO 17
<211> LENGTH: 2190
<212> TYPE: DNA
<213> ORGANISM: Pseudomonas versutus

<400> SEQUENCE: 17

| | | | | | |
|---|---|---|---|---|---|
| atgaagatcc | tccgccttgt | cctgacgatc | gcatcgctgt | tgctgccggc | cctgccggcc | 60 |
| gccgccgaaa | gcgtgctggc | gcagctgctg | ccggagcaga | acgcgggcga | gctggtgccc | 120 |
| ggcgccgacg | gtttcggacc | gatccgcgcc | gatctggccg | tggcgccggt | gctgaagggg | 180 |
| ggcgagaccg | tcgcccatgc | cttcgtcacc | tcggatttcg | tcggcaccac | cggctattcc | 240 |
| ggcaagccca | tccatacgct | cgtcgcgctg | acaaggacg | cgaaggtggc | cggcgtccgg | 300 |
| ctggtcaagc | attccgaacc | catcgtgctg | atcggcatcc | ccgaggccaa | ggtcaaggcg | 360 |
| ctggtcgagg | gctaccgggg | ccttgacctc | gtggccgagg | cgcaatcggg | cggcacggcg | 420 |
| catgaggtcg | agatcatctc | gggcgccacg | gtcacggtga | tggtgatcga | cgattccatc | 480 |
| gtgcgctcgg | ggctgaaggt | cgcgcgcgcg | ctcggccttg | gcgggctggc | cgccgaaacc | 540 |
| gtggccgccg | gcccgaagtt | cgagatcgac | cccgacgcgg | cccctcggc | cgactggcac | 600 |
| gagatggagg | cgacggcac | cctgcgccgg | ctgtcgctgg | acgtgggcca | ggtgaacgcg | 660 |
| gccttttgccg | ccaatcccga | ccgccgcgcc | gccgagcgcg | cgctgtccga | ggcgccggac | 720 |
| accaccttca | tcgagatgca | ggccgggctg | gtctcggtcc | cggccatcgg | caaggcgctg | 780 |
| ctgggcgatg | cgcaggccgc | gaacctgcag | gcctggctgg | cgccgggcga | ccaggccatc | 840 |
| gcggtgatgg | gccgcgggct | ctacagcttc | aagggctcgg | gctatgtccg | cggcggcatc | 900 |
| ttcgaccgca | tcgtgctgat | ccaggacgac | gtctcggtgc | gcttccgcga | ccgcgaccat | 960 |
| cgccggctga | cgccgtcgc | tgccgatggc | gcgccggatt | tcaccgagat | ggacctgttc | 1020 |
| aagatccccg | cggcttcggg | cttcgacccg | accaagccct | tccgcatcca | gctgctggtg | 1080 |
| catcgcgagg | tcgggccgat | cgagaaggtc | ttccacacct | tcgacctggg | ctatcagctg | 1140 |
| ccgcagaaat | acctgcgcag | cgttgccgcc | cccgcacccg | cgcccgaggc | ggcggcaccc | 1200 |
| gtggcccagt | ccgacgaaag | ccaggcccag | gcgcagctgt | ggaagcggat | ctggctggat | 1260 |
| tccaagccca | agatcgccgg | gcttgccgcc | atgctgctgg | tgctgacggg | gcattcttc | 1320 |
| ttccagagct | tcgcgacccg | gaacgagcgc | gccttctaca | tcttccgcat | gggctttctg | 1380 |
| accgtgacgc | tgatcttcct | gggctggtat | gccaatgcgc | agctttcggt | cgtgaacctg | 1440 |
| atggcgctgt | tcggcagcct | ggtgaacggc | ttcagctggc | aggccttcct | gctggacccg | 1500 |
| ctgaccttca | tcctgtggtt | cgcggtcgcc | gccgcgctgc | tgttctgggg | ccggggcgcc | 1560 |
| tattgcggct | ggctttgccc | cttcggcgcg | ctgcaagagc | tgaccaacca | gatcgcgcgc | 1620 |
| aagctgcgca | tcccgcaatg | gacgctgccc | tggggcctgc | acgagcggct | gtggccggtc | 1680 |
| aaatacatga | tcttcctggg | cctttttcggc | gtctcgctga | tgagcgtcga | gcaggccgag | 1740 |
| catctggccg | aggtcgagcc | cttcaagacc | gcgatcatcc | tgaaattcat | ccgcgcctgg | 1800 |
| cccttcgtgg | cctatgccgc | ggcgctgctg | atcgccgggc | tcttcgtcga | gcgcttctat | 1860 |
| tgccgctacc | tgtgccgct | tggcgcggcg | ctggcgatcc | cggcgcggat | gcgcatgttc | 1920 |

```
gactggctca agcgctatca cgaatgcggc aatccctgcc agatctgcgc ccagcaatgc    1980
ccggtgcagt cgatccaccc gacgggcgag atcaatccca acgaatgcat caactgcatg    2040
cattgccagg tgctttacca gtccaagacc acctgcccgg tggtgatccg caagttgaaa    2100
cggcgcgagg ccgtggccgc cggcagcacg cccaagctgg ccagccccc ggccggccat     2160 cccaacgcca cccgcaagat cgaagcttga                                     2190

<210> SEQ ID NO 18
<211> LENGTH: 2190
<212> TYPE: DNA
<213> ORGANISM: Artificial
<220> FEATURE:
<223> OTHER INFORMATION: Codon optimized NosR gene

<400> SEQUENCE: 18
atgaaaattt tgcgtcttgt gttaacaatt gcgtcgttgc tcctcccggc tcttcctgcg      60
gcggcggaaa gcgtcttagc ccaattgtta ccagaacaaa atgcagggga actggtacct    120
ggggctgatg gcttcgggcc tattcgtgcg gacctggccg tggcccccggt acttaagggg    180 ggtgaaaccg ttgctcacgc atttgtaacc tcggactttg tgggtaccac cggttactca    240
gggaaaccaa ttcacacgct ggtcgcttta gacaaagacg ctaaagttgc aggggtgcgc    300
ctggttaaac attcagagcc tattgtcctg attggtattc ctgaagccaa agtgaaggcc    360
ctcgtgaagg ttatcgcgg cctggacctg gttgccgaag ctcaatcggg ggggacggct     420
catgaggtag agattatctc agggcaacaa gttactgtga tggtgattga cgactcgatc    480
gtccgcagtg gtctcaaggt ggcacgcgct ctcggcctcg gggggcttgc ggcagaaact    540
gtggccgccg gcctaagtt tgagatcgac ccagatgcag ccccgtccgc cgattggcac     600
gaaatggagg gggatggcac attacgccgc ctttcgttag acgtcggcca ggttaacgct    660
gccttcgctg cgaacccaga tcgtcgcgcc gccgagcgtg cattgtcaga agcacctgat    720
acaacattca ttgagatgca ggctgggctc gtttcggttc cggcgatcgg taaggccctc    780
ctcggtgacg cccaagcggc aaatttgcaa gcttggttgg ccctggtga ccaggccatt     840 gcggttatgg gccgcggctt atattcgttc aaagggagtg gctacgttcg cggtggtatc    900
ttcgatcgta tcgtattaat ccaagatgac gtgtcagttc gctttcgcga ccgtgatcat    960
cgtcgcctca cgccgtggc cgcggacggt gccccggact tcacagagat ggacctgttc    1020
aaaatcccgg cagcaagtgg cttcgaccca acgaaaccgt ttcgcattca acttttagta    1080
catcgcgaag taggccctat tgagaaggtc tttcatactt tcgacctcgg ctatcagctg    1140
cctcaaaaat atctgcgctc ggtcgccgca ccggctccgg ccccagaggc agccgcacct    1200
gttgcccaaa gcgatgaatc acaggcgcaa gcgcagctct ggaagcgcat ttggctcgat    1260
agtaagccaa aaatcgccgg cttggccgcg atgctttag ttctcactgg tgccttttt    1320 tttcagagtt tcgccactcg caacgaacgc gccttctata ttttccgcat gggcttcctc    1380
acagtcactc tgattttct tggctggtat gctaatgctc aactgagcgt ggtaaatctt    1440
atggcacttt ttgggagttt ggtgaacggg ttctcgtggc aggcttttct cttggatcct    1500
ctcacattca ttttgtggtt cgcagttgcc gcagctcttc tcttttgggg cgtggtgct    1560 tattgtggtt ggctgtgtcc atttggcgca ttacaagaat tgaccaatca aattgctcgt    1620
aagcttcgca ttccgcagtg gaccctgcct tggggcctgc atgagcgctt atggccggta    1680
aagtatatga tcttccttgg tttatttggc gttagtttaa tgtcggtgga acaagcagaa    1740
catttggccg aagtggaacc ttttaaaacg gcaattattc tgaaatttat tcgcgcatgg    1800
```

```
ccattcgtcg cttatgcggc tgcgctgctc atcgcaggtt tgttcgtaga acgcttctac    1860
tgccgctatc tgtgtccgtt gggcgcagct ctcgcgattc cggcccgtat gcgtatgttc    1920
gattggctga agcgttatca cgagtgcggt aatccgtgcc agatttgcgc acaacagtgc    1980
ccggtccagt cgatccaccc gaccggggaa attaacccga acgaatgtat taattgcatg    2040
cactgccaag tattatacca atcgaaaacc acttgtccgg tagtcatccg caagctcaag    2100
cgccgtgaag cggttgctgc gggttcaacg ccgaaattgg gcaacctcc tgccggtcat     2160 ccgaatgcga cacgtaaaat tgaagcgtaa                                     2190
```

<210> SEQ ID NO 19
<211> LENGTH: 434
<212> TYPE: PRT
<213> ORGANISM: Pseudomonas stutzeri

<400> SEQUENCE: 19

```
Met Arg Ala Cys Tyr Thr Leu Ala Leu Thr Ala Leu Met Ile Pro Ala
1               5                   10                  15

Gly Ala Ala Leu Ala Glu Pro Gln Pro Leu Thr Ser Leu Pro Leu Gln
            20                  25                  30

Ala Gln Gly Glu Asn Arg Trp Thr Leu Pro Ala Gly Glu Tyr Ile Gly
        35                  40                  45

Gln Phe Ile Ile Asp Gln Pro Leu Ala Leu His Cys Ala Pro Gly Ala
    50                  55                  60

Val Ile Lys Ala Pro Gly Gln Gly Asn Val Leu Thr Val Arg Ala Ala
65                  70                  75                  80

Asn Val Thr Ile Glu Gly Cys Ala Leu Arg Asp Trp Gly Arg Asp Leu
                85                  90                  95

Thr Ala Met Asn Ala Ala Ile Phe Leu Glu Pro Thr Ala Thr Gly Ala
            100                 105                 110

Gln Ile Arg Asn Asn Asp Leu Gln Gly Pro Gly Phe Gly Ile Trp Ala
        115                 120                 125

Asp Arg Asn Arg Asp Leu Leu Val Glu Gly Asn Arg Ile Glu Gly Asp
    130                 135                 140

Leu Gly Leu Arg Ser Gln Asp Arg Gly Asn Gly Ile His Leu Phe Ser
145                 150                 155                 160

Val Arg Gly Ala Arg Val Ile Asp Asn His Val Trp Asn Thr Arg Asp
                165                 170                 175

Gly Ile Tyr Ile Asp Asn Ser Asn Gly Asn Ser Ile Glu Arg Asn Leu
            180                 185                 190

Phe Glu Asp Leu Arg Tyr Gly Val His Tyr Met Phe Ser His Glu Asn
        195                 200                 205

Arg Val Ile Ala Asn Val Thr Arg Arg Thr Arg Thr Gly Tyr Ala Leu
    210                 215                 220

Met Gln Ser Arg Lys Leu Thr Val Ile Gly Asn Arg Ser Glu His Asp
225                 230                 235                 240

Gln Asn Tyr Gly Ile Leu Met Asn Tyr Ile Thr Tyr Ser Thr Leu Lys
                245                 250                 255

Asp Asn Phe Val Thr Asp Val Glu Arg Gly Asp Thr Gly Gly Asp Ser
            260                 265                 270

Met Ile Ser Gly Gly Glu Gly Lys Ala Leu Phe Ile Tyr Asn Ser Leu
        275                 280                 285

Phe Asn Thr Ile Glu Asn Asn His Phe Gln Arg Ser Asp Leu Gly Ile
    290                 295                 300
```

His Leu Thr Ala Gly Ser Glu Asp Asn Arg Ile Ser Ser Asn Ala Phe
305                 310                 315                 320

Val Gly Asn Ala Gln Gln Val Lys Tyr Val Ala Ile Arg Thr Gln Glu
            325                 330                 335

Trp Ser Val Asp Gly Arg Gly Asn Tyr Trp Ser Asp Tyr Leu Gly Trp
        340                 345                 350

Asp Arg Asn Glu Asp Gly Leu Gly Asp Ile Ala Tyr Glu Pro Asn Asp
    355                 360                 365

Asn Val Asp Arg Leu Leu Trp Met Tyr Pro Gln Val Arg Leu Leu Met
370                 375                 380

Asn Ser Pro Ser Ile Glu Val Leu Arg Trp Val Gln Arg Ala Phe Pro
385                 390                 395                 400

Val Ile Lys Ser Pro Gly Val Gln Asp Ser His Pro Leu Met Lys Pro
            405                 410                 415

Pro Thr Arg Gly Val Thr Glu Glu Pro Met Asn Thr Thr Gln Arg Pro
            420                 425                 430

His Ser

<210> SEQ ID NO 20
<211> LENGTH: 1305
<212> TYPE: DNA
<213> ORGANISM: Pseudomonas stutzeri

<400> SEQUENCE: 20

```
atgcgtgcgt gctacaccct ggcgcttacc gcgctcatga ttcccgcggg agccgccctg      60
gcggaaccgc aaccgctcac ctcgctgccg ctgcaagcgc agggcgagaa ccgctggaca     120
ctgcccgccg cgaatacat  cgggcaatt c atcatcgatc aaccgctggc gctgcactgc    180
gcgccgggtg cggtgatcaa ggcgccgggg caaggcaacg tcctgaccgt gcgcgcagcg    240
aacgtgacca tcgaggggtg cgcgctgcgt gactggggc  gcgacctcac ggcgatgaac    300
gcggcgatct tcctcgaacc gaccgccacc ggcgcgcaga ttcgcaacaa cgacctgcaa    360
gggccgggct tcggcatctg gccgatcgc  aatcgtgacc tgctggtcga aggcaaccgt    420
atcgagggcg acctcggcct gcgttcccag gatcgcggca acggcatcca cctgttctcc    480
gtgcgcggtg ctcgagtcat cgacaaccat gtctggaaca cccgcgacgg catctacatc    540
gacaactcca acggcaacag catcgagcgc aacctgttcg aggacctgcg ctacggcgtg    600
cactacatgt tctcccatga aaccgcgtg  atcgccaacg tcacccgccg cacccgcacc    660
ggttacgcgc tgatgcagag ccgcaaactg accgtgatcg gcaaccgctc cgagcacgat    720
cagaactacg gcatcctgat gaactacatc acctactcga ccctcaagga caatttcgtc    780
accgatgtcg agcgtggcga taccggtggc gacagcatga tcagcggcgg tgaaggcaag    840
gcgctgttca tctacaactc gctgttcaac accatcgaga caaccacttt ccagcgcagc    900
gatctgggta tccatctgac cgccggctcg aagacaacc gtatttccag caacgccttc    960
gtcggcaacg cgcagcaggt caagtacgtc gccatacgga cccaggagtg gtcggtcgac   1020
gggcgcggca actactggag cgactacctg gctgggacc gcaacgaaga cggcctgggc   1080
gacatcgcct acgagcccaa cgacaacgtc gatcgcctgc tgtggatgta ccgcaggtg    1140
cgtctgctga tgaacagccc gagcatcgaa gtgctgcgct gggtgcagcg cgcgtttccg   1200
gtgatcaagt caccgggcgt acaggacagc catccgttga tgaagccacc tacccgaggc   1260
gtgacagagg aaccgatgaa cacaacgcag aggccccact catga                   1305
```

<210> SEQ ID NO 21
<211> LENGTH: 1305
<212> TYPE: DNA
<213> ORGANISM: Artificial
<220> FEATURE:
<223> OTHER INFORMATION: Codon optimized NosD gene

<400> SEQUENCE: 21

```
atgcgcgctt gctacactct cgcccttacg gcgttaatga ttccggccgg ggcggctctt      60
gcggaaccac agccgcttac ctccttgcct ctgcaagccc agggcgaaaa tcgctggacg     120
ctcccagcag gcgagtacat tggccaattc atcattgacc aaccgctggc actccattgt     180
gcacctgggg cggttattaa agctccgggg cagggtaatg tcttgacagt ccgcgcagca     240
aacgtgacaa tcgaggggtg cgcattgcgc gactgggggcc gcgacctcac ggccatgaat     300
gcagccatct tcttggaacc taccgccacg ggcgcacaga tccgcaataa cgatttacaa     360
ggcccaggtt tcggcatctg gccgaccgt aatcgtgatt tgcttgtgga aggcaatcgt      420
atcgaaggtg accttggctt gcgttcccag gaccgcggga atggcatcca cctttttctct     480
gtacgtggcg cacgcgtaat tgacaaccat gtttggaaca cacgcgatgg catctatatt     540
gacaactcca acggcaattc tatcgagcgt aatctgtttg aggacttgcg ctacggggta     600
cactatatgt tctcacacga aaaccgcgtt atcgcgaacg tcacccgccg cactcgcaca     660
ggctacgctt taatgcagag tcgcaaattg accgttatcg gcaatcgctc cgaacacgat     720
caaaactatg ggattttaat gaactacatt acttatagca ccctcaaaga taattttgtc     780
acggatgtcg aacgcggtga tactggcggg gattctatga tctcaggggg tgaaggtaaa     840
gctctctttta tctacaatag tctcttcaat acaattgaaa acaaccactt tcaacgttcc     900
gatctcggca tccatctgac agccggctca gaggataatc gcatctcctc caacgcattc     960
gtggggaatg ctcagcaagt caaatacgtg gcaatccgta ctcaagagtg gagtgtggac    1020
ggccgcggta actactggtc ggattacctt gggtgggatc gcaacgaaga cgggcttggc    1080
gatattgcct atgaacctaa cgacaatgta gaccgtcttc tttggatgta tccacaggtt    1140
cgcttattga tgaatagccc ttcaatcgag gttcttcgtt gggttcaacg tgcctttcct    1200
gtgatcaaaa gccctggtgt ccaggattcc catccgctta tgaaacctcc aacgcgcggt    1260
gtgactgagg aacctatgaa cacgactcag cgtcctcata gctaa                    1305
```

<210> SEQ ID NO 22
<211> LENGTH: 421
<212> TYPE: PRT
<213> ORGANISM: Pseudomonas aeruginosa

<400> SEQUENCE: 22

```
Met Ala Gly Arg Arg Ala Gly Pro Leu Leu Ala Leu Leu Leu Leu Gly
1               5                   10                  15

Leu Ala Thr Ala Arg Ala Glu Pro Val Asp Gly Leu Pro Leu Arg Ala
            20                  25                  30

Asp Gly Asp Gly Arg Trp Ser Leu Ala Ala Gly Arg Tyr Ala Gly Asn
        35                  40                  45

Phe Val Ile Asp Arg Pro Leu His Leu Arg Cys Glu Ala Gly Ala Glu
    50                  55                  60

Leu Asp Gly Gly Gly His Gly Ser Leu Leu Thr Leu Thr Ser Pro Gly
65                  70                  75                  80

Ile Thr Val Glu Gly Cys Arg Leu Arg Asn Trp Gly Arg Asn Leu Thr
                85                  90                  95
```

Glu Leu Asp Ala Ala Ile Phe Val Gly Lys Ala Ala Ser Gly Ala Val
            100                 105                 110

Ile Arg Gly Asn Asp Leu Arg Gly Ala Gly Phe Gly Val Trp Leu Asp
            115                 120                 125

Ala Thr Ala Gly Ala Gln Val Leu Asp Asn Arg Ile Glu Gly Asp Glu
130                 135                 140

Ser Val Arg Ser Gln Asp Arg Gly Asn Gly Ile His Leu Tyr Ala Val
145                 150                 155                 160

Lys Asp Ala Leu Val Arg Gly Asn Arg Val Ser His Thr Arg Asp Gly
            165                 170                 175

Val Tyr Ile Asp Thr Ser Asn Asp Ser Ile Glu Ala Asn Arg Phe
            180                 185                 190

Glu Asp Leu Arg Tyr Gly Val His Tyr Met Phe Thr His Asn Ser Arg
            195                 200                 205

Val Thr Asp Asn Leu Thr Arg Arg Thr Arg Thr Gly Tyr Ala Leu Met
            210                 215                 220

Gln Ser Arg Lys Leu Thr Val Thr Gly Asn Arg Ser Ile Asp Asp Glu
225                 230                 235                 240

Asn Tyr Gly Ile Leu Met Asn Tyr Ile Thr Tyr Ser Thr Leu Ala Gly
            245                 250                 255

Asn Arg Val Glu Gly Val Arg Ser Gly Ser Thr Gly Asp Ala Met Ile
            260                 265                 270

Ser Gly Ala Glu Gly Lys Ala Leu Phe Ile Tyr Asn Ser Leu Phe Asn
            275                 280                 285

Arg Ile Glu Gly Asn Ser Phe Ala Asp Ser Ala Leu Gly Ile His Leu
            290                 295                 300

Thr Ala Gly Ser Glu Asp Asn Arg Ile Ala Gly Asn Ala Phe Ile Gly
305                 310                 315                 320

Asn Arg Gln Gln Val Lys Tyr Val Ala Ser Arg Glu Gln Glu Trp Ser
            325                 330                 335

Ala Asp Gly Arg Gly Asn Tyr Trp Ser Asp Tyr Leu Gly Trp Asp Arg
            340                 345                 350

Asp Asp Asp Gly Leu Gly Asp Val Ala Tyr Glu Pro Asn Asp Asn Val
            355                 360                 365

Asp Arg Leu Ile Trp Leu Tyr Pro Gln Val Arg Leu Leu Leu Asn Ser
370                 375                 380

Pro Ser Ile Glu Leu Leu Arg Trp Val Gln Arg Ala Phe Pro Val Val
385                 390                 395                 400

Arg Ser Pro Gly Val Arg Asp Ser His Pro Leu Met Arg Met Pro Ala
            405                 410                 415

Ala Glu Pro Arg Pro
            420

<210> SEQ ID NO 23
<211> LENGTH: 1266
<212> TYPE: DNA
<213> ORGANISM: Pseudomonas aeruginosa

<400> SEQUENCE: 23
atggccgggc gccgggcggg gccgctcctc gccctgctcc tgctcggcct cgccacggcc      60
cgcgcggagc cggtcgacgg cctgccgctg cgggccgacg gcgatggccg ctggagcctg     120
gcggcgggcc gctacgccgg taacttcgtc atcgaccggc cgctgcacct acgctgcgag     180
gccggcgccg aactggacgg cggcggccac ggcagtctgc tgaccctgac cagccccggg     240

```
atcaccgtcg agggctgccg gctgcgcaac tggggggcgca acctgaccga actcgacgcc    300
gcgatcttcg tcggcaaggc cgccagcggc gccgtgatcc gcggcaacga cctgcgcggc    360
gcgggcttcg cgtctggct  cgacgccacg gcgggcgcgc aggtgctcga caaccgcatc    420
gagggcgacg aaagcgtgcg ctcccaggat cgcggcaacg gcatccacct ctatgcggtg    480
aaggacgccc tggtccgcgg caaccgggtc agccacaccc gcgacggggt ctacatcgac    540
acctccaacg acagcagcat cgaagccaac cgcttcgagg acctgcgcta cggcgtgcac    600
tacatgttca cccacaacag ccgggtgacc gacaacctga cccggcgcac ccgcaccggc    660
tacgcgctga tgcagagccg caagctgacc gtgaccggca accgctccat cgacgacgag    720
aactacggca tcctgatgaa ctacatcacc tactcgaccc tggccggcaa ccgcgtcgag    780
ggcgtgcgca cggcagcac  cggcgacgcg atgatttccg cgccgagggg caaggcgctg    840
ttcatctaca actcgctgtt caaccgcatc gaaggcaaca gcttcgccga cagcgccctg    900
ggcatccacc tcaccgccgg ctcggaggac aatcgcatcg ccggcaacgc cttcataggc    960
aaccgccagc aggtcaagta cgtcgccagc cgcgagcagg agtggtccgc cgacggccgc   1020
ggcaactact ggagcgacta cctgggctgg gaccgcgacg acgacggtct cggcgacgtc   1080
gcctacgagc ccaacgacaa cgtcgaccgg ctgatctggc tgtacccgca ggtacgcctg   1140
ctgttgaaca gcccgagcat cgagctgctg cgctgggtcc agcgcgcctt cccggtggtg   1200
cgctcgcccg gcgtgcgcga cagccatccg ctgatgcgga tgcccgccgc ggagccgagg   1260
ccgtga                                                             1266

<210> SEQ ID NO 24
<211> LENGTH: 1266
<212> TYPE: DNA
<213> ORGANISM: Artificial
<220> FEATURE:
<223> OTHER INFORMATION: Codon optimized NosD gene

<400> SEQUENCE: 24
atggcagggc gccgtgctgg gccactgttg gccctcttat tactcggtct cgcaactgct     60
cgtgctgaac cggtagatgg cctcccgtta cgtgctgatg cgacggtcg  ctggtcgctg    120
gctgccggtc gttatgccgg taactttgta attgatcgtc ctttgcattt acgttgcgag    180
gctgggccg  agcttgatgg tggtggtcat gggtcattac tcaccctgac gtccccgggt    240
atcacggttg aaggctgccg tctccgcaac tggggccgta atttgacaga gcttgatgca    300
gctatttttg ttggcaaagc tgcttccggc gcagtaatcc gcggcaacga cctgcgtggg    360
gcgggttttg ggtatggtt  agatgccacc gccggtgccc aggtccttga caaccgcatc    420
gaaggtgacg agagcgttcg ctcccaggac cgcggtaatg gtatccatct ctacgccgtc    480
aaggacgccc tcgtacgcgg taatcgcgtg tctcacacac gcgacggtgt ctacatcgac    540
acttccaacg actcctccat tgaggcaaat cgctttgaag accttcgcta tggcgtgcac    600
tacatgttca cccataattc tcgtgtaacc gacaacctta cacgccgcac tcgcacaggc    660
tatgcattga tgcagagccg taaactgaca gtgacgggta accgcagcat tgacgacgaa    720
aattacggca tcctcatgaa ttacatcaca tattctacgc ttgctggcaa tcgcgtggag    780
ggggtgcgta cggctcgac  gggtgacgct atgatctcgg gtgcggaagg aaggcgcttt    840
ttcatctaca attctctctt caaccgtatc gagggcaact cttttgctga ttctgcatta    900
gggattcacc tcaccgccgg ctcagaggac aatcgtatcg cgggcaacgc ctttatcggc    960
```

```
aatcgtcaac aggtaaaata cgtcgcttcg cgcgaacagg agtggtctgc cgatggccgc    1020
ggtaactact ggtctgacta cctcggctgg gatcgcgatg atgatggctt gggtgacgtc    1080
gcatacgaac caaacgacaa tgtggatcgt ttaatttggt tgtacccaca agtccgttta    1140
cttctgaata gcccttccat tgagttactt cgctgggtgc aacgtgcttt cccggtggta    1200
cgcagtccag gtgtgcgcga ttcccaccct ttgatgcgca tgccagccgc ggagcctcgc    1260
ccttaa                                                                1266
```

<210> SEQ ID NO 25
<211> LENGTH: 443
<212> TYPE: PRT
<213> ORGANISM: Pseudomonas versutus

<400> SEQUENCE: 25

```
Met Arg Ser Leu Leu Thr Leu Ala Leu Ala Leu Leu Ala Trp Pro
1               5                   10                  15

Ala Leu Ala Ala Glu His Val Val Ala Pro Gly Gln Gly Ser Leu Ala
                20                  25                  30

Gln Ala Ile Ala Gly Ala Ala Pro Gly Asp Val Leu Arg Leu Gln Asp
            35                  40                  45

Gly Val His Ala Gly Pro Val Ala Ile Asp Arg Pro Leu Thr Val Thr
        50                  55                  60

Gly Ser Arg Ala Ala Val Val Asp Gly Gln Gly Arg Gly Thr Val Val
65                  70                  75                  80

Thr Ile Ala Ala Pro Asp Val Thr Leu Gln Gly Phe Ser Val Thr Gly
                85                  90                  95

Ser Gly Met Ala Asn Lys Asp Leu Asp Ala Gly Val Lys Ile Leu Lys
                100                 105                 110

Gly Ala Asp Arg Ala Gln Val Arg Gln Leu Arg Leu Thr Gly Asn Met
            115                 120                 125

His Gly Ile Asp Val His Gly Gly Arg Asp Ala Gln Val Val Gly Asn
        130                 135                 140

Glu Ile Ile Gly Thr Arg Asp Pro Arg Met Asn Glu Arg Gly Asn Gly
145                 150                 155                 160

Ile Tyr Val Trp Asn Ser Pro Gly Thr Leu Val Gln Gly Asn Ser Val
                165                 170                 175

Arg Tyr Gly Arg Asp Gly Ile Phe Ser Asn Ala Ser Gly Asp Ser Ala
            180                 185                 190

Tyr Arg Asp Asn Leu Phe Arg Asp Leu Arg Phe Ala Val His Phe Met
        195                 200                 205

Tyr Thr Arg Asn Thr Glu Val Ser Gly Asn Val Ser Ile Gly Asn His
    210                 215                 220

Leu Gly Phe Ala Ile Met Phe Ser Asp Arg Ala Val Ile Arg Asp Asn
225                 230                 235                 240

Arg Ser Leu Gly Asp Arg Glu His Gly Leu Met Leu Asn Tyr Ala Asn
                245                 250                 255

Asn Ala Asp Val Thr Gly Asn Leu Ile Arg Gly Gly Thr Lys Lys Cys
            260                 265                 270

Leu Phe Ile Tyr Asn Ala His Lys Asn Leu Ile Trp Asp Asn Arg Phe
        275                 280                 285

Gln Asp Cys Gly Ile Gly Ile His Phe Thr Ala Gly Ser Glu Arg Asn
    290                 295                 300

Val Leu Thr Ala Asn Ala Phe Val Gly Asn Arg Glu Gln Val Lys Tyr
305                 310                 315                 320
```

Val Gly Thr Arg His Ile Glu Trp Ser His Glu Gly Arg Gly Asn Phe
            325                 330                 335

Trp Ser Asp His Pro Gly Phe Asp Leu Asn Gly Asp Gly Ile Ala Asp
            340                 345                 350

Gly Val Tyr Arg Pro Asn Asp Leu Met Asp His Ile Leu Trp Ser Gln
            355                 360                 365

Pro Ala Ala Ala Leu Leu Thr Gly Ala Pro Val Gln Leu Ile Arg
            370                 375                 380

Trp Ser Gln Gln Ser Phe Pro Ala Thr Leu Pro Gly Gly Val Gln Asp
385                 390                 395                 400

Ser Ala Pro Leu Met Arg Pro Leu Thr Ile Pro Val Pro Pro Glu Ile
            405                 410                 415

Ala Ala Tyr Glu Ala Glu Val Ala Gly Arg Trp Ala Lys Gly Thr Tyr
            420                 425                 430

Asp Asp Ile Asp Pro Asp Asp Leu Thr Ser His
            435                 440

<210> SEQ ID NO 26
<211> LENGTH: 1332
<212> TYPE: DNA
<213> ORGANISM: Pseudomonas versutus

<400> SEQUENCE: 26

```
atgcgcagcc tgctgaccct tgcccttgcc ctgctgcttg cctggcccgc gctcgcggcc      60
gagcatgtcg tggcgccggg ccagggcagc cttgcccaag ccatcgccgg ggccgccccc     120
ggcgatgtgc tgcgactgca ggacggggtc catgccggcc ccgtcgccat cgaccgtccc     180
ttgaccgtca ccggcagccg tgccgcggtg tggacgggc agggacgggg cacggtcgtc     240
accatcgccg cgcccgacgt caccttgcag ggcttttccg tcacgggctc gggcatggcg     300
aacaaggatc tggacgccgg ggtcaagatc ctcaagggcg ccgaccgggc gcaggtgcgg     360
cagttgcggc tgaccgggaa catgcacggc atcgacgtgc atggcggccg cgacgcccag     420
gtcgtcggca cgagatcat cggcacccgc gaccgcgca tgaacgagcg cggcaacggc     480
atctatgtct ggaacagccc cggcacgctg gtgcagggca attccgtccg ctacggccgc     540
gacggcatct tttcgaacgc cagcggcgac agcgcctatc gcgacaacct gtttcgcgac     600
ctgcgctttg ccgtgcattt catgtatacc cgcaacaccg aggtgtcggg caatgtcagc     660
atcggcaacc acctgggctt cgccatcatg ttctcggacc gggcggtgat ccgcgacaac     720
cgcagcctgg cgaccgcga gcatgggctg atgctgaact atgccaacaa tgccgacgtg     780
accggcaacc tgatccgcgg cggcaccaag aaatgcctgt tcatctataa cgcccacaag     840
aacctgatct gggacaaccg cttccaggat tgcggcatcg gcatccactt caccgccggg     900
tccgagcgca acgtgctgac cgcaaacgcc tttgtcggca atcgcgagca ggtgaaatac     960
gtgggcaccc gccatatcga atggagccac gaggggcgcg gcaatttctg gtccgaccat    1020
ccgggcttcg acctgaacgg cgacggcatc gccgacggcg tctatcgccc caacgacctg    1080
atggaccata tcctgtggtc gcagcccgcc gccgcgcttc tgaccggcgc ccccgccgtg    1140
cagctgatcc gctggagcca gcagagcttt ccgccaccc tgccgggcgg cgtgcaggac    1200
agcgcgcccc tgatgcgacc cctgaccatc cccgtcccgc ccgagatcgc ggcctacgag    1260
gccgaggtcg cggggcgttg ggcaaaagga acctacgatg acatcgaccc tgacgatctc    1320
acgtctcact aa                                                        1332
```

<210> SEQ ID NO 27
<211> LENGTH: 1332
<212> TYPE: DNA
<213> ORGANISM: Artificial
<220> FEATURE:
<223> OTHER INFORMATION: Codon optimized NosD gene

<400> SEQUENCE: 27

```
atgcgtagtc ttttgacact tgcgctggca ttgctcttag cttggccggc attggcggca      60
gagcacgttg ttgccccggg tcagggttcc ttagcccagg ctatcgcggg tgctgctcca     120
ggcgatgtgc ttcgcttgca agacggggta catgcgggc cagtagctat tgatcgtccg      180
ttgactgtca cgggcagccg cgctgcggtg gttgacggtc aaggccgtgg tacggttgta     240
actatcgccg caccggatgt tacactgcaa gggttctcgg taacgggtc tgggatggct      300
aataaggacc ttgatgccgg ggtgaaaatt ttaaagggg cagatcgtgc gcaggtgcgc      360
caattacgct tgacggggaa catgcatggt atcgacgtcc atggggggcg cgacgcgcaa     420
gtcgttggta acgaaattat cggtactcgc gacccacgca tgaatgagcg cggtaacggt     480
atctatgtat ggaatagccc gggcacttta gttcaaggga atagcgttcg ctacgggcgc     540
gatggcatct tagcaacgc gtcgggcgat tctgcatacc gcgataattt gttccgtgac      600
ctgcgtttcg ctgttcactt tatgtataca cgcaatactg aggtttctgg taacgtctcc     660
atcgggaatc atcttgggtt cgcgattatg ttctccgacc gcgctgttat tcgcgacaat     720
cgctctctgg gtgatcgtga gcatggcctc atgcttaatt acgcgaataa cgccgatgtc     780
accggcaatt taatccgcgg tggtactaag aaatgcctct tcatctataa cgcacacaag     840
aacttgatct gggacaatcg tttccaagac tgtgggatcg catccactt tacggccggt      900
tccgaacgca atgtttaac ggctaacgcg tttgtaggta tcgtgagca ggtaaagtac       960
gtcgggacac gtcacattga gtggtctcac gaaggtcgcg gtaacttctg gtctgatcat    1020
cctgggtttg acctcaatgg tgatggtatt gcagatggtg tctaccgccc aaatgatctt    1080
atggaccata tcctttggag tcaacctgct gcagcacttc ttaccgggc acctgctgta     1140
cagttgatcc gttggtcaca gcaatcattc ccagcgacgt tgccggggg tgtgcaagac    1200
tccgcaccac ttatgcgccc gctcactatc ccagtcccac cagagatcgc ggcgtatgaa    1260
gcagaggtag cgggtcgttg ggcaaagggc acgtatgacg acattgaccc agacgattta    1320
actagtcatt ga                                                       1332
```

<210> SEQ ID NO 28
<211> LENGTH: 308
<212> TYPE: PRT
<213> ORGANISM: Pseudomonas stutzeri

<400> SEQUENCE: 28

```
Met Asn Ala Val Glu Ile Gln Gly Val Ser Gln Arg Tyr Gly Asn Met
1               5                   10                  15

Thr Val Leu His Asp Leu Asn Leu Asn Leu Gly Glu Gly Glu Val Leu
            20                  25                  30

Gly Leu Phe Gly His Asn Gly Ala Gly Lys Thr Thr Ser Met Lys Leu
        35                  40                  45

Ile Leu Gly Leu Leu Gln Ala Ser Glu Gly Arg Val Gln Val Leu Gly
    50                  55                  60

Arg Asp Pro Arg Thr Thr Asp Val Arg Arg His Leu Gly Tyr Leu Pro
65                  70                  75                  80
```

```
Glu Asn Val Thr Phe Tyr Pro Gln Leu Thr Gly Arg Glu Thr Leu Arg
             85                  90                  95

His Phe Ala Arg Leu Lys Ser Thr Pro Leu Gly Gln Val Asp Asp Leu
            100                 105                 110

Leu Glu Gln Val Gly Leu Ala His Ala Ala Asp Arg Arg Val Lys Thr
        115                 120                 125

Tyr Ser Lys Gly Met Arg Gln Arg Leu Gly Leu Ala Gln Ala Val Leu
    130                 135                 140

Gly Glu Pro Arg Leu Leu Leu Leu Asp Glu Pro Thr Val Gly Leu Asp
145                 150                 155                 160

Pro Ile Ala Thr Gln Glu Leu Tyr Leu Leu Ile Asp Arg Leu Arg Gln
                165                 170                 175

Thr Gly Thr Ser Val Ile Leu Cys Ser His Val Leu Pro Gly Val Glu
            180                 185                 190

Ala His Ile Asn Arg Ala Ala Ile Leu Ala Lys Gly Arg Leu Gln Ala
        195                 200                 205

Ile Gly Ser Leu Lys Gln Leu Arg Ser Glu Ala Gly Leu Pro Val Arg
    210                 215                 220

Ile Arg Ala Ser Gly Ile Ser Gln Ser Glu Ala Trp Leu Glu Arg Trp
225                 230                 235                 240

Ala Asn Ala Gly His Ser Ala Gln Arg Leu Gly Glu Asp Gly Val Glu
                245                 250                 255

Val Ile Ala Ile Asn Gly His Lys Leu Pro Leu Leu Arg Glu Leu Leu
            260                 265                 270

Gly Glu Ser Glu Pro Asp Asp Val Glu Ile His Gln Pro Ser Leu Glu
        275                 280                 285

Asp Leu Tyr Arg Tyr Tyr Met Glu Arg Ala Gly Asp Val Gln Ala Ala
    290                 295                 300

Glu Gly Arg Val
305

<210> SEQ ID NO 29
<211> LENGTH: 927
<212> TYPE: DNA
<213> ORGANISM: Pseudomonas stutzeri

<400> SEQUENCE: 29
atgaatgccg tcgagatcca gggcgtcagc cagcgttacg gcaacatgac cgtgttgcat      60
gatttgaacc tgaacctcgg cgaaggcgag gtactggggc tgttcggcca taacggcgcc     120
ggcaagacca ccagcatgaa actgattctc ggcctgctgc aggccagcga agggcgcgtc     180
caggtactgg gtcgcgatcc gcgcaccacc gacgtgcgcc gtcacctggg ctatctgccg     240
gagaacgtca ccttctatcc gcaactgacg gggcgcgaga ccctgcgtca tttcgcgcgc     300
ctgaagagca cgccgctggg ccaggtggac gatctgctcg agcaggtcgg cctcgcccac     360
gccgccgatc gccgcgtgaa gacctattcc aagggcatgc gccagcggct cggcctggcc     420
caggcggtgc tcggcgagcc gcgcctgctg ctgctcgacg aacccaccgt ggggctcgac     480
cccatcgcca cccaggagct ctacctgctg atcgatcggc tgcgccagac gggtaccagc     540
gtgatcctct gttcccacgt gctgcccggc gtggaggcgc atatcaaccg tgcggcgatt     600
ctcgccaagg ggcgcctgca ggccatcggc agcctcaagc agctgcgcag cgaggccggc     660
ctgccggtgc gtatccgcgc cagtggcatc agtcagagcg aggcctggct ggagcgctgg     720
gccaatgcgg ggcactcggc gcagcgtctc ggcgaggatg gcgtcgaggt gatcgccatc     780
```

```
aacggccaca agctgccgtt gctgcgtgag ctgctcgggg aaagcgaacc cgacgatgtg    840
gaaatccacc agccttcgct ggaggatctg taccgctatt acatggagcg cgccggcgat    900
gtgcaggccg cggagggcag ggtatga                                         927
```

<210> SEQ ID NO 30
<211> LENGTH: 927
<212> TYPE: DNA
<213> ORGANISM: Artificial
<220> FEATURE:
<223> OTHER INFORMATION: Codon optimized NosD gene

<400> SEQUENCE: 30

```
atgaacgctg tggaaattca aggggtttct cagcgctatg gaatatgac  tgtactgcat     60 gatttgaact tgaacttagg ggaaggtgaa gtgcttgggt tattcggtca caatggcgct    120
gggaagacaa catcaatgaa acttatcctg gcctcctgc  aagcatccga gggtcgtgtc    180
caggtgctgg ccgtgaccc  acgtaccact gatgtgcgtc gccacctcgg ttacttacct    240
gaaaatgtca cgttttatcc tcaacttaca gggcgcgaga ctttacgtca cttcgcccgt    300
ctgaagtcca ccctctggg  ccaagtggac gatctgctgg agcaagttgg tctcgctcac    360
gctgcagacc gccgcgtgaa aacctactca aaaggtatgc ccaacgctt  gggcttagcg    420 caggcggtac tgggtgagcc tcgccttctg ctgctggatg aaccaactgt tgggttggac    480
cctattgcga cgcaagagct ctatctctta attgatcgcc tccgtcaaac tggtacgtcg    540
gttatcctgt gttcacacgt tcttccaggt gtagaggctc acattaatcg cgcagcgatc    600
cttgctaagg tcgcctcca  agccatcggg tcactcaaac aattacgcag cgaagccggg    660
ttacctgtcc gtattcgtgc ctcgggtatt tcccagagtg aggcctggtt agagcgttgg    720
gcgaatgcgg ggcattcggc gcaacgttta ggcgaggatg cgttgaagt  gattgcgatc    780 aatgggcaca aactgccatt gctccgtgag ttattgggg  aatcagaacc agacgacgtg    840
gaaattcacc aaccgtcgct ggaagatctg tatcgctact atatggaacg tgcaggtgac    900
gtgcaggccg cagaagggcg cgtataa                                         927
```

<210> SEQ ID NO 31
<211> LENGTH: 304
<212> TYPE: PRT
<213> ORGANISM: Pseudomonas aeruginosa

<400> SEQUENCE: 31

```
Met Ser Leu Val Glu Ile Asp Gly Ala Thr Leu Arg Tyr Gly Ala Leu
1               5                   10                  15

Thr Ala Leu Ser Gly Leu Asp Leu Arg Leu Glu Pro Gly Glu Val Leu
            20                  25                  30

Gly Leu Leu Gly His Asn Gly Ala Gly Lys Thr Thr Ile Lys Leu
        35                  40                  45

Val Leu Gly Leu Leu Ala Pro Ser Glu Gly Arg Val Arg Val Leu Gly
    50                  55                  60

His Asp Ala Arg Ser Leu Glu Ala Arg Arg Gln Leu Gly Tyr Leu Pro
65                  70                  75                  80

Glu Asn Val Thr Phe Tyr Pro Gln Leu Ser Gly Glu Thr Leu Arg
            85                  90                  95

His Phe Ala Arg Leu Lys Gly Val Ala Pro Ala Glu Ala Ala Arg Leu
            100                 105                 110

Leu Glu Gln Val Gly Leu Gly His Ala Ala Arg Arg Arg Leu Lys Thr
        115                 120                 125
```

Tyr Ser Lys Gly Met Arg Gln Arg Leu Gly Leu Ala Gln Ala Leu Leu
130                 135                 140

Gly Glu Pro Arg Leu Leu Leu Asp Glu Pro Thr Val Gly Leu Asp
145                 150                 155                 160

Pro Leu Ala Thr Val Glu Leu Tyr Gln Leu Leu Asp Arg Leu Arg Gly
                165                 170                 175

Gln Gly Thr Gly Ile Val Leu Cys Ser His Val Leu Pro Gly Val Glu
                180                 185                 190

Thr His Ile Asp Arg Ala Ala Ile Leu Ala Gly Gly Arg Leu Gln Val
                195                 200                 205

Ala Gly Ser Leu Ala Glu Leu Arg Arg Lys Ala Ala Leu Pro Thr Arg
210                 215                 220

Val Arg Leu Ala Ser Pro His Asn Pro Gln Trp Leu Glu Arg Trp His
225                 230                 235                 240

Arg Ala Gly Leu Ala Ala Arg Arg Leu Asp Asp Gln Arg Ile Glu Val
                245                 250                 255

Leu Leu Asp Asp Ala Glu Arg Asp Gly Val Leu Glu Ala Leu Leu Ala
                260                 265                 270

Ala Arg Glu Phe Asp Leu Glu Ile Leu Pro Pro Ser Leu Glu Asp Leu
                275                 280                 285

Tyr Arg His His Met Ser Pro Ala Pro Ala Gly Ala Thr Pro Cys Pro
                290                 295                 300

<210> SEQ ID NO 32
<211> LENGTH: 915
<212> TYPE: DNA
<213> ORGANISM: Pseudomonas aeruginosa

<400> SEQUENCE: 32
gtgagcctgg tcgagatcga cggcgcgacc ctgcgctacg gcgccctcac cgccctgagc    60
gggctcgacc tgcgcctgga gcccggcgag gtgctcggcc tgctcggcca acggcgcc    120 ggcaagacca ccaccatcaa gctggtcctc ggcctgctgg ccccagcga aggccgcgtg    180 cgggtcctcg ccacgatgc gaggagcctg gaggcgcgcc gccagctcgg ctacctgccg    240
gagaacgtga ccttctaccc gcagctcagc ggcgcggaaa ccctgcgcca cttcgcccgc    300
ctcaagggcg tggcgccggc cgaagccgcg cgcctgctgg aacaggtcgg cctcggccat    360
gccgccaggc ggcgcctgaa aacctactcg aagggcatgc gccagcgcct cggcctggcc    420
caggcgctgc tcggcgaacc cgcctgctg ctgctcgacg aaccgacggt gggcctcgac    480
ccgctggcca ccgtcgagct ctaccaattg ctcgaccgcc tgcgcggcca gggcaccggg    540
atcgtccttt gctcccatgt gctgccggc gtcgagacgc acatcgaccg cgccgcgatt    600
ctcgccggcg gccgcctgca agtggccggc agcctcgccg aattgcgccg caaggcggct    660
ctgccgaccc gcgtgcgcct ggccagcccg cataacccgc agtggctcga acgctggcac    720
cgggccggcc tggcggcgcg gagactggac gaccagcgca tcgaggtact gctgacgat    780 gccgagcgcg acggcgtgct ggaagcgctg ctggccgcgc gcgagttcga cctggaaatc    840
ctgccgccgt cgctgaagga cctctatcgc caccacatgt ccccgcccc cgccggagcc    900 acgccatgcc cgtag                                                    915

<210> SEQ ID NO 33
<211> LENGTH: 915
<212> TYPE: DNA
<213> ORGANISM: Artificial

<220> FEATURE:
<223> OTHER INFORMATION: Codon optimized NosF gene

<400> SEQUENCE: 33

```
atgagccttg tggaaattga cggtgcgact ttacgctacg gggcgctcac tgcgctttct      60
ggcttggatt tacgcttaga gccaggggaa gtcttaggct tattagggca taacggcgct     120
ggcaagacta caacgatcaa gcttgttctc gggttgctcg cgccgagcga aggccgcgtc     180
cgtgtcctcg gcatgatgc gcgcagtttg aagctcgcc gccagttagg ttatctgcca       240
gagaacgtga ccttttatcc tcaattaagt ggggcggaga ctttacgcca tttcgctcgt     300
ttaaagggtg tagcccctgc cgaggctgca cgtcttctgg agcaagtcgg tttaggtcac     360
gcggcgcgcc gccgtcttaa aacgtactct aaagggatgc gccagcgctt gggcctcgca     420
caggccctgc ttggggagcc gcgccttctt ttgttagatg aaccgacggt aggtttggac     480
ccacttgcga ccgtggagtt atatcaactc ttggatcgcc ttcgtgggca ggggaccggg     540
atcgttttat gtagtcatgt tctgccaggg gttgagactc atatcgatcg cgctgctatt     600
ctggcaggcg gccgtcttca ggtcgcaggt tcgcttgcag aattacgccg taaagctgct     660
ttgccaaccc gcgttcgtct cgcttcaccg cacaatcctc aatggttgga acgctggcac     720
cgtgctggtc tggcagcccg ccgcttagac gaccaacgca tcgaggtatt attagacgat     780
gcggagcgcg atggtgtact tgaggctctg ctggcggccc gtgaatttga cctggaaatc     840
ctgccaccga gcttagaaga tctgtatcgc caccacatgt ccccagcgcc ggcgggtgca     900
acgccatgtc catga                                                     915
```

<210> SEQ ID NO 34
<211> LENGTH: 299
<212> TYPE: PRT
<213> ORGANISM: Pseudomonas versutus

<400> SEQUENCE: 34

```
Met Thr Ser Thr Leu Thr Ile Ser Arg Leu Thr Lys Arg Phe Gln Thr
1               5                   10                  15

Val Glu Ala Leu Ala Glu Val Ser Leu Asp Leu Gly Pro Gly Met Arg
            20                  25                  30

Val Ala Leu Leu Gly His Asn Gly Ala Gly Lys Ser Thr Met Met Lys
        35                  40                  45

Ile Ile Leu Gly Leu Ile Pro Phe Asp Ala Gly Glu Val Arg Val Cys
    50                  55                  60

Gly Ala Ala Pro Gly Ser Ala Gln Ala Arg Met Gln Val Ala Tyr Leu
65                  70                  75                  80

Pro Glu Asn Ala Ala Phe His Pro Ala Leu Thr Gly Glu Glu Gln Ile
                85                  90                  95

Arg His Tyr Leu Ser Leu Arg Gly Glu Ser Pro Arg Arg Ala Met Glu
            100                 105                 110

Leu Leu Glu Arg Val Gly Leu Ala Lys Ala Ala Arg Arg Ile Gly
        115                 120                 125

Thr Tyr Ser Lys Gly Met Arg Gln Arg Val Gly Leu Ala Gln Thr Leu
    130                 135                 140

Ile Gly Arg Pro Arg Leu Leu Val Leu Asp Glu Pro Thr Ser Gly Leu
145                 150                 155                 160

Asp Pro Val Ser Arg Arg Asp Phe Tyr Ala Leu Leu Asp Gly Leu Ala
                165                 170                 175
```

Ala Glu Gly Ala Ala Ile Leu Leu Ser Ser His Val Leu Thr Glu Val
                180                 185                 190

Glu Ala Arg Thr Asp Arg Ile Leu Ile Leu Ser Gln Gly Arg Leu Val
            195                 200                 205

Ala Glu Gly Thr Leu Ala Glu Leu Arg Arg Arg Ala Ala Leu Pro Val
    210                 215                 220

Gly Leu Thr Val Val Pro Ala Pro Gly Ala Ala Glu Ala Leu Ala Ala
225                 230                 235                 240

Ala Leu Pro Gln Ala Arg Leu Ala Gly Asp Gly Thr Leu His Leu Ala
                245                 250                 255

Cys Ala Gln Asp Glu Lys Leu Gly Leu Leu Ala Arg Ile Ala Gly Leu
            260                 265                 270

Gly Gly Gln Val Ala Asp Leu Asp Val Ile Pro Pro Ser Leu Glu Asp
    275                 280                 285

Ile Tyr Ser His Phe Ser Arg Arg Asp Gly Gln
    290                 295

<210> SEQ ID NO 35
<211> LENGTH: 900
<212> TYPE: DNA
<213> ORGANISM: Pseudomonas versutus

<400> SEQUENCE: 35

| | |
|---|---|
| atgacatcga ccctgacgat ctcacgtctc actaagcgct tccagaccgt cgaggcgctg | 60 |
| gccgaggtct cgctggacct ggggccgggg atgcgcgtcg cgcttttggg ccataacggc | 120 |
| gcgggcaagt ccacgatgat gaagatcatc ctgggcctga tccccttttga cgcgggcgag | 180 |
| gtccgggtct cggcgccgc gcccggctcg gcccaggcgc ggatgcaggt ggcctatctg | 240 |
| ccggaaaacg ccgccttcca cccggccctg accggagagg agcagatccg ccactacctt | 300 |
| tccctgcgcg cgaaagccc cgccggggcc atggaactgc tggagcgggt ggggctggcc | 360 |
| aaggccgcgc gccgccgcat cggcacctat tccaagggca tgcgccagcg cgtcggcctg | 420 |
| gcccagacgc tgatcgggcg gccgcggctt ctggttctgg acgagccgac ctcggggctc | 480 |
| gacccggtgt cgcggcgcga cttctatgcg ctgctcgacg gctggcggc cgaggggcg | 540 |
| gcgatcctct tgtcctcgca tgtgctgacc gaggtcgagg cccgcaccga ccgcatcctg | 600 |
| atcctgtcgc agggccggct ggtggccgag ggcacgctgg ccgagttgcg ccgccgcgcc | 660 |
| gccctgccgg tggggctgac cgtggtcccc gcgcccggcg cggccgaggc gctggccgcc | 720 |
| gcgttgccgc aggcgcggct ggcgggcgac ggcacgctgc acctggcctg cgcgcaggac | 780 |
| gaaaagctgg gcctgctggc gcgcatcgcc gggcttggcg gccaggtcgc ggacctggac | 840 |
| gtgatcccgc ccagcctcga ggacatctac agccatttca gcggagggaa cgggcaatga | 900 |

<210> SEQ ID NO 36
<211> LENGTH: 900
<212> TYPE: DNA
<213> ORGANISM: Artificial
<220> FEATURE:
<223> OTHER INFORMATION: Codon optimized NosF gene

<400> SEQUENCE: 36

| | |
|---|---|
| atgacaagta cactgacgat tagccgctta actaaacgtt tccagaccgt agaggcatta | 60 |
| gctgaagtta gtctcgacct cggcccgggc atgcgcgtag cgcttttggg ccataatggt | 120 |
| gcgggtaaat caacaatgat gaaaatcatt ttggggctca tcccgtttga cgctggcgag | 180 |

```
gtccgcgtct gcggggccgc cccagggtca gctcaagccc gcatgcaagt agcatactta    240
ccagagaacg ctgctttcca ccctgcactt actggtgaag agcaaattcg ccattattta    300
tcactccgcg gggagtctcc acgtcgtgct atggaattgc tggagcgcgt tgggttagct    360
aaggccgcac gccgtcgtat cggtacgtat tcaaagggta tgcgtcaacg tgtaggcttg    420
gcccaaacgc ttatcggtcg cccgcgcctc ctcgtcttag atgagccaac ctcaggtctg    480
gacccggtga gccgccgcga cttttatgcg ttactgacg gcctcgctgc tgagggtgct    540
gccattctcc tctccagcca tgttctcaca gaggtcgaag cgcgtaccga ccgtattta    600 atcctgagcc aaggccgcct tgtggccgag ggtacgttag cagagttgcg ccgtcgcgca    660
gctttgccag ttggccttac ggtcgtacca gcgccaggtg ctgctgaagc ccttgcagca    720
gcgctgcctc aagcccgtct ggcaggtgat gggacgctgc atctcgcatg tgcacaagat    780
gagaaattgg ggttactggc tcgtatcgcc gggttagggg gtcaagtcgc cgatctggac    840
gtaatcccgc cttctctcga agatatttat tcacacttta gtcgccgcga cgggcagtaa    900
```

<210> SEQ ID NO 37
<211> LENGTH: 275
<212> TYPE: PRT
<213> ORGANISM: Pseudomonas stutzeri

<400> SEQUENCE: 37

```
Met Asn Gln Val Trp Asn Ile Ala Arg Lys Glu Leu Ser Asp Gly Leu
1               5                   10                  15

Arg Asn Arg Trp Leu Leu Ala Ile Ser Leu Leu Phe Ala Val Leu Ala
                20                  25                  30

Val Gly Ile Ala Trp Leu Gly Ala Ala Ala Ser Gly Gln Val Gly Phe
            35                  40                  45

Thr Ser Ile Pro Ala Thr Ile Ala Ser Leu Ala Ser Leu Ala Thr Phe
        50                  55                  60

Leu Met Pro Leu Ile Ala Leu Leu Ala Tyr Asp Ala Ile Val Gly
65                  70                  75                  80

Glu Asp Glu Gly Gly Thr Leu Met Leu Leu Thr Tyr Pro Leu Gly
                85                  90                  95

Arg Gly Glu Ile Leu Leu Gly Lys Phe Val Gly His Gly Leu Ile Leu
                100                 105                 110

Ala Leu Ala Val Leu Ile Gly Phe Gly Gly Ala Leu Ala Ile Ala
            115                 120                 125

Leu Leu Val Glu Asp Ile Glu Leu Gly Leu Leu Leu Trp Ala Phe Gly
        130                 135                 140

Arg Phe Met Val Ser Ser Thr Leu Leu Gly Trp Val Phe Leu Ala Leu
145                 150                 155                 160

Ala Tyr Val Leu Ser Gly Lys Val Asn Glu Lys Ser Ser Ala Ala Gly
                165                 170                 175

Leu Ala Leu Gly Ile Trp Phe Leu Phe Val Leu Val Phe Asp Leu Val
            180                 185                 190

Leu Leu Ala Leu Leu Val Leu Ser Glu Gly Lys Phe Ser Pro Glu Leu
        195                 200                 205

Leu Pro Trp Leu Leu Leu Asn Pro Thr Asp Ile Tyr Arg Leu Ile
210                 215                 220

Asn Leu Ser Gly Phe Glu Gly Gly Gly Ala Met Gly Val Leu Ser Leu
225                 230                 235                 240

Gly Ser Asp Leu Pro Val Pro Asn Ala Val Leu Trp Leu Cys Leu Leu
                245                 250                 255
```

Ala Trp Ala Gly Ala Ser Leu Leu Leu Ala Tyr Gly Ile Phe Arg Arg
              260                 265                 270

Arg Leu Ala
    275

<210> SEQ ID NO 38
<211> LENGTH: 828
<212> TYPE: DNA
<213> ORGANISM: Pseudomonas stutzeri

<400> SEQUENCE: 38

| | | | | | |
|---|---|---|---|---|---|
| atgaaccagg | tctggaacat | cgcccgcaag | gaactcagcg | atggcctgcg | caaccgctgg | 60 |
| ctgctggcca | tcagcctgtt | gttcgcggtg | ctggccgtgg | ggatcgcctg | gctcggtgcg | 120 |
| gccgcctcgg | ggcaggtggg | gttcaccctcg | atcccggcga | ccatcgccag | cctgccagc | 180 |
| ctggccacct | tcctgatgcc | gctgatcgcg | ctgctgctgg | cctatgacgc | catcgtcggc | 240 |
| gaggacgaag | gcggcacgct | gatgctgctg | ctgacctacc | cgctggggcg | cggcgagatc | 300 |
| ctgctcggca | agttcgtcgg | ccacgggctg | atccttgccc | tggcggtgtt | gatcggcttc | 360 |
| ggcggcgccg | ctctggccat | cgccctgctg | gtcgaggata | tcgagctggg | cctgctgctc | 420 |
| tgggccttcg | gtcgcttcat | ggtttcctcc | acgctgctgg | gctgggtgtt | ccttgccctg | 480 |
| gcctacgtgc | tcagcggcaa | ggtcaacgag | aaatccagcg | ccgccggcct | ggcgctgggg | 540 |
| atctggttcc | tgttcgtgct | ggtgttcgac | ctggtgctgc | tggcgctgct | ggtgctcagc | 600 |
| gaaggcaagt | tcagccccga | gttgctgccc | tggctgctgc | tgctcaaccc | caccgacatc | 660 |
| taccggctga | tcaacctgtc | cggcttcgag | ggcggcggcg | ccatgggcgt | gctgtcgctg | 720 |
| ggcagcgacc | tgcccgtgcc | gaacgccgtg | ctctggctct | gcctgttggc | ctgggcaggc | 780 |
| gcatcgctgc | tgctggccta | tggcatcttc | cgtcggcgcc | tggcctga | | 828 |

<210> SEQ ID NO 39
<211> LENGTH: 828
<212> TYPE: DNA
<213> ORGANISM: Artificial
<220> FEATURE:
<223> OTHER INFORMATION: Codon optimized NosY gene

<400> SEQUENCE: 39

| | | | | | |
|---|---|---|---|---|---|
| atgaaccaag | tgtggaacat | tgcgcgtaaa | gagttgtctg | atggtctccg | taaccgctgg | 60 |
| ttacttgcta | tttcattact | ctttgccgta | ttggctgtcg | gcatcgcttg | gctcggcgcc | 120 |
| gctgcgtctg | gtcaagttgg | tttcacgtct | atcccagcga | ctatcgcgtc | cttagcgtca | 180 |
| ctggcaactt | tcctgatgcc | tttaattgca | cttcttctcg | cttatgatgc | cattgtcggt | 240 |
| gaagatgagg | gggggactct | catgttatta | ctgacctacc | cgttgggccg | tggggaaatc | 300 |
| ttactgggca | agttcgtggg | gcatggctta | atcttggctt | tagctgtact | catcgggttt | 360 |
| ggcggggcgg | ctttagctat | tgccctcttg | gtcgaggaca | ttgaacttgg | ctgctgctc | 420 |
| tgggcattcg | gccgcttcat | ggtgagtagt | acgctcctcg | ggtgggtatt | tttggccctc | 480 |
| gcttacgttc | tttccggcaa | agtcaatgag | aagtcttctg | cggcaggtct | ggcgctgggg | 540 |
| atttggttct | tgtttgtact | tgtgttcgat | cttgtccttt | tagctctgct | ggtattgtcc | 600 |
| gaagggaagt | ttagtcctga | attattgcct | tggcttttgt | tattgaatcc | taccgacatc | 660 |
| tatcgtctta | ttaatttgtc | cggctttgaa | ggtggtgggg | cgatgggggt | attgtcattg | 720 |
| gggagtgacc | ttcctgtacc | aaatgcggtc | ttatggcttt | gcctcctggc | ttgggccggc | 780 |

```
gcgtcattgc ttttggcgta tggcattttc cgtcgtcgct tagcttga                        828
```

<210> SEQ ID NO 40
<211> LENGTH: 275
<212> TYPE: PRT
<213> ORGANISM: Pseudomonas aeruginosa

<400> SEQUENCE: 40

```
Met Pro Val Val Trp Thr Ile Ala Arg Lys Glu Leu Ala Asp Gly Leu
1               5                   10                  15

Arg Asn Arg Trp Leu Leu Ala Ile Ser Leu Leu Phe Ala Leu Leu Ser
            20                  25                  30

Val Gly Ile Ala Trp Phe Gly Ala Ala Ala Gly Gln Val Gly Phe
        35                  40                  45

Thr Ser Val Pro Ala Thr Val Ala Ser Leu Thr Ser Leu Ala Thr Phe
    50                  55                  60

Leu Met Pro Leu Ile Ala Leu Leu Ala Tyr Asp Ala Ile Val Gly
65                  70                  75                  80

Glu Glu Glu Gly Gly Thr Leu Leu Leu Leu Thr Tyr Pro Leu Gly
                85                  90                  95

Arg Gly Gln Leu Leu Gly Lys Phe Leu Gly His Gly Leu Ile Leu
            100                 105                 110

Ala Leu Ala Thr Leu Ile Gly Phe Gly Ser Ala Ala Leu Ala Ile Leu
        115                 120                 125

Ala Leu Val Pro Glu Val Glu Ala Ala Ile Leu Leu Gly Ala Phe Gly
    130                 135                 140

Arg Phe Met Gly Ser Ser Leu Leu Leu Gly Cys Val Phe Leu Ala Leu
145                 150                 155                 160

Ala Tyr Ala Leu Ser Ser Arg Ala Ser Glu Lys Ser Ser Ala Ala Gly
                165                 170                 175

Gln Ala Leu Gly Leu Trp Phe Phe Val Leu Leu Phe Asp Leu Ala
            180                 185                 190

Leu Leu Ala Ile Leu Val Leu Ser Gln Gly His Leu Ser Pro Arg Leu
        195                 200                 205

Leu Pro Trp Leu Leu Leu Asn Pro Thr Asp Leu Tyr Arg Leu Ile
    210                 215                 220

Asn Leu Ser Gly Phe Asp Ala Ala Ala Gly Gly Val Val Pro Leu
225                 230                 235                 240

Ala Ser Asp Leu Pro Val Ser Ala Ser Ala Leu Trp Leu Ala Leu Ala
                245                 250                 255

Leu Trp Ala Cys Ala Ala Leu Ala Leu Ala His Gly Leu Phe Arg Arg
            260                 265                 270

Arg Pro Ile
        275
```

<210> SEQ ID NO 41
<211> LENGTH: 828
<212> TYPE: DNA
<213> ORGANISM: Pseudomonas aeruginosa

<400> SEQUENCE: 41

```
atgcccgtag tctggaccat cgcccgcaag gaactggccg acggcctgcg caatcgctgg     60
ctgctggcga tcagcctgct gttcgccctg ctctcggtgg gcatcgcctg gttcggcgcc   120
gccgcggccg gccaggtcgg cttcacttcg gtgccggcga cggtcgccag cctgaccagc   180
ctggccacct tcctgatgcc gctgatcgcc ctgctgctgg cctacgacgc catcgtcggc   240
```

```
gaggaggaag gcggcaccct gctgctgctc ctgacctacc cgctggggcg cggccagttg      300
ctgctcggca agttcctcgg tcacggcctg atcctcgccc tggccaccct gatcggcttc      360
ggcagcgcgg cgctggcgat cctcgcgctg gtgccggagg tcgaggcggc catcctgctg      420
ggcgccttcg gccgcttcat gggttcctcg ctgctgctcg gctgcgtgtt cctcgccctg      480
gcctacgccc tgagcagccg cgccagcgag aaatccagcg ccgccgggca ggcgctcggc      540
ctgtggttct tcttcgtcct gctgttcgac ctggccctgc tggcgatcct ggtcctcagc      600
cagggtcacc tgagcccgcg gctgctgccc tggctgttgc tgctcaaccc gaccgacctc      660
taccggctga tcaacctgtc cggcttcgac gcagccgccg ccggcggggt ggttcccctg      720
gccagcgacc tgccggtgtc cgccagcgcc ctctggctgg ccctggccct ctgggcctgc      780
gctgccctgg cgctggccca cggcctgttc cgccgccgcc ccatctga                    828

<210> SEQ ID NO 42
<211> LENGTH: 828
<212> TYPE: DNA
<213> ORGANISM: Artificial
<220> FEATURE:
<223> OTHER INFORMATION: Codon optimized NosY gene

<400> SEQUENCE: 42
atgccggtcg tgtggacgat tgcacgtaaa gagctcgccg acggccttcg taatcgctgg       60
ctccttgcaa tctcgctgtt gttcgctctc ttatccgtag ggattgcctg gttcggcgca      120
gccgcagctg gccaagttgg gttcacttcg gttcctgcga cagttgctag tctgacatcc      180
ctggccactt tcctcatgcc tttgatcgct ttgctcttgg cgtacgatgc tatcgtaggg      240
gaagaggaag gtggcacact cctgctcctg cttacttacc cattaggccg cggccagctc      300
ctcctcggga agtttctcgg tcatggcttg atcctcgcgc tggcaactct gattggtttc      360
ggttccgcag cacttgctat ccttgcactc gtgcctgaag tggaagccgc aatttttactc      420 ggtgcattcg gtcgctttat ggggtcctca cttcttttag gttgcgtgtt cctggctttg      480
gcttatgcct tatcgagccg tgctagcgaa aagtcttctg ctgcagggca agccttaggg      540
ttgtggtttt tcttcgtgtt gcttttcgac ttagcattat tggctattct ggttctgagc      600
caaggtcact tatcaccacg tctccttcca tggttactct tgcttaaccc gacagacctg      660
taccgtctga ttaacttaag cggctttgat gcagccgccg ccggggggt cgtcccttttg      720 gcttccgact tgccagtatc agccagtgcg ctttggctcg cgttggcgtt atgggcttgc      780
gcggcgttag cccttgctca tggcttgttc cgccgtcgcc caattttaa                    828

<210> SEQ ID NO 43
<211> LENGTH: 274
<212> TYPE: PRT
<213> ORGANISM: Pseudomonas versutus

<400> SEQUENCE: 43

Met Ile Arg Arg Ile Leu Ser Thr Ala Ala Leu Glu Phe Arg Ile Ala
1               5                   10                  15

Leu Arg Asn Arg Trp Val Ala Ile Ala Thr Ala Leu Met Val Val Phe
            20                  25                  30

Ala Leu Val Leu Ala Ala Ala Gly Ala Ala Pro Thr Gly Asp Ile Gly
        35                  40                  45

Ala Asp Arg Leu Ser Val Val Val Ala Ser Leu Thr Ser Leu Ala Val
    50                  55                  60
```

Tyr Leu Val Pro Leu Leu Ala Leu Leu Met Ser Phe Asp Ala Val Ala
65                  70                  75                  80

Gly Glu Val Glu Arg Gly Thr Leu Pro Leu Leu Thr Tyr Pro Val
            85                  90                  95

Ala Arg Ala Glu Val Leu Ala Gly Lys Leu Val Ala His Met Ala Ile
                100                 105                 110

Leu Ala Leu Ala Val Gly Ala Gly Tyr Gly Ala Ala Leu Ala Ala
        115                 120                 125

Val Trp Ser Asp Pro Ala Ser Thr Ala Gly Leu Pro Ala Leu Trp Arg
130                 135                 140

Leu Met Trp Ser Ser Thr Leu Leu Gly Ala Thr Phe Leu Gly Ala Gly
145                 150                 155                 160

Tyr Ala Leu Ser Ser Ile Ala Arg Arg Pro Ser Gly Ala Ala Gly Leu
                165                 170                 175

Ala Val Gly Leu Trp Leu Gly Leu Val Val Leu Tyr Asp Leu Ala Leu
            180                 185                 190

Leu Ala Leu Ile Val Ala Asp Gly Gly Gly Phe Thr Thr Glu Val
        195                 200                 205

Leu Pro Val Ala Leu Leu Ala Asn Pro Ala Asp Ala Phe Arg Leu Phe
210                 215                 220

Asn Leu Ser Ala Ala Gln Ala Thr Ala Ala Ala Gly Val Gly Gly
225                 230                 235                 240

Ala Ala Ala Thr Ile Pro Leu Trp Gln Ser Ala Leu Ser Val Leu Ala
                245                 250                 255

Trp Pro Leu Ala Ala Leu Gly Leu Ala Ile Ala Ala Phe Arg Lys Val
            260                 265                 270

Thr Pro

<210> SEQ ID NO 44
<211> LENGTH: 825
<212> TYPE: DNA
<213> ORGANISM: Pseudomonas versutus

<400> SEQUENCE: 44
atgatccgcc gcatcctttc caccgcggcg ctggagttcc gcatcgcgct gcgcaaccgc      60
tgggtcgcca tcgccaccgc gctgatggtg gtctttgcgc tggtgctggc ggcggcgggt     120
gccgcgccca ccggcgacat cggcgccgac cggctgtccg tcgtcgtcgc ctcgctgacc     180
tcgcttgccg tctacctggc cgctgctgcg gctgctga tgagcttcga tgccgtcgcc      240
ggcgaggtcg agcgcggcac cttgcccttg ctgctgacct atcccgtggc gcgggccgag     300
gtgctggccg gcaagctggt cgcgcatatg gcgattctgg cgctggcggt gggcgcgggc     360
tacggcgcgc ggccctggc ggcggtctgg agcgatccgg cctcgaccgc ggggcttccg      420
gcgctgtggc ggctgatgtg gagctcgacc ctgctgggcg cgaccttcct gggcgccggc     480
tatgcgctgt ccagcatcgc gcgccggccc tcgggcgcgg ccgggctggc ggtcgggctg     540 tggctgggc tggtggtgct ttacgacctg gccctgctgg cgctgatcgt cgccgatggc      600
ggcggcggct tcaccaccga ggtgctgccg gtcgcgctgc ttgccaaccc ggccgacgcc     660
ttccgcctgt tcaacctctc ggccgcccag gccaccgccg ccgctgccgg cgtcggcggg     720
gccgccgcga ccatcccgct ttggcaatcg gcgctgtcgg tcctggcctg gccgctggcc     780
gcgcttggcc ttgccattgc cgcattccga aaggtcacgc catga                     825

<210> SEQ ID NO 45

<211> LENGTH: 825
<212> TYPE: DNA
<213> ORGANISM: Artificial
<220> FEATURE:
<223> OTHER INFORMATION: Codon optimized NosY gene

<400> SEQUENCE: 45

```
atgatccgtc gcattctcag tacagcggcc ttggaatttc gtattgctct ccgcaaccgt      60
tgggtggcca ttgcgactgc actcatggta gtgtttgctt tagttcttgc ggctgctggc     120
gcggcgccaa cgggtgatat tggcgcggac cgtttgagcg tagttgtggc ctcgctcact     180
tcactcgcag tgtatcttgt tcctctgtta gcacttctta tgtcgttcga cgctgtagct     240
ggcgaggtcg agcgcgggac gcttccgttg ttgcttacct atccggttgc acgcgcggag     300
gtactcgcgg ggaagctcgt tgcccacatg gcaatlltag ctttagccgt gggtgctggt     360
tatggtgcag cagcgctcgc agcagtttgg tcggaccctg ccagcactgc agggcttcca     420
gcactttggc gtcttatgtg gagttccaca ttgctgggtg caacctttct gggcgcaggc     480
tacgcacttt cctcgattgc acgccgccct tctggcgcag ccgggttagc ggtggggctg     540
tggttgggcc tcgttgttct ttatgatctc gcattgttgg cactcatcgt agccgatggt     600
ggtggtggtt tcaccacgga agtgctccca gtggctttat agcgaaccc agccgatgcg      660
tttcgccttt ttaatttgtc cgctgcacaa gcaacagctg ccgctgcagg ggttggtggc     720
gctgcagcca ctatcccact ttggcaaagc ccctcagcg ttctggcgtg gccattggct      780
gcattgggtc ttgcgattgc ggcgttccgt aaggttactc cgtaa                      825
```

<210> SEQ ID NO 46
<211> LENGTH: 341
<212> TYPE: PRT
<213> ORGANISM: Pseudomonas stutzeri

<400> SEQUENCE: 46

```
Met Gly Arg Ala Ser Leu Gln Pro Val Ile Ala Val Ala Leu Ala Ala
1               5                   10                  15

Ala Leu Thr Gly Cys Leu Phe Gln Asp Lys Val Glu Asp Phe Gly Gly
            20                  25                  30

Pro Thr Met Gly Ser Thr Tyr Ser Val Lys Tyr Val Ala Ser Asp Gly
        35                  40                  45

Ala Ala Ala Lys Ala Gln Leu Gln Arg Glu Thr Glu Ser Ile Leu Ala
    50                  55                  60

Gln Leu Asp Glu Gln Leu Ser Thr Tyr Arg Ala Asp Ser Asp Ile Glu
65                  70                  75                  80

Ala Phe Asn Ala Leu Pro Ala Gly Gln Cys Met Ala Met Pro Glu Ser
                85                  90                  95

Ala Arg Glu Leu Val Leu Ala Gly Gln Gln Leu Ser Gln Glu Ser Asp
            100                 105                 110

Gly Ala Leu Asp Leu Thr Ile Gln Pro Leu Leu Asn Leu Trp Gly Phe
        115                 120                 125

Gly Pro Gln Gly Arg Arg Glu Gln Val Pro Ser Ala Glu Glu Ile Ala
    130                 135                 140

Arg Ala Arg Glu Thr Val Gly His Arg His Leu Gln Val Val Gly Glu
145                 150                 155                 160

Gln Leu Cys Lys Asp Ala Ala Val Glu Val Asp Phe Asn Ser Ile Ala
                165                 170                 175

Ala Gly Tyr Ala Val Asp Leu Val Ala Gln Arg Leu Glu Ala Leu Gly
            180                 185                 190
```

Val Glu Ser Tyr Leu Val Glu Ile Thr Gly Glu Leu Lys Ala Arg Gly
            195                 200                 205

Arg Lys Pro Gly Asp Ala Pro Trp Arg Ile Ala Ile Glu Ala Pro Arg
        210                 215                 220

Asp Asn Glu Arg Val Ala Gln Arg Val Ile Glu Leu Asp Gly Tyr Gly
225                 230                 235                 240

Val Ser Thr Ser Gly Asp Tyr Arg Asn Tyr Phe Glu Arg Asp Gly Lys
                245                 250                 255

Arg Tyr Ser His Thr Leu Asp Pro Gln Thr Gly Ala Pro Ile Glu His
            260                 265                 270

Arg Leu Ala Ala Val Thr Val Val Asp Pro Ser Ala Leu Arg Ala Asp
        275                 280                 285

Gly Leu Ser Thr Val Leu Met Val Leu Gly Pro Glu Arg Gly Leu Ala
290                 295                 300

Tyr Ala Ala Glu His Arg Ile Ala Ala Leu Phe Val Ile His Glu Glu
305                 310                 315                 320

Gln Glu Phe Ile Ser Lys Ser Thr Ala Ala Phe Asp Glu Leu Phe Gly
                325                 330                 335

Ala Gly Ala Glu Gln
            340

<210> SEQ ID NO 47
<211> LENGTH: 1026
<212> TYPE: DNA
<213> ORGANISM: Pseudomonas stutzeri

<400> SEQUENCE: 47
atgggccgag cgtcactcca acccgtcatc gctgtcgccc tggcggcagc cctgacgggt      60
tgtctgtttc aggacaaggt agaagacttc ggtggcccga ccatgggcag tacctactcg     120
gtgaagtacg ttgccagtga tggtgcggct gccaaggcac aactgcagcg cgagaccgaa     180
tcgattctgg cccagctgga cgagcagttg tcgacctacc gcgccgattc ggatatcgaa     240
gccttcaatg ccctcccggc agggcagtgc atggccatgc ccgagtccgc ccgcgagctc     300
gtgctggctg ggcagcagct gtcgcaggaa agcgacggcg cactggacct gaccattcag     360
ccgctgctca acctctgggg gttcggcccg caggggcgcc gtgagcaggt accttctgcc     420
gaggaaattg ccagggcccg cgagactgtc ggtcaccggc atctgcaggt tgtcggcgag     480
cagctgtgca aggatgcggc cgtcgaggtc gatttcaaca gcatcgctgc gggttacgct     540
gtcgatctgg tggcgcaaag gctggaagcg ctcggggtcg aaagctatct ggtggaaatc     600
actggcgagc tcaaggcacg aggccgaaag ccgggtgacg cgccgtggcg gatcgccatc     660
gaagcgccgc gggataatga gcgtgtggcg cagcgcgtca tcgagctcga tggctatggc     720
gtttccacct cgggtgacta ccgcaattat ttcgagcgtg atggcaagcg ctactcgcat     780
acgctggatc cgcaaaccgg tgccccgatc gagcatcgcc tggcggccgt gacggtcgtc     840
gatccatcag cactgcgcgc ggacgggttg tctaccgtcc tgatggtgct ggggccggaa     900
cgtggcctgg cgtatgccgc ggagcacagg atcgcagcgc tcttcgtgat tcatgaagag     960
caggaattca tcagcaaaag caccgcagcc ttcgatgagc tgttcggtgc gggagcagag    1020
caatga                                                              1026

<210> SEQ ID NO 48
<211> LENGTH: 1026
<212> TYPE: DNA

<210> SEQ ID NO 48
<211> LENGTH: 1026
<212> TYPE: DNA
<213> ORGANISM: Artificial
<220> FEATURE:
<223> OTHER INFORMATION: Codon optimized apbE gene

<400> SEQUENCE: 48

```
atgggggcgtg cgagcctgca accagtaatt gctgttgctt tagcggcggc gctgaccggt      60
tgccttttcc aggataaggt cgaagatttt ggggggccga ccatgggtag tacttactct     120
gtcaaatacg tcgccagcga tggcgcggct gcgaaagctc aactccaacg cgaaactgag     180
agtatcttgg cacagttgga tgagcaactc tccacttatc gtgctgacag cgatattgaa     240
gcctttaacg ccctgccagc tggtcaatgc atggcgatgc cagaaagcgc tcgcgaactg     300
gtattagcag gtcagcaact tagtcaagag tccgacggtg cgctggatct cacaatccaa     360
ccattactga atttatgggg tttcggccct caggaccgcc gtgaacaagt cccatcggca     420
gaggaaatcg ctcgtgcccg tgagaccgtg ggtcatcgtc atctccaggt tgtgggcgaa     480
caactgtgca aggacgcagc tgtcgaggtg gattttaact caattgcggc aggctatgct     540
gtggacctcg ttcacagcg tcttgaagcg ctcggtgttg agtcttatct ggtggaaatc     600
actggggaac tgaaggcccg tggtcgcaaa ccaggcgatg cgccgtggcg tatcgcgatc     660
gaagctccgc gtgataacga gcgtgtgcg cagcgtgtaa ttgaattgga tggttacggc     720
gtcagcacct caggtgacta tcgcaactat tttgaacgtg acgggaagcg ttactctcac     780
actctcgatc ctcagaccgg cgcacctatc gaacaccgcc tggctgcggt aacggtggta     840
gatccatcag ctcttcgcgc agatggggtg tccactgtgc ttatggtgct cggcccagaa     900
cgtgggttgg cgtatgcggc tgagcaccgt atcgcggcac tctttgtgat ccatgaggaa     960
caggaattta tcagcaaatc cactgccgct tttgacgagc tcttcggggc gggggcagag    1020
cagtga                                                                1026
```

<210> SEQ ID NO 49
<211> LENGTH: 333
<212> TYPE: PRT
<213> ORGANISM: Pseudomonas aeruginosa

<400> SEQUENCE: 49

```
Met Ala Gly Leu Ala Ala Leu Ala Leu Val Leu Ala Gly Cys Gly Asp
1               5                   10                  15

Thr Leu Glu Ser Phe Gly Gly Pro Thr Met Gly Ser Thr Tyr Ser Ile
            20                  25                  30

Lys Tyr Val Arg Gly Ala Ser Ala Pro Asp Val Gln Thr Ala Lys Ala
        35                  40                  45

Ala Val Glu Ala Ile Leu Ala Glu Val Asp Arg Gln Met Ser Thr Tyr
    50                  55                  60

Arg Asp Asp Ser Leu Val Ser Arg Phe Asn Ala Leu Pro Ala Gln Ser
65                  70                  75                  80

Cys Met Glu Leu Pro Pro Met Leu Glu Leu Leu Arg Tyr Gly Gly
                85                  90                  95

Glu Leu Ser Glu Gln Ser Gln Gly Ala Phe Asp Met Thr Val Glu Pro
            100                 105                 110

Leu Met Asn Leu Trp Gly Phe Gly Pro Gln Ala Arg Val Glu Lys Val
        115                 120                 125

Pro Ser Ala Glu Gln Ile Ala Ala Val Arg Arg Asp Val Gly His Arg
    130                 135                 140

His Leu Arg Ile Asp Gly Gln Arg Leu Cys Lys Asp Ala Ala Val Gln
145                 150                 155                 160
```

Leu Asp Phe Asp Ser Ile Ala Ala Gly Tyr Thr Val Asp Val Gly
              165                 170                 175

Glu Arg Leu Lys Glu Leu Gly Val Arg Ser Tyr Leu Ala Glu Ile Thr
            180                 185                 190

Gly Glu Leu Lys Ala Glu Gly Arg Lys Pro Asp Gly Thr Pro Trp Arg
            195                 200                 205

Ile Ala Ile Glu Ala Pro Arg Glu Gly Gln Arg Val Ala Gln Gln Val
210                 215                 220

Leu Ala Leu Asp Gly Tyr Gly Val Ser Thr Ser Gly Asp Tyr Arg Asn
225                 230                 235                 240

Tyr Phe Glu Glu Asn Gly Gln Arg Tyr Ser His Thr Phe Asp Pro Arg
            245                 250                 255

Thr Gly Ala Pro Ile Asp His His Leu Ala Ser Val Thr Val Ile Asp
            260                 265                 270

Pro Ser Thr Arg Asn Ala Asp Gly Leu Ser Thr Leu Leu Met Ala Leu
            275                 280                 285

Gly Pro Glu Glu Gly Tyr Arg Phe Ala Glu Lys His Arg Leu Ala Ala
            290                 295                 300

Leu Phe Val Ser Arg Gln Gly Asn Gly Phe Asp Ser Arg Thr Thr Pro
305                 310                 315                 320

Arg Tyr Glu Gln Leu Phe Gly Asn Gln Gly Glu Arg Pro
            325                 330

<210> SEQ ID NO 50
<211> LENGTH: 1002
<212> TYPE: DNA
<213> ORGANISM: Pseudomonas aeruginosa

<400> SEQUENCE: 50
atggccggac tggcagcgct ggcgctggtc ctggccggtt gcggcgacac cctggaaagc      60
ttcggcggcc cgaccatggg cagcacctat tcgatcaagt acgtacgcgg cgcctcggcg     120
cccgacgtcc agacggcgaa agccgcggtg gaggcgatcc tcgccgaggt cgaccggcag     180
atgtccacct accgcgacga ttccctggtc tcgcgtttca atgcgctgcc ggcgcagtcc     240
tgcatggagc tgccgccacc gatgctggag ttgctgcgct acggcggcga gttgtcggag     300
cagagccagg cgccttcga catgaccgtc gagccgctga tgaacctctg ggcttcggt      360 ccgcaggcgc gggtagagaa ggttcccagc gccgagcaga tcgccgcggt gcgccgtgac     420
gtcggccatc gacacctgcg catcgacggc agcgcctgt gcaaggacgc cgccgtacaa     480
ttggacttcg acagcatcgc cgctggctat acggtggacg cggtaggcga acgcctgaag     540
gagctcggcg tgcgcagcta cctggcggaa atcaccggcg agttgaaagc cgaagggcgc     600
aagccggacg gcacgccctg gcgcatcgct atcgaagcgc cgcgcgaggg ccagcgggtc     660
gcccagcagg tactgcgct ggacggctac ggcgtctcga cctcgggcga ttaccgcaac     720
tatttcgaag agaacggcca gcgctattcg cacacccttcg acccgcgcac cggcgcgccg     780
atcgaccatc acctggcttc ggtcacggtg atcgatccgt cgacgcgcaa cgccgacggc     840
ctgtcgaccc tgctgatggc gctcggtccg gaggagggct accgtttcgc cgagaagcac     900
cgactggcgg cgctgttcgt cagtcgccag ggcaacggtt tcgacagccg caccacgcca     960
cgctacgagc aactgttcgg caaccaagga gaacgtccat ga                    1002

<210> SEQ ID NO 51
<211> LENGTH: 1002

```
<212> TYPE: DNA
<213> ORGANISM: Artificial
<220> FEATURE:
<223> OTHER INFORMATION: Codon optimized apbE gene

<400> SEQUENCE: 51
atggcggggt tagcagcgct ggcacttgtt ctggccgggt gtggtgacac tttggaaagt      60
ttcggcggtc ctactatggg gtccacttat tccattaagt acgttcgcgg cgcttcggct     120
cctgacgtac agaccgccaa ggccgcagtt gaggccattt ggcggaagt ggaccgccag      180
atgagtacat accgtgacga cagcctggtt tctcgtttta atgcattgcc agcgcaatcg     240
tgtatggaat tgccgccacc tatgctcgaa ttgttacgct acggtggtga gctttcagaa     300
caaagtcagg gcgcttttga tatgactgtc gagcctctga tgaacctgtg ggggttcggc     360
ccgcaagccc gcgtggaaaa ggttccttcg gcagaacaga tcgccgcggt gcgccgcgat     420
gtggggcatc gtcatctccg tatcgacggt cagcgcttgt gtaaagatgc ggccgtacaa     480
ctcgactttg attcaattgc agccggctac acagtagatg cagtgggcga gcgtttaaag     540
gagcttggtg tccgttcata tttggccgaa attactggcg aattgaaagc agaggggcgc     600
aagcctgatg gacgccatg gcgtatcgct attgaggcgc cacgcgaggg ccagcgtgtg     660
gcccagcagg tgcttgcgct cgatggctac ggtgtgtcta cgtctgggga ttaccgcaac     720
tattttgagg aaaacggtca acgctatagt cacacgtttg accctcgtac aggtgcgccg     780
atcgatcacc acttagcgtc agtcacagtg atcgacccga gcactcgcaa cgcagatggc     840
ttatccactc tcctgatggc gctcggtcct gaagagggtt accgttttgc agagaaacac     900
cgtcttgcgg cgcttttgt gagccgccaa gggaatggtt tcgactcacg gacaactccg     960
cgctatgaac aactgttcgg gaatcagggt gaacgcccat aa                       1002

<210> SEQ ID NO 52
<211> LENGTH: 302
<212> TYPE: PRT
<213> ORGANISM: Pseudomonas versutus

<400> SEQUENCE: 52

Met Ser Arg Arg Arg Phe Leu Thr Ile Thr Ala Ala Val Ala Leu Ala
1               5                   10                  15

Pro Ala Ala Leu Arg Ala Gln Pro Gly Arg His Trp Val Gly Gln Ala
                20                  25                  30

Leu Gly Ala Arg Ala Ser Ile Arg Ile Asp His Pro Glu Ala Glu Ala
            35                  40                  45

Ile Thr Ala Arg Cys Leu Ala Glu Ile Asp Arg Leu Glu Gly Ile Leu
        50                  55                  60

Ser Leu Tyr Arg Pro Asp Ser Ala Leu Ser Arg Leu Asn Arg Asp Ala
65                  70                  75                  80

Ala Leu Glu Ala Pro Pro Phe Glu Leu Leu Glu Cys Leu Ser Leu Ala
                85                  90                  95

Gly Thr Val His Arg Ala Ser Gly Gly Leu Phe Asp Pro Thr Val Gln
            100                 105                 110

Pro Leu Trp Ser Leu Trp Ala Glu Ala Ala Leu Ala Gly Arg Arg Pro
        115                 120                 125

Thr Ala Asp Glu Arg Arg Ala Ala Leu Ala Arg Thr Gly Trp Glu Arg
    130                 135                 140

Val Arg Leu Asp Ala Ala Arg Ile Thr Leu Glu Pro Gly Met Ala Leu
145                 150                 155                 160
```

Thr Leu Asn Gly Ile Gly Gln Gly Tyr Val Ala Asp Arg Val Ala Ala
            165                 170                 175

Leu Leu Glu Ala Glu Gly Leu Gly Asp Ile Leu Ile Asp Thr Gly Glu
        180                 185                 190

Leu Arg Ala Leu Gly Ser Arg Pro Asp Gly Thr Asp Trp Pro Val Arg
    195                 200                 205

Leu Ala Glu Gly Gly Ala Val Gly Leu Arg Gly Arg Ala Leu Ala Thr
210                 215                 220

Ser Ala Pro Leu Gly Thr Ser Phe Asp Gln Ala Gly Arg Asp Gly His
225                 230                 235                 240

Ile Leu Asp Pro Arg Ser Gly Ala Pro Ala Arg Pro Ala Trp Arg Ala
            245                 250                 255

Ile Ser Ile Ser Ala Pro Gly Ala Gly Leu Ala Asp Ala Leu Ser Thr
        260                 265                 270

Ala Ala Cys Leu Ala Gly Asp Arg Gln Glu Ile Leu Ala Leu Leu Ala
    275                 280                 285

Arg Phe Asp Gly Ala Arg Leu Glu Ala Ala Pro Arg Gly Ala
    290                 295                 300

<210> SEQ ID NO 53
<211> LENGTH: 909
<212> TYPE: DNA
<213> ORGANISM: Pseudomonas versutus

<400> SEQUENCE: 53
ctgtcccgcc gtcgctttct gaccatcacc gccgccgtgg cgcttgcgcc cgcggccctg     60
cgtgcccagc ccggccggca ttgggtcggg caggcgcttg gcgcccgcgc ctcgatccgc    120
atcgaccacc ccgaggccga ggcgatcacc gcccgctgcc tggccgagat cgaccggctg    180
gaaggcatcc tcagcctcta tcgtcccgac agcgccctgt cgcggctgaa ccgggacgcg    240
gcgctggagg cgccgccctt cgagctgctg gaatgcctgt cgctggccgg cacggtgcat    300
cgcgccagcg gcgggctgtt cgaccctacc gtgcagccgc tctggtcgct ctgggccgag    360
gccgccttgg ccggccgccg ccccaccgcg gacgagcgtc gcgcggcgct ggcgcgcacc    420
ggctgggagc gggtgcggct ggacgcggcg cgcatcacgc tggagccggg gatggcgctg    480
acgctgaacg gcatcggcca gggctatgtc gccgaccgcg tcgccgcgct ctctgaggcc    540
gaggggctgg gcgacatcct gatcgacacc ggcgaattgc gcgccctggg cagccggccc    600
gacggcaccg actggccggt gcggctggcc gagggcggcg cggtgggcct gcgcggccgg    660
gcgctggcga catcggcgcc gctgggcacc agcttcgacc aggcggggcg cgacggccat    720
atcctcgacc cgcgcagcgg cgcgccggcg cgtccggcct ggcgcgcgat cagcatctcg    780
gcccccggcg cgggcttggc cgatgcgctg tccaccgccg cctgcctggc cggcgaccgg    840
caggagatcc tggcgctgct ggcccgtttc gacggcgccc ggcttgaagc ggcgccgcgc    900
ggggcatag                                                          909

<210> SEQ ID NO 54
<211> LENGTH: 909
<212> TYPE: DNA
<213> ORGANISM: Artificial
<220> FEATURE:
<223> OTHER INFORMATION: Codon optimized apbE gene

<400> SEQUENCE: 54

```
atgtcacgcc gtcgtttcct gactattact gcagctgtgg cgctggctcc tgctgcgctg      60
cgcgcgcaac caggccgcca ttgggtaggc caagcattag gtgctcgtgc atccattcgc     120
attgaccatc cagaggctga ggctattaca gcacgctgct tggctgagat tgatcgcctg     180
gagggtatcc tttcccttta tcgtccggac agcgcgctta gtcgcttgaa ccgcgatgcc     240
gcgctggaag cgccaccatt cgaactcctg gaatgcttaa gtctcgctgg cacggtccat     300
cgtgcgtctg gtggtctctt tgacccaact gtgcagcctc tttggtcatt atgggccgaa     360
gccgcgcttg ccggtcgccg tccaactgcg gatgaacgtc gtgcagcttt agcacgtaca     420
ggttgggagc gcgtacgctt ggacgcagct cgtatcacct tagagccagg catggctctc     480
accctcaatg gtattgggca aggttatgtc gccgaccgcg ttgctgccct gctcgaagca     540
gagggccttg gtgacatcct gattgacacc ggggaactcc gcgctctcgg gagtcgcccg     600
gacgggaccg attggccagt acgcctcgcc gaaggtgggg ccgtggggct tcgtgggcgt     660
gcattagcta cctccgcgcc gctgggtacc tccttcgacc aggctgggcg cgacggccat     720
atcttggacc cacgttcggg cgcgccagct cgcccggctt ggcgtgcgat ctcaatttcg     780
gccccctggcg caggtcttgc agacgcctta agcaccgccg catgtttggc tggtgaccgt     840
caggaaattt tagcgttact tgcacgcttc gacggggccc gccttgaggc ggctcctcgc     900
ggtgcctga                                                             909
```